US009798976B2

(12) United States Patent
De et al.

(10) Patent No.: US 9,798,976 B2
(45) Date of Patent: Oct. 24, 2017

(54) SYSTEMS AND METHODS FOR SEMANTIC REASONING

(71) Applicants: Piali De, Harvard, MA (US); Hugh A. Stoddart, Harvard, MA (US)

(72) Inventors: Piali De, Harvard, MA (US); Hugh A. Stoddart, Harvard, MA (US)

(73) Assignee: SENSCIO SYSTEMS, Boxborough, MA (US)

( * ) Notice: Subject to any disclaimer, the term of this patent is extended or adjusted under 35 U.S.C. 154(b) by 324 days.

(21) Appl. No.: 14/331,282

(22) Filed: Jul. 15, 2014

(65) Prior Publication Data

US 2015/0019462 A1    Jan. 15, 2015

Related U.S. Application Data

(60) Provisional application No. 61/846,118, filed on Jul. 15, 2013.

(51) Int. Cl.
| | |
|---|---|
| *G06N 5/04* | (2006.01) |
| *G06N 5/02* | (2006.01) |
| *G06Q 20/00* | (2012.01) |
| *G06F 19/00* | (2011.01) |

(52) U.S. Cl.
CPC ............ *G06N 5/022* (2013.01); *G06N 5/04* (2013.01); *G06Q 20/00* (2013.01); *G06F 19/345* (2013.01)

(58) Field of Classification Search
CPC ....................................................... G06N 5/04

USPC ............................................................ 706/52
See application file for complete search history.

(56) References Cited

U.S. PATENT DOCUMENTS

| | | |
|---|---|---|
| 6,381,605 B1 | 4/2002 | Kothuri et al. |
| 7,822,699 B2 | 10/2010 | Katariya et al. |
| 2012/0158636 A1 | 6/2012 | Bowers et al. |
| 2012/0191716 A1 | 7/2012 | Omoigui |

OTHER PUBLICATIONS

N.J. Nelson, The Nearly Invisible Database or ForthQL, 22nd EuroForth Conference, Sep. 15-17, 2006, pp. 52-57, Cambridge, England.
ISR for PCT?US2014/046631, ISA/US, Oct. 27, 2014.

*Primary Examiner* — Lut Wong
(74) *Attorney, Agent, or Firm* — AKC Patents, LLC; Aliki K. Collins

(57) ABSTRACT

A system for providing semantic reasoning includes an extended semantic model, a semantic knowledge database, and an inference engine. The extended semantic model includes existing concepts for a specific knowledge domain, existing relationships among the existing concepts, and logic including conditions and processes that cause a new concept or a new relationship to be inferred from an existing concept or an existing relationship, respectively. The semantic knowledge database includes existing nodes and existing links and the existing nodes represent instances of the existing concepts, and the existing links represent instances of the existing relationships. The inference engine is configured to add new nodes and new links to the semantic knowledge database by following the logic of the extended semantic model.

22 Claims, 68 Drawing Sheets

```
( Print the telephone numbers of all my male friends in New
England. Scan nodeID 26's incoming isFriendOf links.
Execute TypeNEFriendPhone# for every linked male. Uses repertoire
function SCAN< to loop over incoming isFriendOf links and match
gender. Use an externally defined callback function
(TypeFriendPhone#) to match the state attribute to New England and
fetch and type the phone number attribute. )

: InNewEngland? ( state -- bool )
    i> state
    state " ME" $=
    state " VT" $= OR
    state " NH" $= OR
    state " MA" $= OR
    state " CT" $= OR
    state " RI" $= OR ;

: TypeFriendPhone# ( personNodeID -- )
    Person:
    DUP state SEEK InNewEngland?
    IF
        DUP phone# SEEK TYPE NL
    THEN
    DROP ;

CONTEXT Person:
" male" gender :MATCH
26 ^ TypeFriendPhone# isFriendOf SCAN<
```

*FIG. 19*

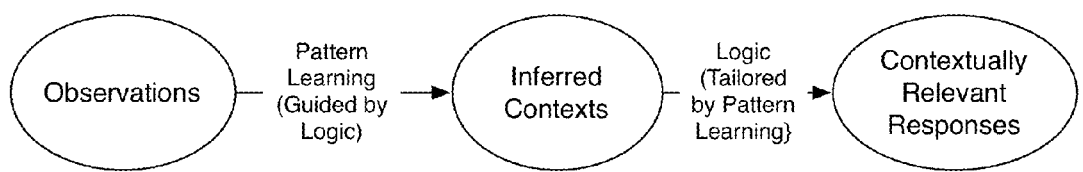

Example

| Observation | Learned Patterns --> Contexts | Relevant Responses |
|---|---|---|
| Missed medication | 1. Client's adherence drops off over time --> un-habituated<br>2. Adherence improves when reminders are accompanied with education --> wants to be healthy<br>3. No effect from increased caregiver involvement --> self-reliant | 1. Intervene with education before adherence starts to drop off to prevent drop off<br>2. Do not provide education everyday because that will lead to fatigue |

SYSTEMS AND METHODS FOR SEMANTIC REASONING

CROSS REFERENCE TO RELATED CO-PENDING APPLICATIONS

This application claims the benefit of U.S. provisional application Ser. No. 61/846,118 filed on Jul. 15, 2013 and entitled SYSTEMS AND METHODS FOR SEMANTIC REASONING, which is commonly assigned and the contents of which are expressly incorporated herein by reference.

FIELD OF THE INVENTION

The present invention relates to computer systems for information processing and in particular to systems and methods for automatically making inferences from semantic networks.

BACKGROUND OF THE INVENTION

Currently, with the rapid expansion of the World Wide Web and integrated sensors, there is more information available than is possible for the human mind to comprehend. As a result, systems and methods are needed that can automatically process data to synthesize new insights and create knowledge.

Systems and methods for creating knowledge include a method for representing knowledge and an inference engine that processes current knowledge into new knowledge. A number of different approaches have been exploited in an attempt to develop systems and methods for representing knowledge. One such method utilizes a semantic network. A semantic network is a structure for encoding knowledge. It can encode knowledge about any domain, such as military operations, financial transactions, organizational relationships, medical conditions and their treatment, to name a few.

A semantic network provides an intuitive way to encode knowledge since it mimics language. The basic building blocks of a semantic network are nodes and links. Nodes typically represent objects, real or conceptual. Links represent relationships between the objects. Nodes and links together constitute total knowledge. Referring to FIG. 1, in one example, a semantic network 80 includes nodes 81 and links 82. Nodes 81 represent concepts, such as a "Person", "Bank", or a "Bank Account". Links represent relationships between nodes, such as "owns account" 82. The combination of nodes 81 and links 82, such as "Person: A" "owns account" "Bank Account: B, encodes domain knowledge, such as A owns bank account B. New nodes and links are added to the semantic network, as new facts become known. In the example of FIG. 1, "Sue" and "Bob" represent real world knowledge about two "Persons" with "Bank Accounts" and "Transactions". At any time, knowledge can be extracted from the semantic networks through querying for links and nodes. By following certain chains of links, knowledge can be extracted from a semantic network 80. Consider, for example, the darker links 83 in FIG. 2. By following those links, one can conclude that Bob is a Person. In the example in FIG. 3, by following the darker links 84, one can conclude that Bob sends money to Sue.

In these prior art systems, knowledge needs to be explicitly added in the semantic network. New nodes and links are created through an explicit association between data and a node-link pair in the semantic network. As data become available, a computer program implements the explicit association and adds content to the semantic network. In these prior art systems, there is no mechanism for automatically and systematically adding new content to a semantic network, through a process of "inference" applied to the existing content of the semantic network. In addition, prior art semantic networks do not provide mechanisms for representing history. This precludes adding new knowledge through learning changes in the semantic network over time.

Accordingly, there is a need for systems and methods that extend a semantic network to include reasoning which adds new nodes and links to the network over time, as trends are captured or learning occurs or conclusions are drawn, by way of inferences.

SUMMARY OF THE INVENTION

The present invention provides a computer system and a computer-based method for automatically deriving insights from facts. The system and the method are used to automate processes, increase situational understanding and activate people to undertake right actions at the right time.

In general, in one aspect the invention provides a system for providing semantic reasoning including an extended semantic model, a semantic knowledge database, and an inference engine. The extended semantic model includes existing concepts for a specific knowledge domain, existing relationships among the existing concepts, and logic including conditions and processes that cause a new concept or a new relationship to be inferred from an existing concept or an existing relationship, respectively. The semantic knowledge database includes existing nodes and existing links and the existing nodes represent instances of the existing concepts, and the existing links represent instances of the existing relationships. The inference engine is configured to add new nodes and new links to the semantic knowledge database by following the logic of the extended semantic model. A computing system includes at least a processor configured to execute the logic of the extended semantic model.

Implementations of this aspect of the invention include the following. The system further includes a data normalizer configured to receive data and normalize them to the existing concepts and existing relationships of the extended semantic model. The system further includes a repertoire library and the repertoire library includes a set of functions that are identified in the extended semantic model and are invoked by the inference engine. The set of functions may be one of resolver, context-gate, collector, qualifier or operators, and each type of function fulfills a specific role in the inference process. Each function is assigned a unique identification number. The system further includes a user interface configured to query the semantic knowledge database and to provide decision support to a user. The extended semantic model further includes upstream concepts and downstream concepts and the upstream concepts are connected to the downstream concepts via relationships that are inferred from the upstream. The extended semantic model further includes notes and each note includes data associated with an existing concept. The data include values associated with an existing concept or a chain of links connecting data within an upstream concept with a downstream concept. The extended semantic model further includes properties and the properties are used by the inference engine for implementing a specific logic for instancing a link. The existing concepts include fact concepts and the fact concepts are directly observed or known. The system existing concepts include insight concepts, and the insight concepts are inferred by the inference engine from fact concepts. The relationships between fact concepts and insight concepts are automatically inferred by the inference engine. The semantic knowledge database further includes fact nodes corresponding to the fact concepts and insight nodes corresponding to the insight concepts. The semantic knowledge database further includes attributes of nodes and links and the attributes represent instances of the notes. The inference engine adds new concepts and relationships to the semantic knowledge database by first creating instances of fact nodes and associated links, next recursively updating downstream nodes, and then instancing downstream insight nodes and associated links. The system further includes an extensible meta-language and the extensible meta-language includes a vocabulary of words and a syntax. New words are configured to be added to the vocabulary by building upon existing words. The system further includes an interpreter of the extensible meta-language and the interpreter is configured to provide an interface between the inference engine and the extended semantic model and the semantic knowledge database. The extensible meta-language is used to query nodes, links and attributes in the semantic knowledge database. The extensible meta-language is an extension of a FORTH language and the interpreter is a FORTH language interpreter. The computing system is a distributed computing system. The extended semantic model is extended by adding new concepts, new fact concepts, new insight concepts, or another extended semantic model.

In general, in another aspect the invention provides a method for providing semantic reasoning including the following. First, providing an extended semantic model including existing concepts for a specific knowledge domain, existing relationships among the existing concepts, and logic including conditions and processes that cause a new concept or a new relationship to be inferred from an existing concept or an existing relationship, respectively. Next, providing a semantic knowledge database including existing nodes, and existing links and the existing nodes represent instances of the existing concepts, and the existing links represent instances of the existing relationships. Next, providing an inference engine configured to add new concepts and relationships to the semantic knowledge database by following the logic of the extended semantic model. Next, providing a computing system including at least a processor configured to execute the logic of the extended semantic model.

BRIEF DESCRIPTION OF THE DRAWINGS

Referring to the figures, wherein like numerals represent like parts throughout the several views:

FIG. 19 illustrates the meta-language interface to the inference engine;

FIG. 23 illustrates the process of establishing of context through the semantic reasoning of the present teachings;

FIG. 57 illustrates the care-portal's provision to set up doctors appointments, layered over the initial interface;

FIG. 59 illustrates the care-portal's provision to enter new medication in the care plan, indicating the dosage, type of medication, and schedule;

DETAILED DESCRIPTION OF THE INVENTION

The present invention provides a semantic reasoning computer system and a computer-based semantic reasoning method for automatically deriving insights and conclusions from facts through the use of a reasoning framework. The semantic reasoning system includes a semantic model, a semantic knowledge base, and an inference engine. The semantic model defines what needs to be known. The semantic knowledge base represents all that is known. The inference engine adds knowledge to the semantic knowledge base, by following a process for drawing conclusions. The semantic reasoning computer system and the computer-based semantic reasoning method are used to automate processes, increase situational understanding and activate people to undertake right actions at the right time.

Figure 4:
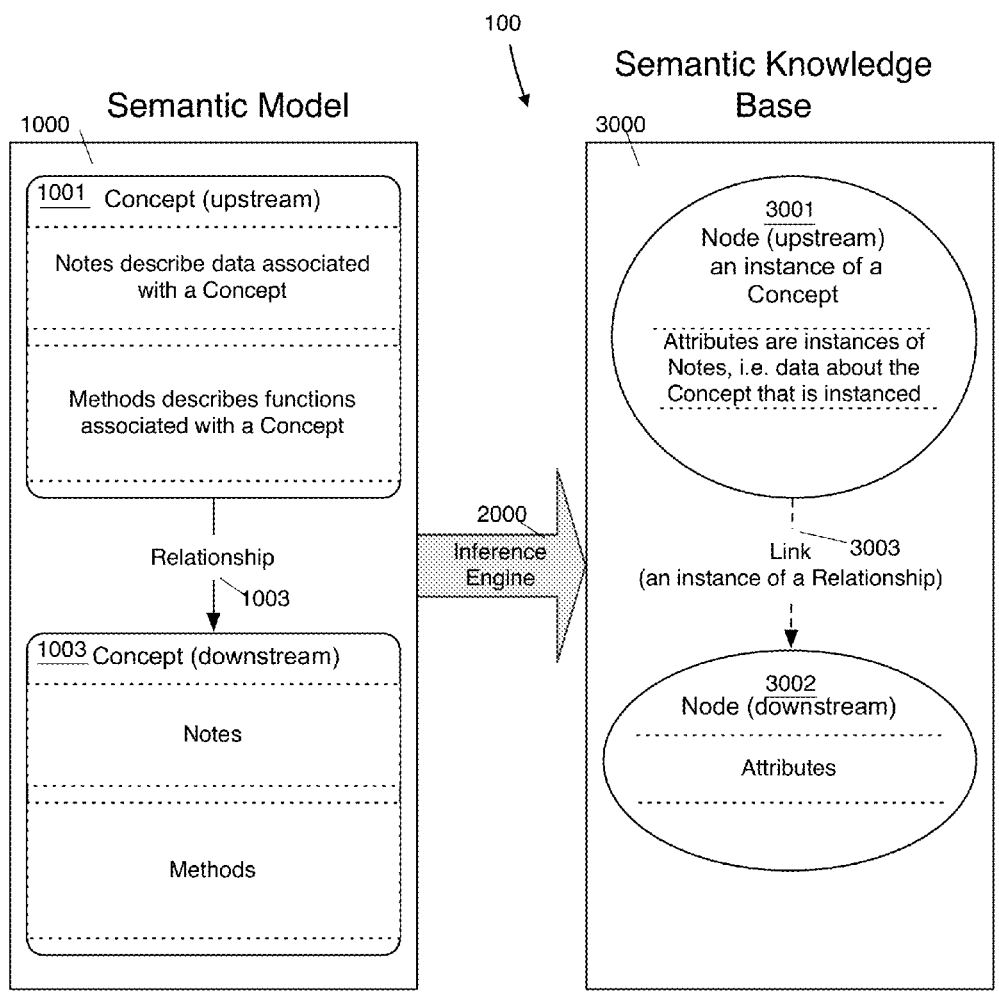
FIG. 4 illustrates a systematic approach for extending a semantic network with new knowledge derived through inference, according to this invention.

Referring to FIG. 4, a system 100 for semantic reasoning, according to the present invention includes a semantic model 1000, an inference engine 2000 and a semantic knowledge base 3000. The semantic model 1000 includes the concepts 1001, 1002 and relationships 1003 that define the contents of a domain's knowledge. The semantic model 1000 also identifies the conditions and processes that cause a new concept to be inferred from an existing concept. The semantic knowledge base 3000, is distinct from the semantic model 1000, and represents what is known as instances of the concepts and relationships defined in the semantic model 1000. The semantic knowledge base 3000 represents knowledge through nodes 3001, 3002, which are instances of concepts, links 3003 which are instances of relationships among concepts and attributes of nodes and links. The semantic knowledge base 3000 uses nodes and links to represents what is explicitly known and what is inferred. The inference engine 2000 applies the process of reasoning defined in the semantic model 1000 to continually add inferred nodes and links in the knowledge base 3000. Inferred nodes may recursively trigger further reasoning which in turn may create additional inferred nodes to continue the process of creating new knowledge.

Figure 5:
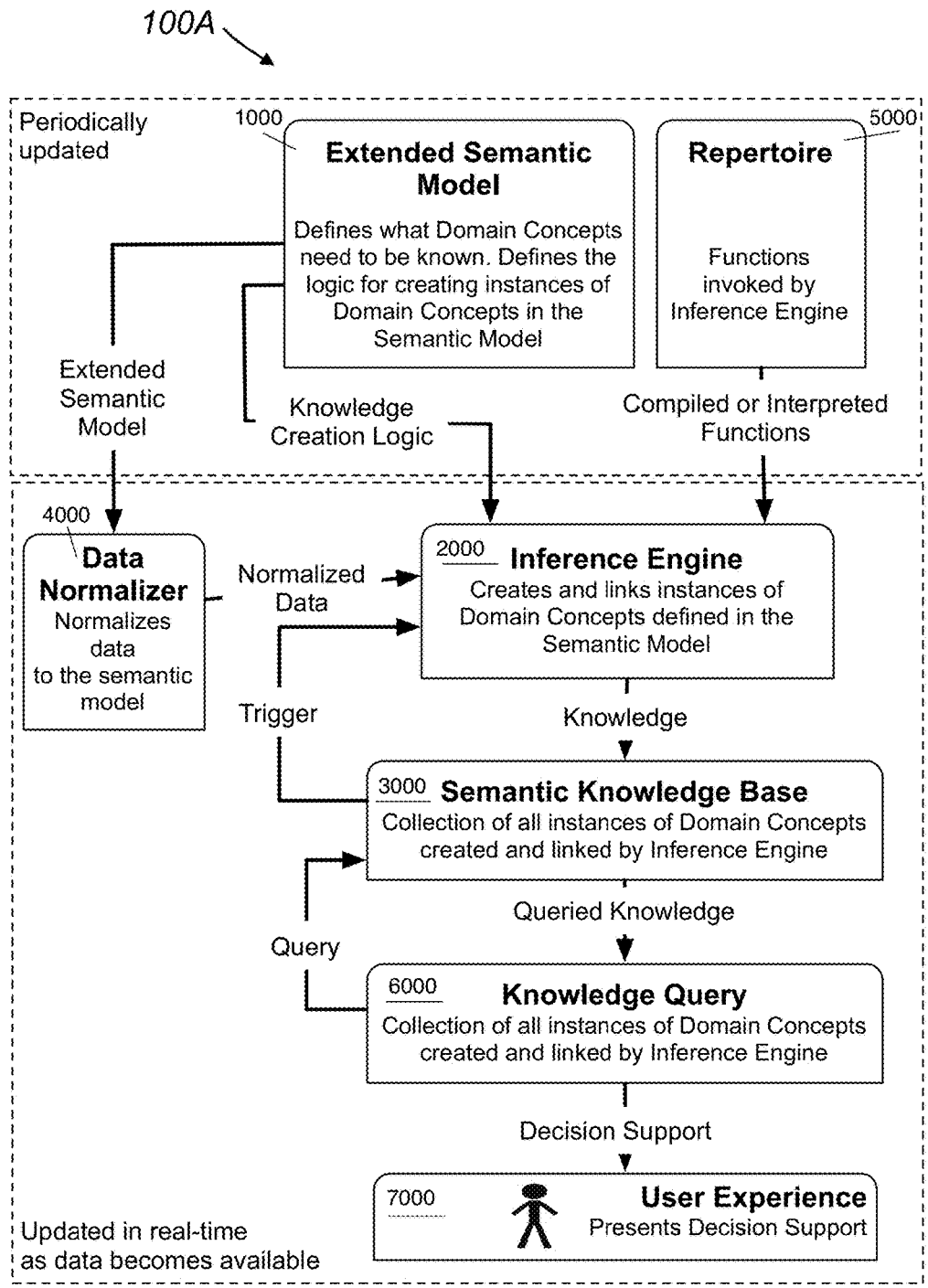
FIG. 5 illustrates the components of a semantic reasoning framework according to this invention.

Referring to FIG. 5, a system 100A to which the present invention is applied includes an extended semantic model 1000, an inference engine 2000, a semantic knowledge database 3000, a data normalizer 4000, repertoire 5000, knowledge query 6000, and user interface 7000. The extended semantic model 1000 includes the concepts and relationships that are to be known and the methods through which they are known. The inference engine 2000 uses the specifications in the extended semantic model 1000 to draw conclusions from facts, through a cascaded process of inference creating insights and insights triggering further inferencing. The semantic knowledge database 3000 stores knowledge in the form of nodes connected via links. The data normalizer 4000 includes a process and a meta-language through which data about the real world are normalized to the concepts and relationships defined in the semantic model 1000 and sent to the inference engine 2000 for conversion to nodes and links. The repertoire 5000 includes a set of functions that are identified in the semantic model 1000 and are systematically invoked by the inference engine 2000 to create instances of the semantic model 1000. The knowledge query 6000 includes a process and a meta language for querying the knowledge database 3000 for nodes, links and attributes of nodes and links. The user interface 7000 displays the queried knowledge 6000 in a cognitively friendly way.

In one example, the semantic reasoning system 100A of FIG. 5 is used to provide decision support. The inferred nodes represent knowledge that a user desires. A user queries the semantic knowledge base 3000 for inferred nodes through a user interface 7000 and the resulting inferences are presented to the user via the user interface 7000 for decision support. In another example, the semantic reasoning system of FIG. 5 is used to construct a narrative from data. One or more concepts in the semantic model may define the content of the narrative and how the narrative should be constructed. As data becomes available and represented in the semantic knowledge base, the inference engine constructs the narrative that the data supports.

Figure 6:
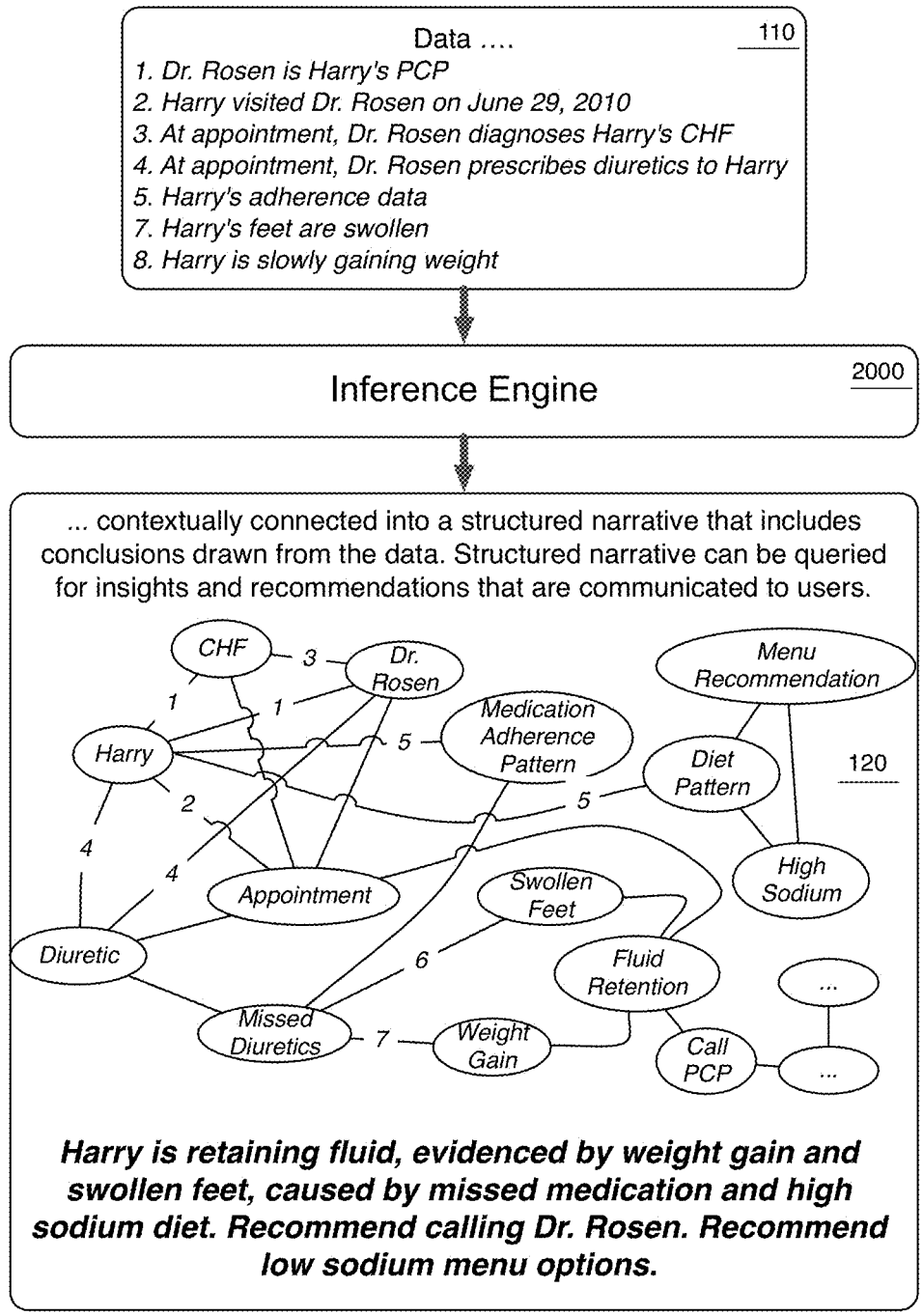
FIG. 6 depicts one use of the present teachings to create a structured narrative from disconnected data.

FIG. 6 illustrates an example of converting data 110 into a collection of linked knowledge and the associated decision support and narrative derived through a process of inference. In this example, a set of isolated facts 110 from a person's medical history is stitched together by the inference engine 2000 to create a composite picture 120 of the person's health history. Furthermore, based on the health history 120 and clinical guidelines, the inference engine 2000 is able to draw conclusions 130 (e.g. the person is retaining fluid) and recommendations (e.g. the person should call physician). Decision support may include alerts sent to caregivers when health issues, such as fluid retention, are inferred. The narrative would be a telling of the inferred condition, the supporting data and the rationale for the inference.

Extended Semantic Model

Cascading knowledge through inferencing begins with an extended semantic model 1000. The extended semantic model defines the concepts and the relationships among concepts that represent all the knowledge that is to be captured about a domain. The semantic model also defines the process through which concepts and relationships are inferred.

Figure 9:
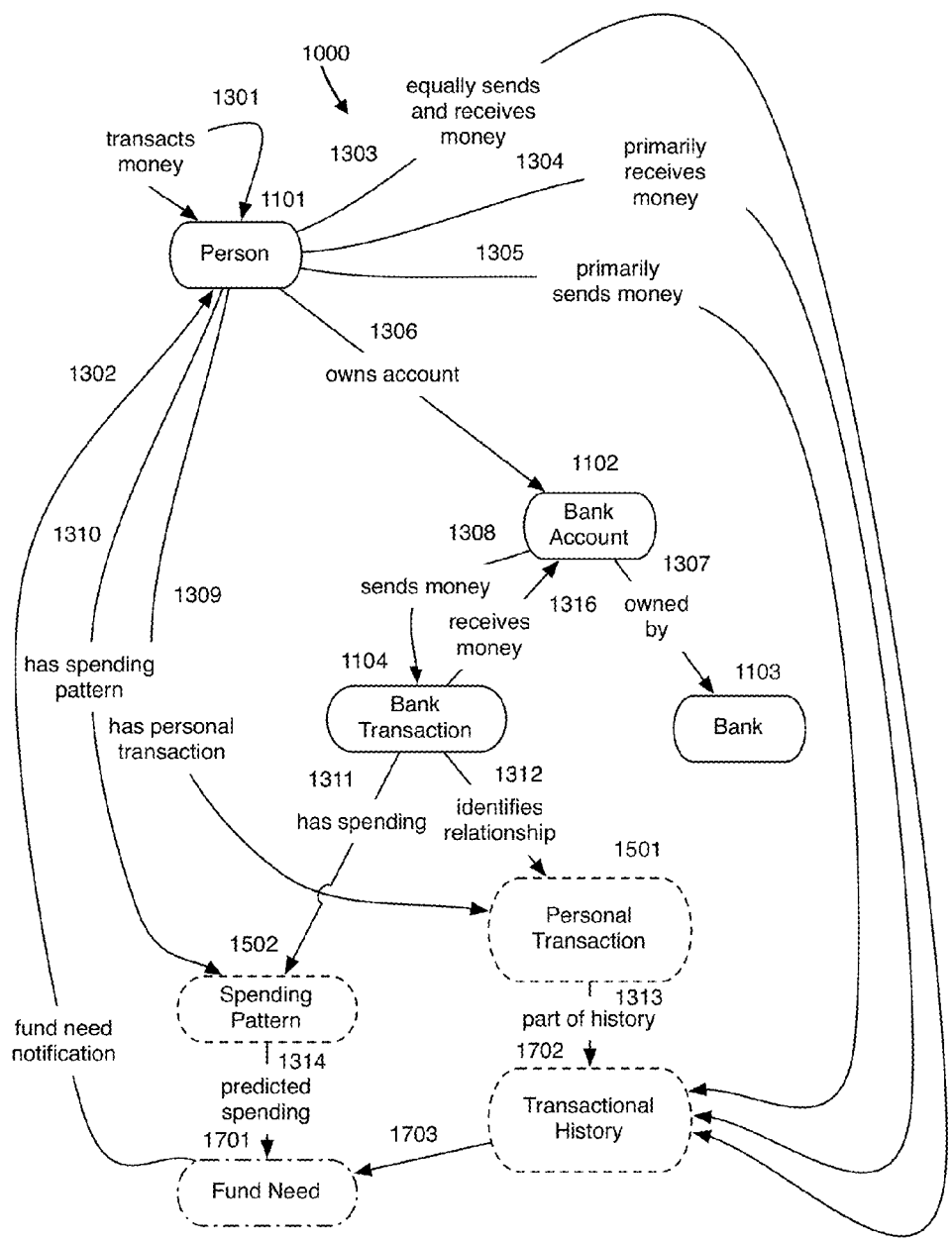
FIG. 9 illustrates an example of an extended semantic model for a Financial Transaction Analysis System (FTAS) as an extension of the semantic model of FIG. 1.
Figure 11:
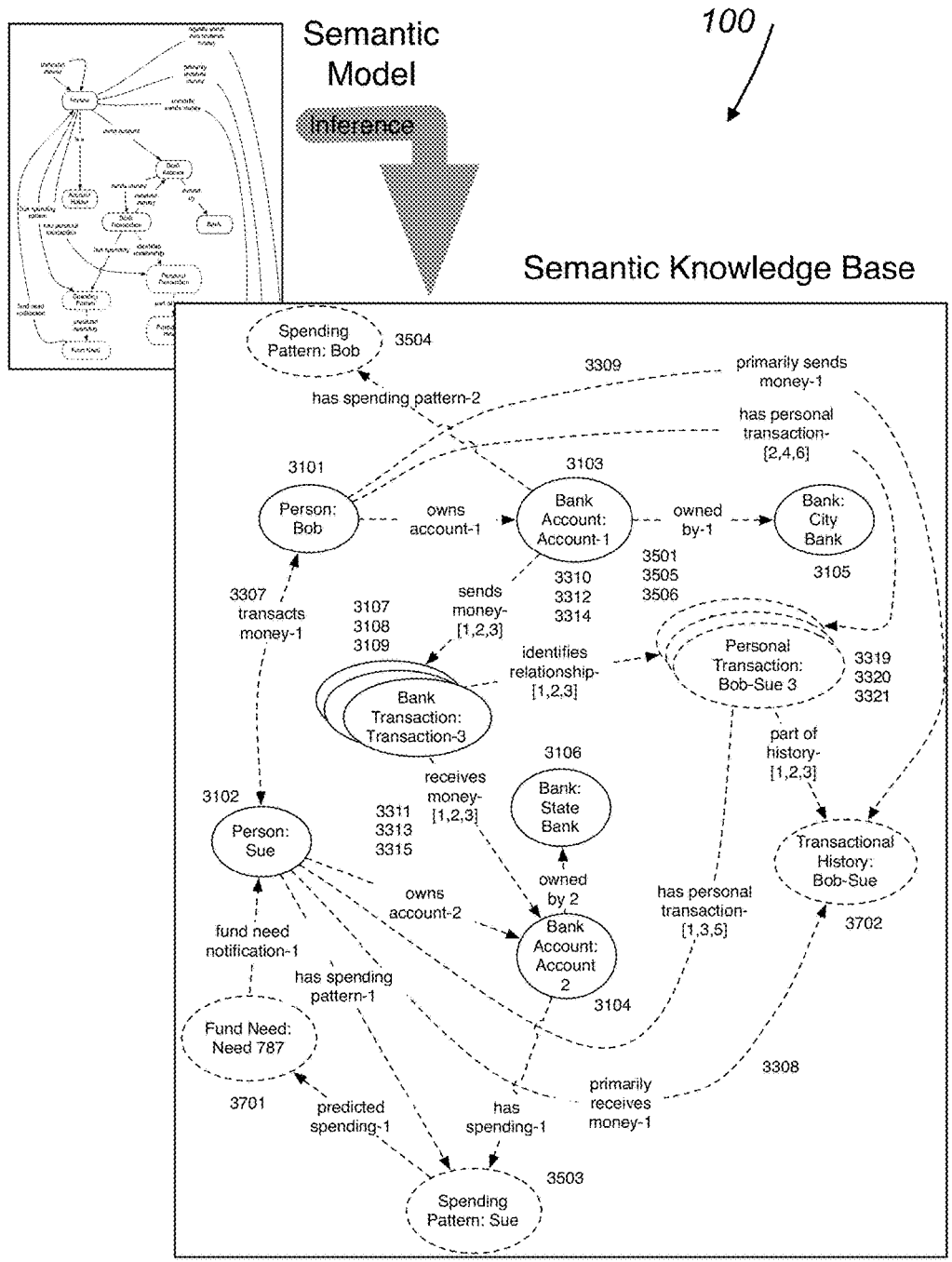
FIG. 11 illustrates an example of inferred nodes and links for the FTAS semantic model of FIG. 9.

In prior art systems, the semantic network makes no distinction between concepts and their instances. For example, in FIG. 1, "Person" and "Bob" are both nodes in the network. A link of type "is an instance" 83 represents the knowledge that Bob is a person, shown in FIG. 2. This ambiguity in whether a node represents a concept or an instance of it, is a hindrance to inferencing in the prior art semantic networks. In the present invention, representations of concepts, i.e. things that can be known, are kept separate from nodes, i.e. things that are known. Concepts are represented in the semantic model 1000 while nodes are represented in the semantic knowledge database 3000. This separation is illustrated in FIG. 9 and FIG. 11. FIG. 9 depicts "Person" as a concept while FIG. 11, its corresponding semantic model, represents "Bob" and "Sue" as instances of a "Person". This separation establishes a clear role for the inference engine, to populate the semantic knowledge base with instances of the semantic model.

Figure 1:
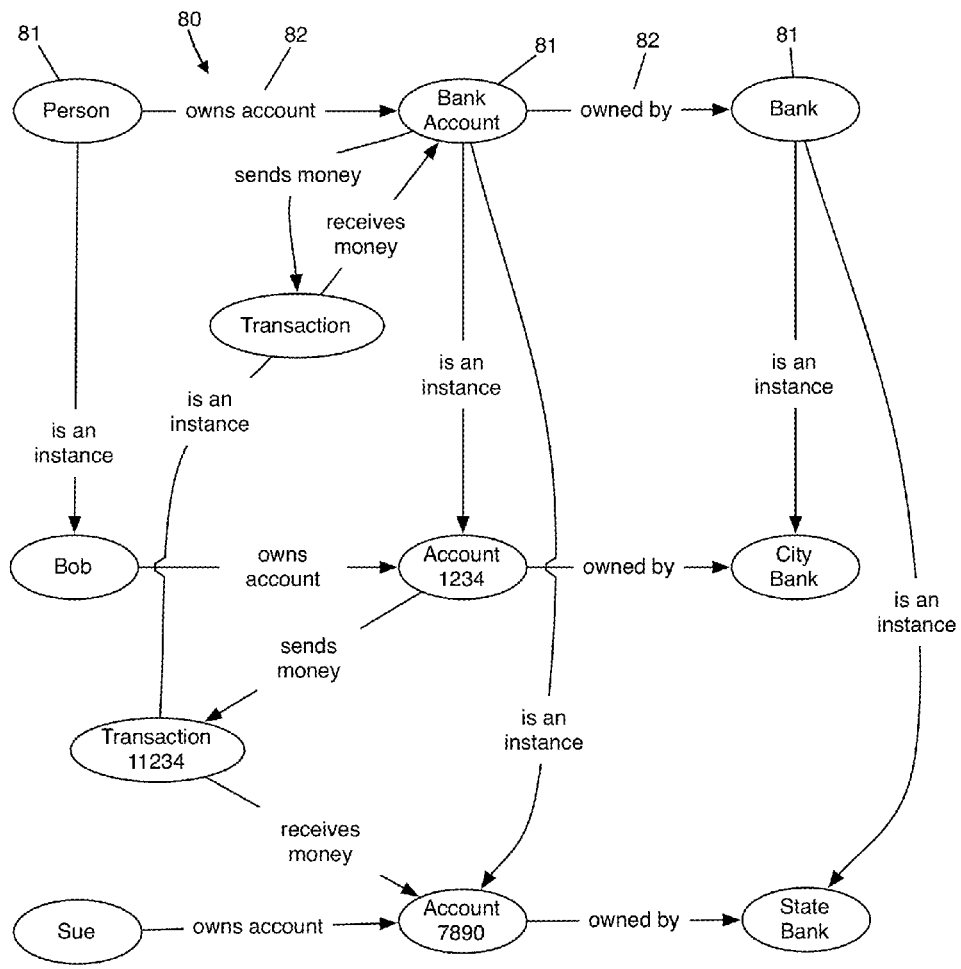
FIG. 1 depicts a prior art notional semantic network describing banks, account holders and transaction between accounts.
Figure 2:
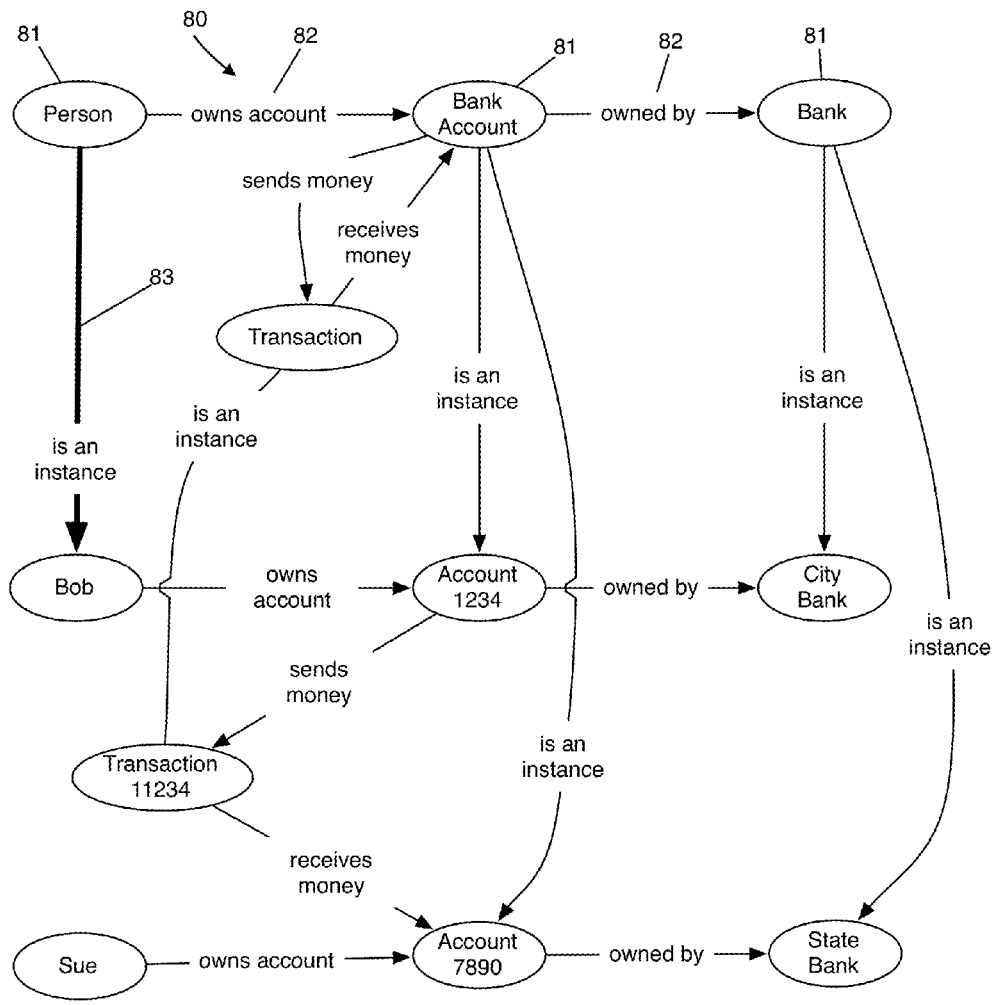
FIG. 2 is an illustration of an example for drawing inferences from the notional semantic network of FIG. 1.
Figure 3:
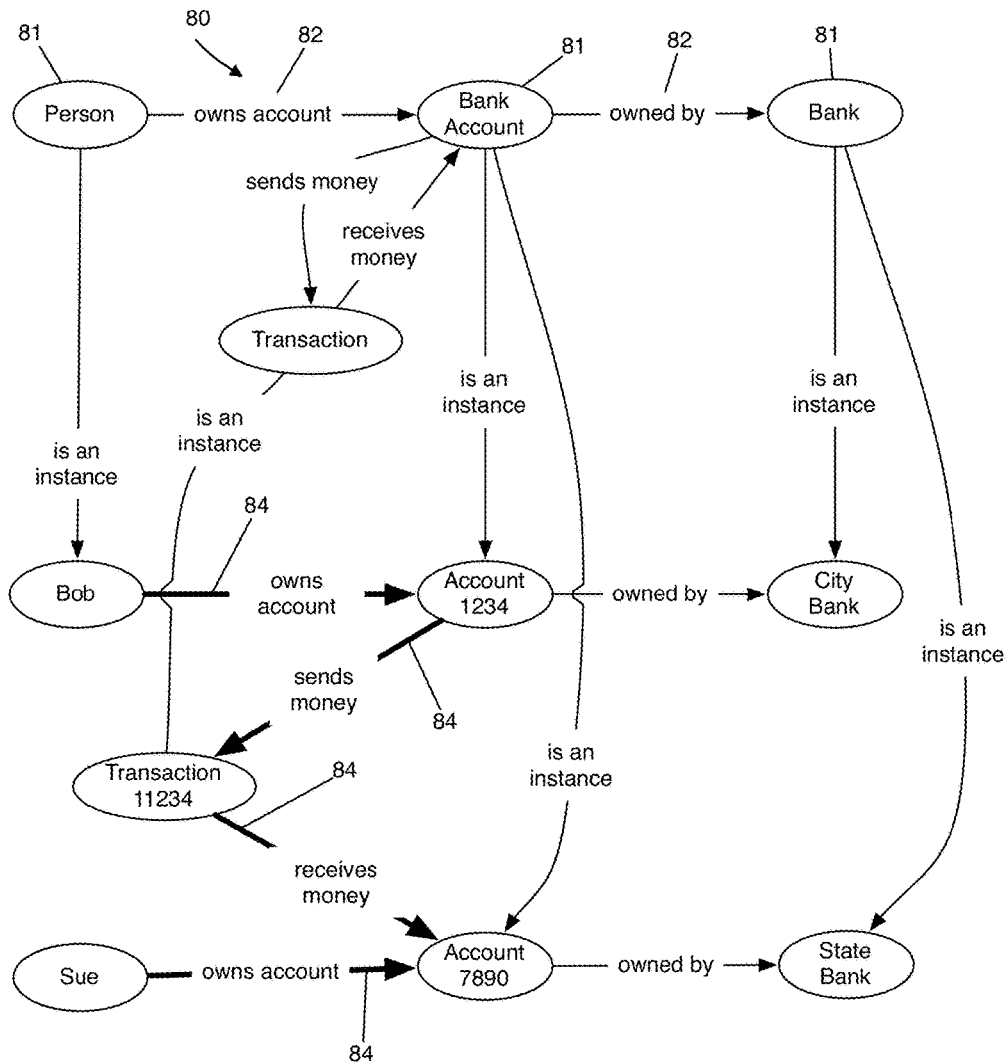
FIG. 3 is an illustration of another example for drawing inferences from the notional semantic network of FIG. 1.
Figure 7:
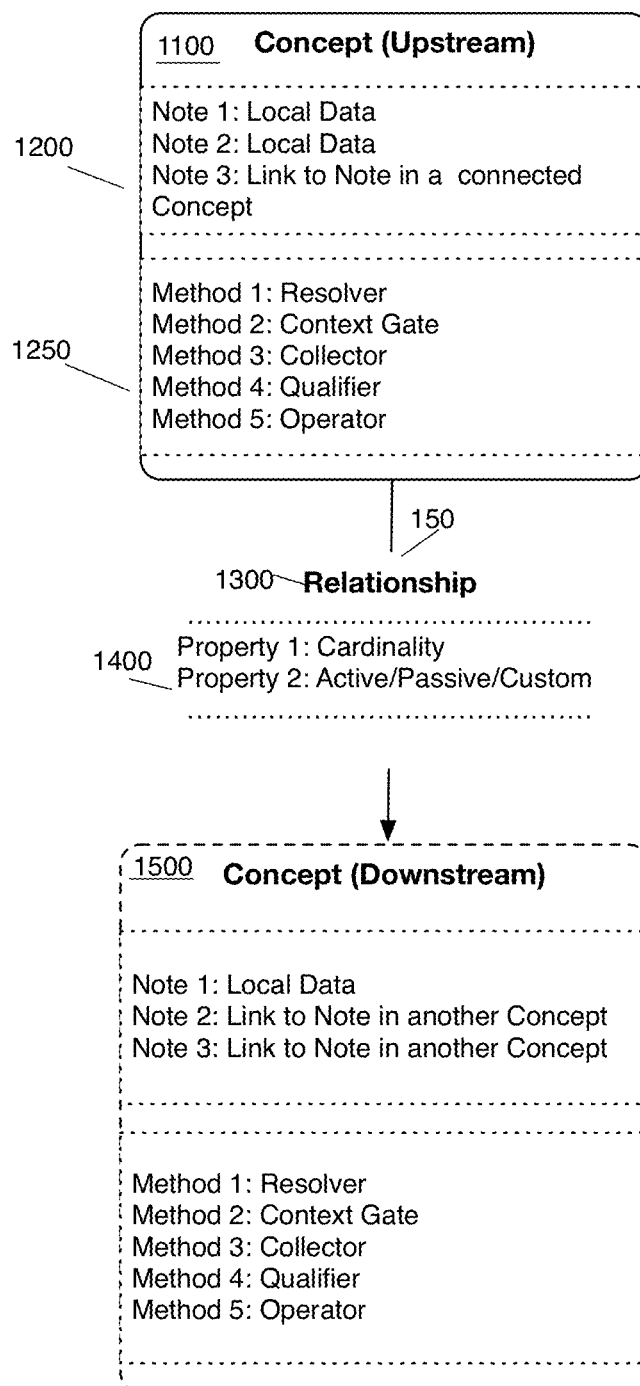
FIG. 7 illustrates an expanded definition of concepts and links in the extended semantic model.

FIG. 7 depicts various ways that the present invention extends a semantic model. The extensions are designed to overcome limitations that hinder inferencing in prior art semantic networks. In prior art systems, as depicted in FIG. 1, knowledge in a semantic network is represented as nodes 81 and links 82 connecting the nodes. The links typically have no directionality. The entire knowledge of the network is represented by which nodes are connected by which links. In the present invention, relationships that connect concepts are given directionality. The directionality is depicted by an arrow 150, as shown in FIG. 7. The directionality allows the representation of an "upstream" concept 1100, which is depicted at the origination of the arrow 150, and a "downstream" concept 1500 depicted at the termination of the arrow 150. Differentiating between upstream and downstream concept is critical to inferencing. As will be described later in FIG. 16, instantiation of an upstream concept triggers the process of determining whether downstream concepts are ready to be instantiated.

In another extension of the semantic model, concepts in the present invention are defined to have data associated with them. The data associated with a concept are referred to as notes 1200, as depicted in FIG. 7. A note can be of two types: it can refer to values that are associated with a concept such as "age" for a "Person". The note can also refer to data within upstream concepts that are connected by a chain of links to the downstream concept containing the referred note. The notes for a concept are the source of the data that the inference engine uses to draw conclusions about that concept.

In another extension of the semantic model, a concept defines multiple types of functions 1250, each of which has a well defined purpose in the inference process. FIG. 7 depicts 5 such types of functions 1250 including Resolver, Context Gate, Collector, Qualifier and Operator, among others. Each of these functions have a unique role in the inference process, as will be described later. Each of these functions is catalogued in a collection called repertoire 5000, shown in FIG. 5 and is identified by a unique number. The semantic model references these functions by their identity number. The inference engine 2000 systematically and dynamically invokes these functions 1250 during the process of creating instances of the concept, as will be described later.

In another extension of the semantic model, the relationships 1300 are defined to have certain properties. The relationships 1300 are also inferred by the inference engine 2000 and instanced in the knowledge database 3000. Properties can be of multiple types, e.g. Cardinality, Active/Passive/Custom 1400, among others. The properties 1400 defined for a relationship 1300 are interpreted by the inference engine 2000 to implement specific logics for instancing the links.

Figure 8:
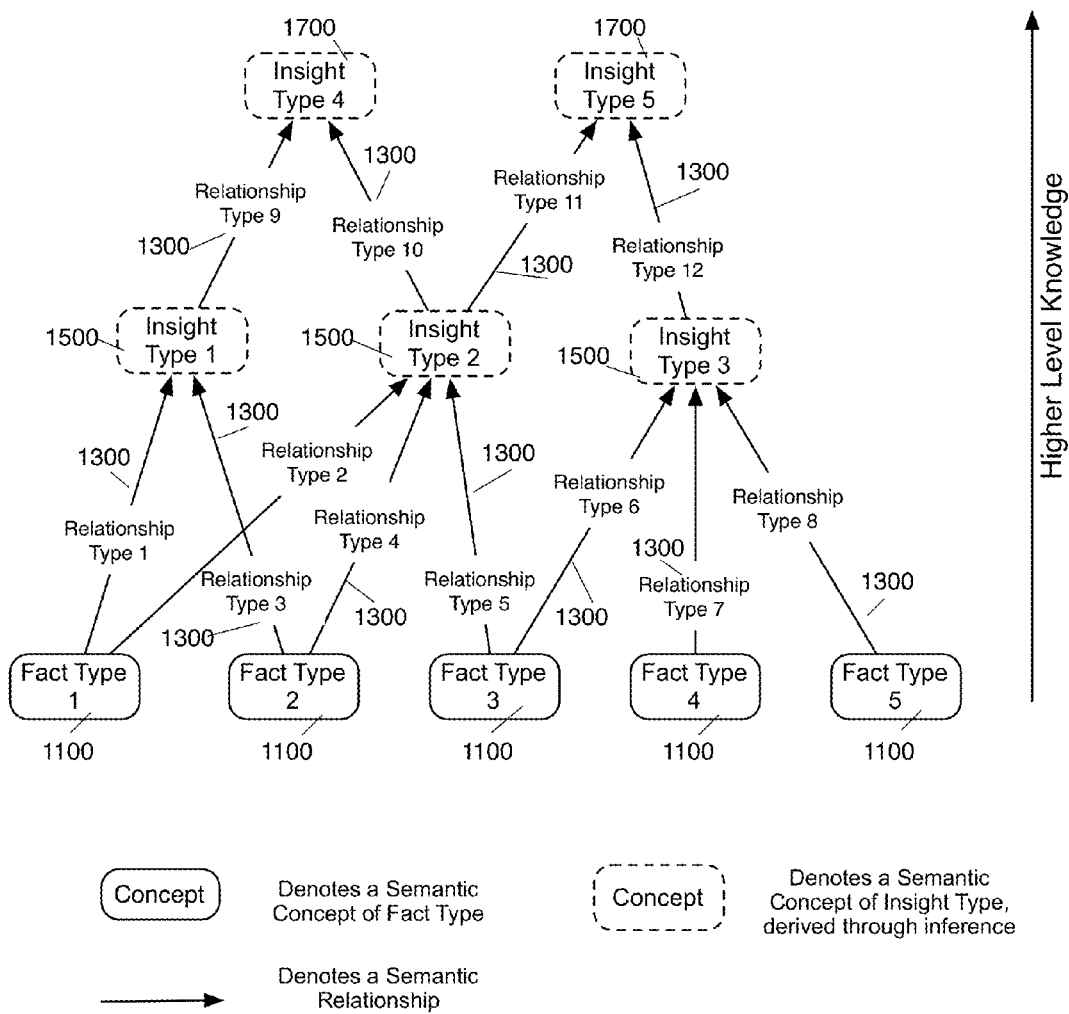
FIG. 8 illustrates that extended semantic model defines higher level knowledge concepts that are derived from lower level knowledge concepts.

FIG. 8 depicts yet another way that the semantic model 1000 is extended. In the present invention, the semantic model describes two types of concepts: "Facts" 1100 and "Insights" 1700. Facts 1100 represent what is directly observed or known about the world. Insights 1700 are concepts that are inferred from facts 1100. Relationships 1300 between facts 1100 and insights 1700 are also automatically inferred by the inference engine 2000. Insights 1700 represent intermediate knowledge derived through analysis, learning and application of logic. The highest level of insights 1700 represents the ultimate answers to be inferred. The semantic model 1000 can define as many facts 1100 and insights 1700 as needed to describe the domain knowledge.

FIG. 9 is an example of an extended semantic model 1000. It extends the semantic model of FIG. 1 to also include insight concepts that are inferred. In FIG. 9, concepts "Person" 1101, "Bank Account" 1102, "Bank Account" 1103, and "Bank Transaction" 1104 denote the same concepts depicted in FIG. 1. They represent facts 1100 that are explicitly known. "Personal Transaction" 1501, "Spending Pattern" 1502, "Fund Need" 1701 and "Transactional History" 1702 represent concepts that are inferred and hence are insights 1700. Some relationships such as "owns account" 1306 are explicitly known and represent facts 1100. Other relationships, such as "transacts money" 1301 and "primarily receives money" 1304 are inferred by the inference engine 2000.

A semantic model is extensible. Its building blocks include upstream 1100 and downstream 1500 concepts, notes 1200, functions 1250, relationships 1300, and properties 1400. The semantic model 1000 of a specific domain (e.g. the financial transactions domain depicted in FIG. 9) defines the specifics of the building blocks, e.g. "Person" is an upstream concept to "Bank Account", which are connected by a relationship "owns account". The inference engine 2000 processes "Person" as an upstream concept and "Bank Account" as a downstream concept. The specifics about these concepts, i.e., its notes and functions, are all read from the semantic model and dynamically processed by the inference engine 2000 through its inner logic for inferencing. The depiction of a semantic model in terms of building blocks allows it to be used by any number of domain applications.

Semantic Knowledge Base

As depicted in FIG. 4, the semantic model 1000 is the blueprint of what knowledge is stored in the semantic knowledge base 3000. The inference engine 2000 is responsible for instancing all knowledge stored in the knowledge base 3000.

Figure 10:
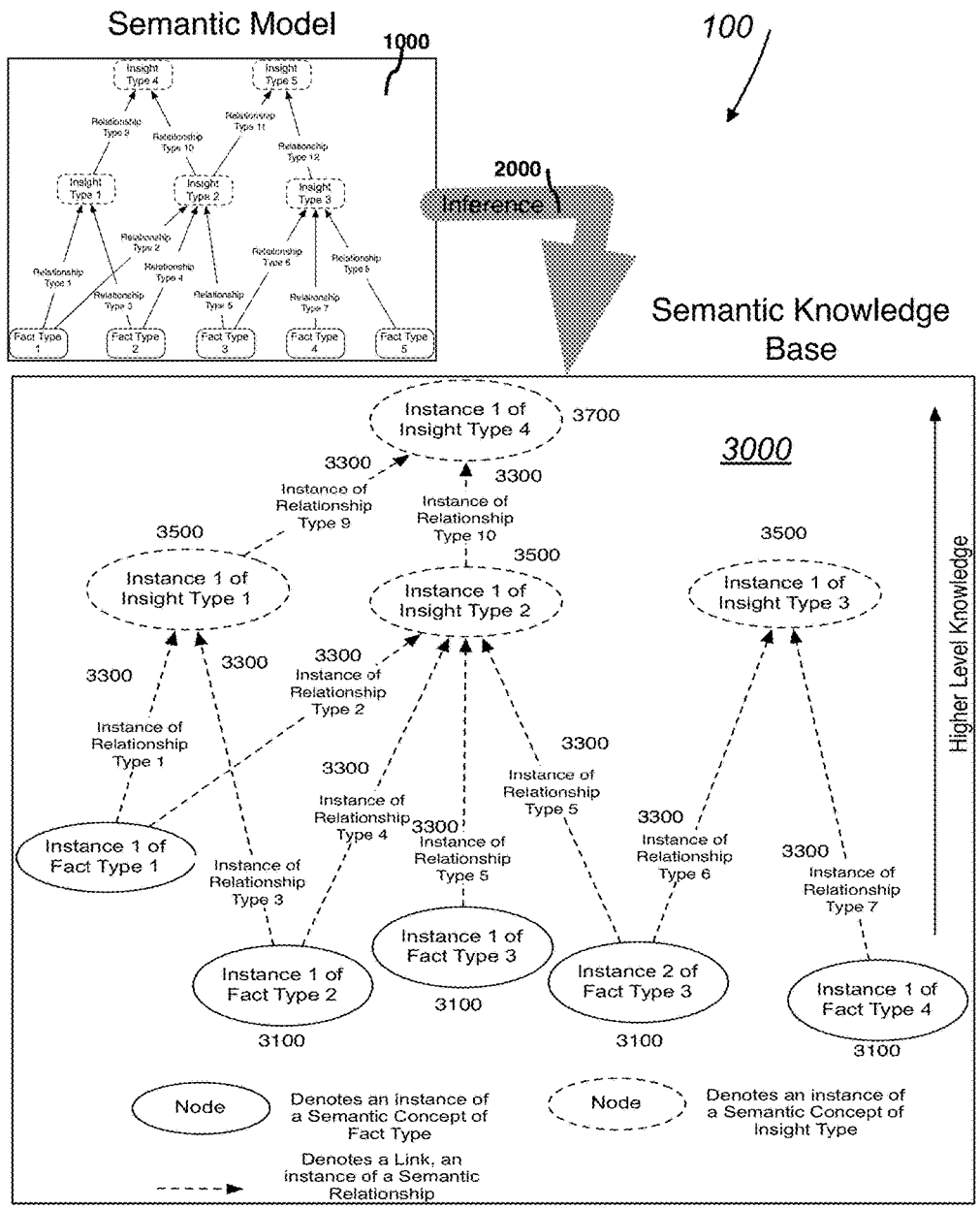
FIG. 10 illustrates one example of inferred nodes and links for the generic semantic model of FIG. 8.

FIG. 10 depicts the general form of a semantic knowledge base 3000. It presents an example of instances of concepts and relationships for the general form of the semantic model depicted in FIG. 8. Corresponding to the fact concepts 1100 of FIG. 8 are the fact nodes 3100 of FIG. 10. Corresponding to the insight concepts 1500 and 1700 of FIG. 8 are the insight nodes 3500 and 3700 of FIG. 10. Links 3300 in FIG. 10 connect all nodes and correspond to relationships 1300 of FIG. 8 among the nodes. All nodes and links are created by the inference engine 2000, through direct knowledge about the world 3100 or through conclusions drawn from the direct knowledge about the world 3500 and 3700.

FIG. 11 is an example of a specific semantic knowledge base for the financial transactions semantic model defined in FIG. 9. In this example, there are two instances of the person concept: Bob 3101 and Sue 3102, each owning a bank account. Bob's account 3103 is with City Bank 3105 and Sue's account 3104 is with State Bank 3106. The two accounts 3103, 3104 have had three financial transactions 3107, 3108, 3109 described by two types of links: sends money 3310, 3312, 3314 and receives money 3311, 3313, 3315. For each of these transactions, Bob sends money indicated by links 3310, 3312, 3314 and Sue receives it indicated by links 3311, 3313, 3315. The nodes 3101-3109 are all instances of fact concepts, known through external data sources. Multiple types of inferences occur as soon as the fact nodes are instanced. In one type of inference, new links are created between existing nodes. For example, in FIG. 11, link 3307 is created between Bob 3101 and Sue 3102 to indicate that Bob and Sue transact money. A second type of inference sets attribute values in existing nodes. For example, the creation of a bank account node or a link to it automatically triggers the running of specific functions defined with the bank account concept that calculates the account balance attribute. A third type of inferencing determines if the creation of upstream fact nodes prompts the creation of downstream inferred nodes. FIG. 11 depicts three examples of inferred downstream nodes 3501, 3503, 3504. Nodes 3501, 3505, 3506 are prompted by the creation of each transaction 3107, 3108, 3109, respectively, between Bob's and Sue's Bank Accounts 3103, 3105, respectively. The first instance of concept type "Personal Transaction" 1501 in FIG. 9 between Bob and Sue, 3501 triggers the creation of an instance 3701 of the concept type "Transactional History" 1702 shown in FIG. 9. Each subsequent personal transaction 3505, 3506 creates additional links to node 3702 which tracks the history of personal transactions between Bob and Sue to infer who primarily sends money 3320 and who primarily receives it 3321. Other examples of inferred nodes in FIG. 11 include 3502 and 3503 which track Sue's and Bob's spending habits from which the inference engine can predict when an account will need a deposit 3701. The updates to 3503 from 3104 and to 3701 from 3503 are examples of automatic enhancements of semantic knowledge through inferencing that is enabled by this invention.

Figure 12:
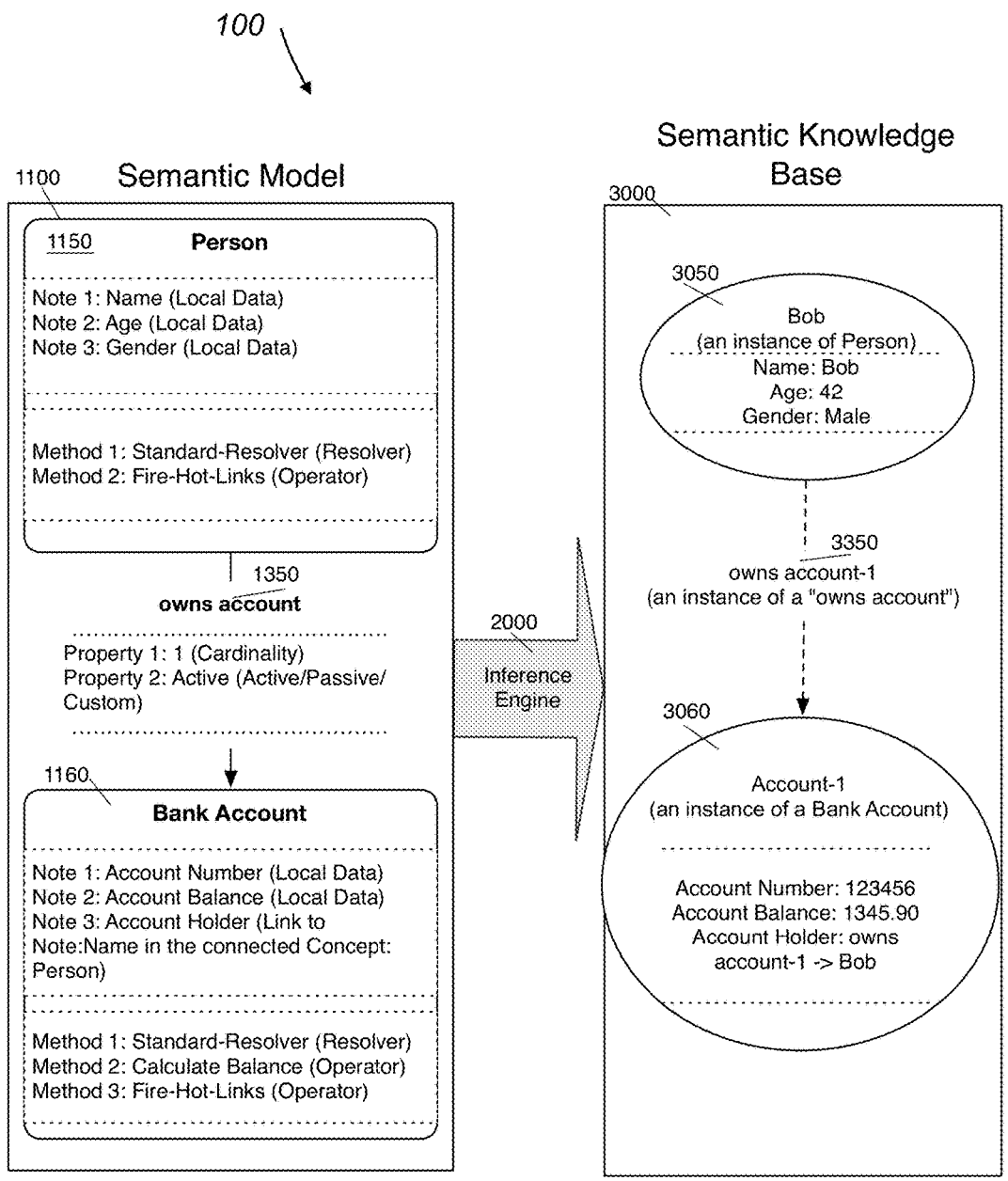
FIG. 12 illustrates an example of an expanded definition of concepts and relationships for the semantic model of FIG. 9 and an associated knowledge base.

FIG. 12 depicts the three different ways that knowledge is represented in the extended semantic knowledge base: nodes represent concepts 1100 defined in the semantic model, attributes represent notes 1200 within concepts and capture data about the node, and links represent relationships 1300 among nodes.

The example in FIG. 12 provides details for two of the concepts defined in FIG. 9: the "Person" and "Bank Account" concepts. The person concept is defined to have three notes: Name, Age and Gender. The corresponding node in the semantic knowledge base represents a person named Bob 3050 in FIG. 12, age 42, male. He owns a bank account 3060 with account number 123456 with account balance $1345.60. Account number and account balance are notes in the bank account concept. The third note in the bank account concept is the account holder. This note is a link to the "Name" note in the upstream "Person" concept.

Inference Engine

Figure 13:
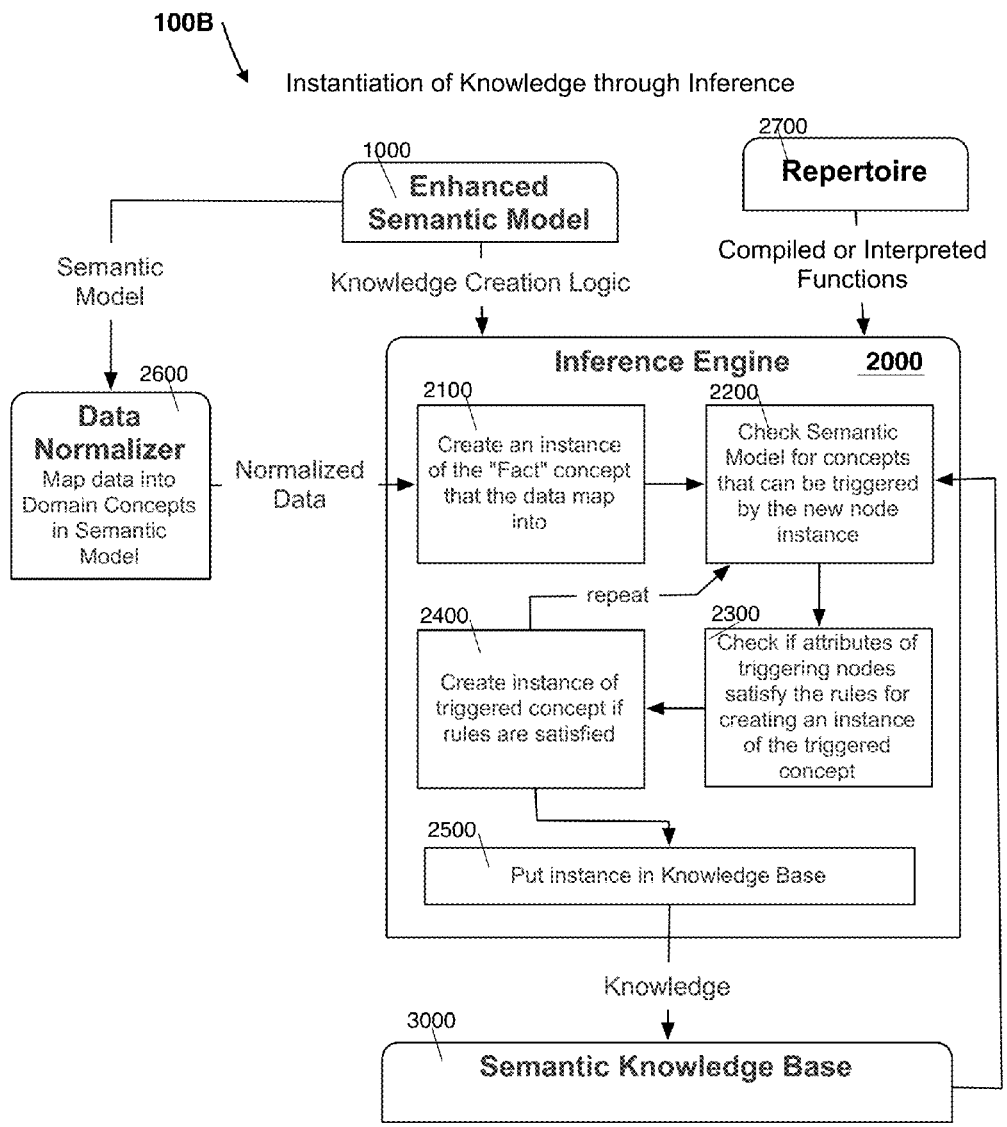
FIG. 13 illustrates the process of creating knowledge.

The inference engine 2000 is responsible for creating nodes and links in the semantic knowledge base as instances of concepts and relationships in the semantic model. FIG. 13 depicts the overall flow of the inference process 100B. The enhanced semantic model 1000 defines the logic for creating instances in the semantic knowledge base 3000. The semantic model identifies the functions to be systematically invoked by the inference engine 2000 during the instancing of a specific concept. These functions, collectively called the repertoire 2700, may be compiled or may be depicted in the meta-language that is interpreted in real time by the inference engine. The ability to code domain dependent functions in an interpreted meta-language means that they remain external to the core inference system and can be added/updated as needed without requiring an update to the software of the core inference engine.

The functions in the repertoire 2700 are of fixed types Resolver, Context Gate, Collector, Qualifier and Operator. Each type of repertoire function has a specific role during the inference process. A repertoire function may be domain independent and thus applicable to a wide class of inference problems. Alternatively, a repertoire function may be applicable only for a specific semantic model for a domain.

The inference process begins with facts about the real world that are normalized to the semantic model 2600 and input to the inference engine. The normalized facts are seed knowledge in the semantic knowledge base 3000.

Whenever any knowledge is created or updated in the semantic knowledge base nodes, links, and attributes, it triggers the cascading of knowledge that is downstream 1002 from the upstream concept 1001 just instanced or updated, as shown in FIG. 4. When a concept is instanced, its downstream concepts or their corresponding nodes are identified and considered for instancing or update 2200. A series of functions defined with the concept in the semantic model 1000 are executed by the inference engine to determine whether conditions for creating new node/link or updating an existing node/link are satisfied 2300.

Figure 14:
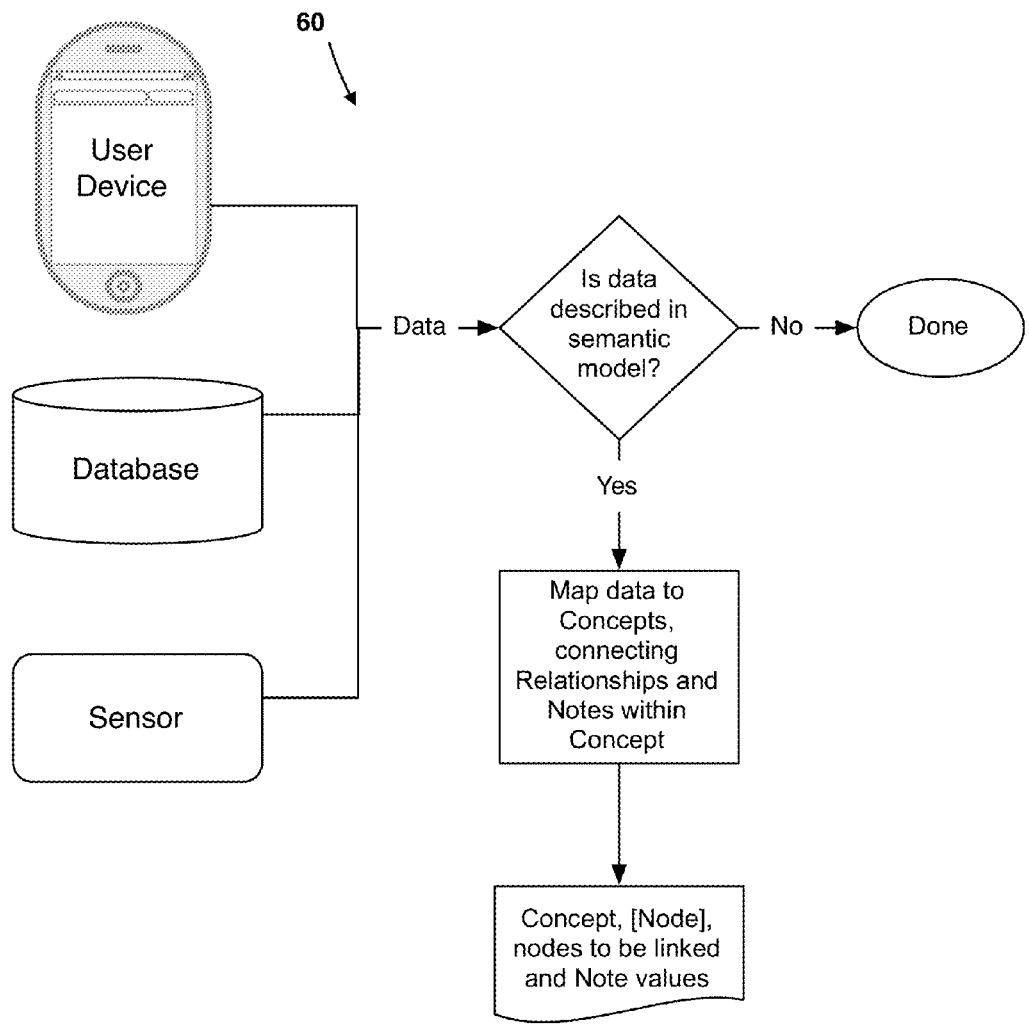
FIG. 14 illustrates the preparation for normalizing data.

FIG. 14 describes the start of the data normalization process 60. In one embodiment, the data normalizer 2600 (shown in FIG. 13) periodically polls all external data sources for new data. Alternately, external data sources could push new data to the data normalizer as they become available. The data normalizer interprets which of the data are described in the semantic model, and those that are not described are ignored. Those that are described in the semantic model are sent to the inference engine as a packet of information that identifies which concept/note/relationship the data correspond to. The inference engine determines if the data are already contained in the semantic knowledge base, and if not, it adds the data to the semantic knowledge base.

Figure 15:
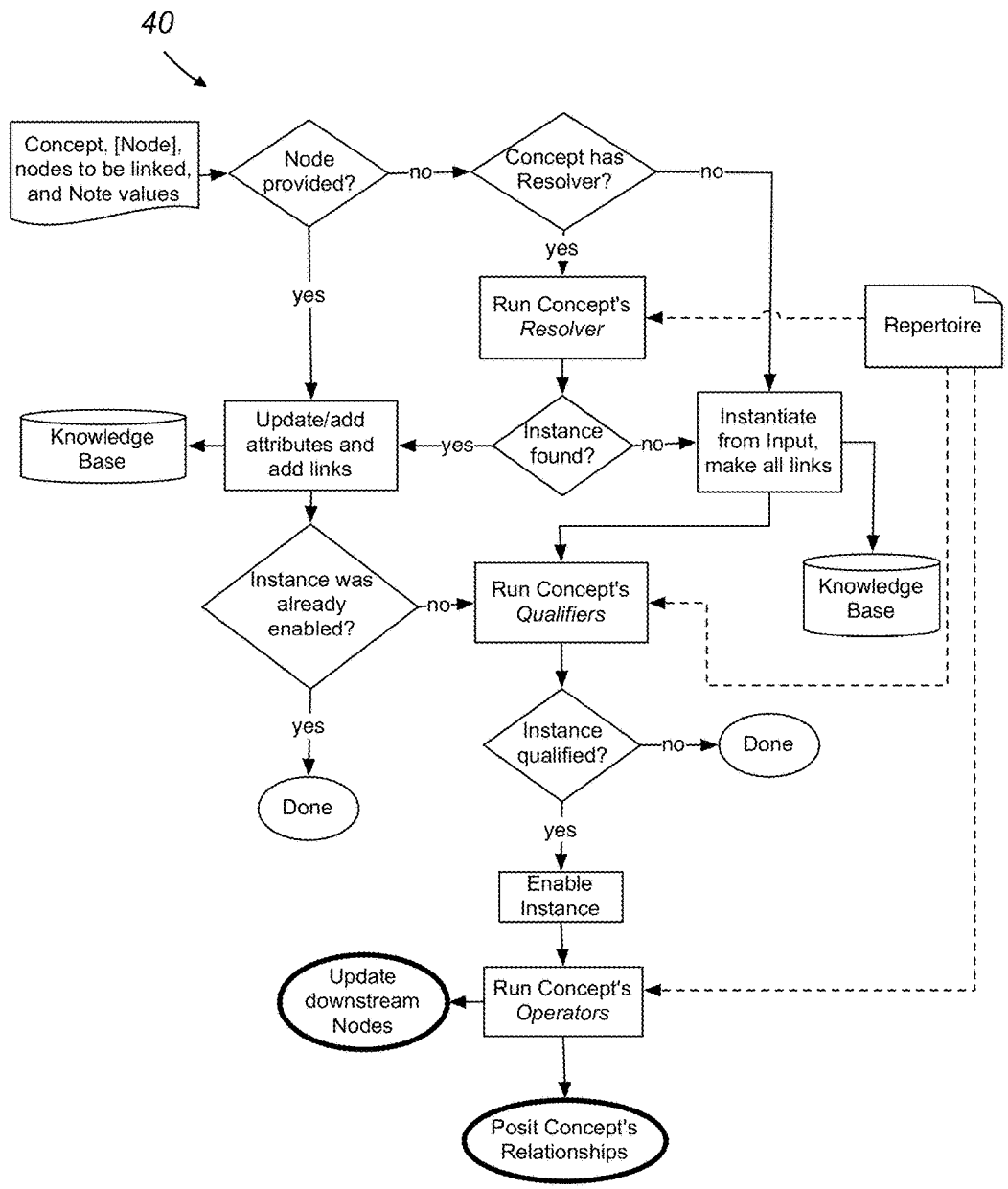
FIG. 15 is a flowchart for the data normalizing process.
Figure 16:
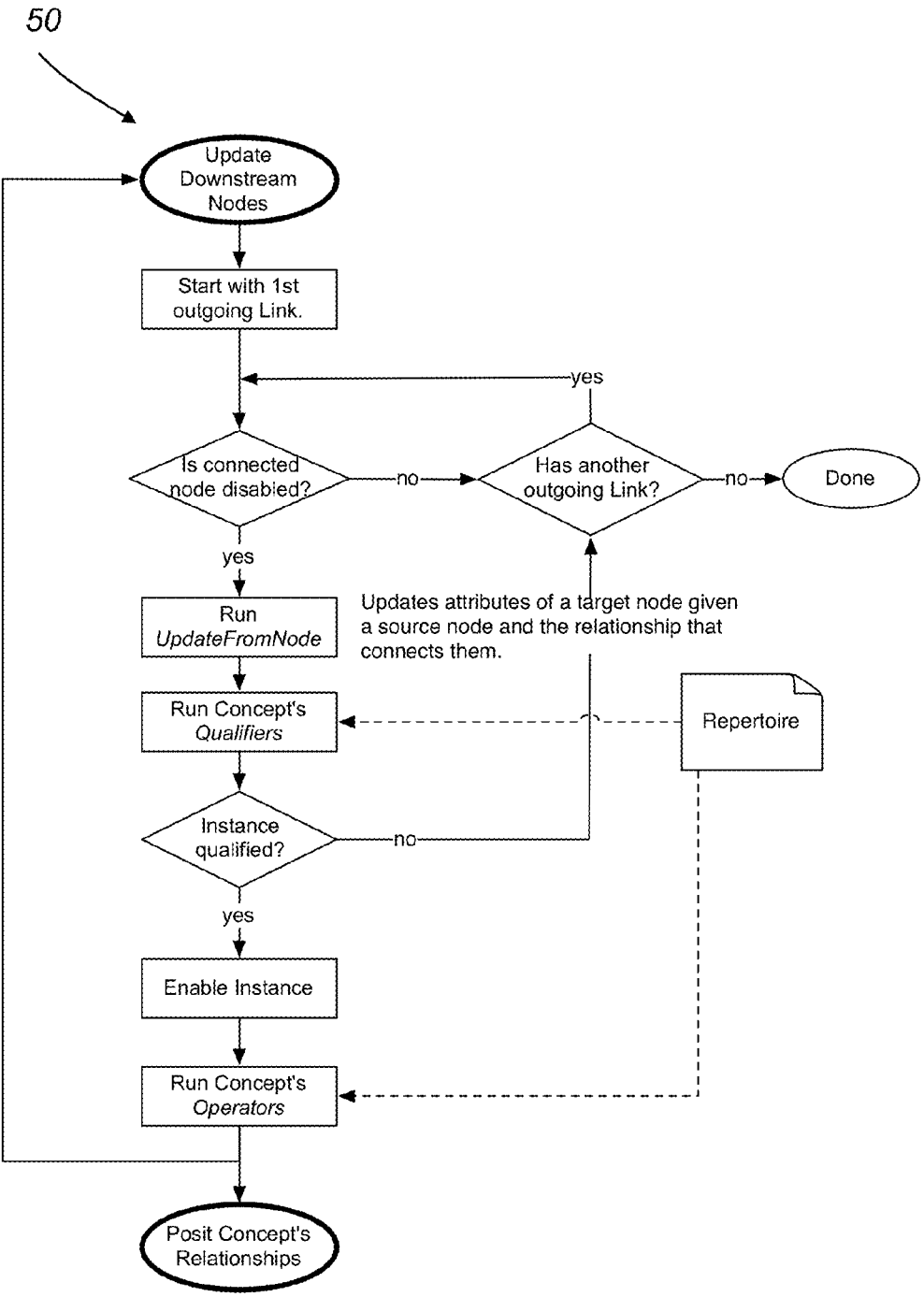
FIG. 16 is a flowchart for the process of recursive updating.
Figure 17:
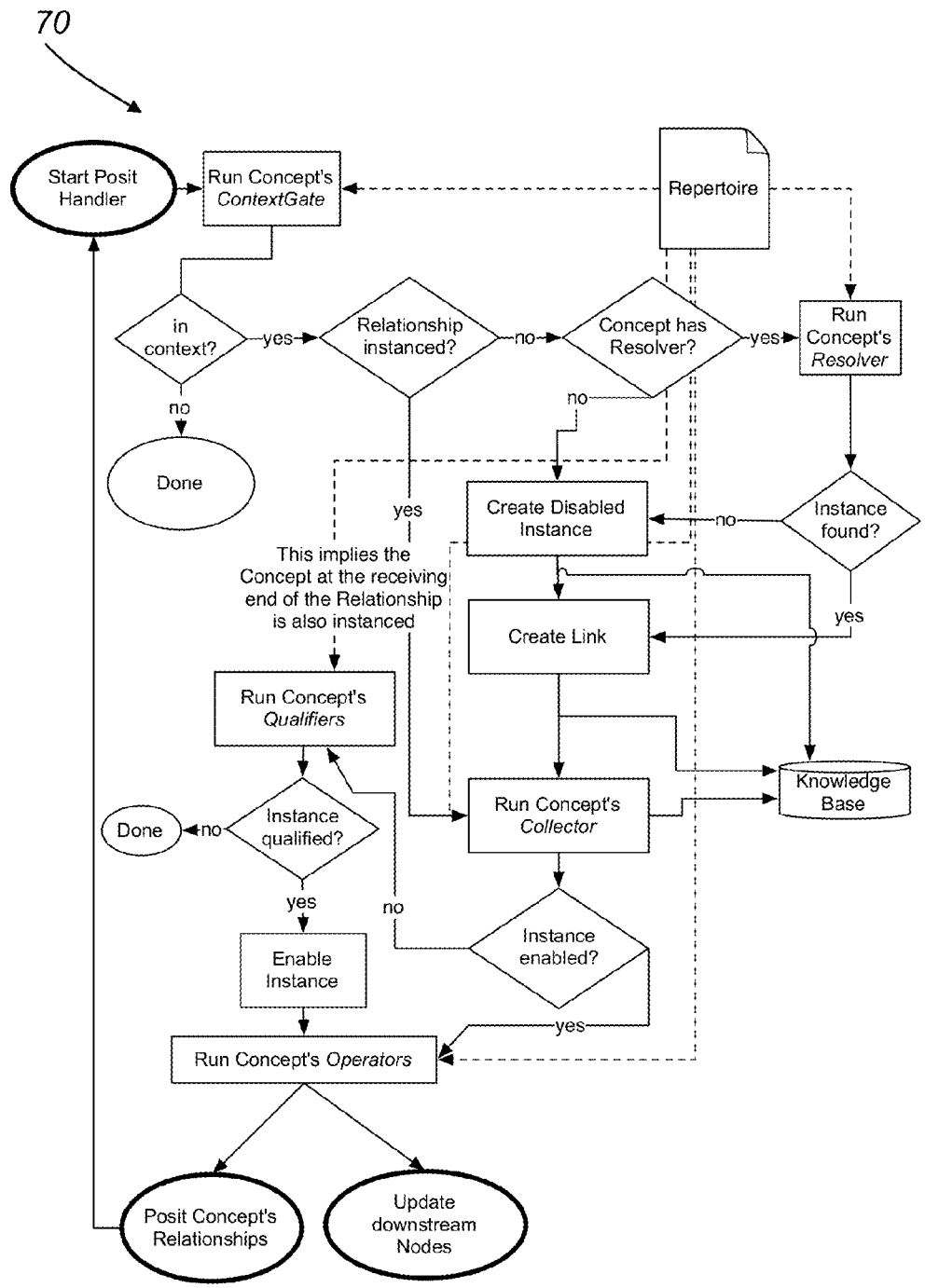
FIG. 17 is a flowchart for creating new nodes and links through inference.

The inference process has three stages: first stage 40—creating instances of fact nodes and associated links, is shown in FIG. 15; second stage 50—recursively updating downstream nodes, is shown in FIG. 16; and third stage 70—instancing downstream insight nodes and associated links, is shown in FIG. 17. The inference process, depicted in FIGS. 15-17, invokes five types of functions: Resolver, Context-Gate, Collector, Qualifier and Operators. These functions are identified in the definition of concepts in the semantic model. The functions are referenced via their index in a library of functions, called the repertoire 2700. The inference engine dynamically accesses these functions, in real time, based on their index in the repertoire.

FIG. 15 depicts the logical flow of the first stage 40 of inferencing: creating instances of fact nodes and associated links. The first step is to check if the fact represents a node that already exists in the knowledge base. If so, new attribute values are added to the existing node instance. If the fact is not already instanced, the inference engine checks whether the fact concept defines a "Resolver" function. The resolver function and its argument define when a new instance of a concept is to be instanced. The most commonly used resolver is the "Standard Resolver". This method checks whether there are any nodes in the knowledge base with the same attribute as the argument for the resolver function, referred to as the "Resolving Attribute". An example of a resolving attribute for a person is a Social Security Number, a unique qualifier. If a node with a resolving attribute exists, then no new instance is required. Otherwise, a new instance is created. If the resolver function does not include an argument, then a new instance of the concept is created every time. After resolving whether a new instance of the concept is to be created or an existing node is to be upgraded, the inference engine runs the concept's "Qualifier" function to determine whether the node should be enabled. Enabled nodes can activate the cascading of knowledge to downstream nodes. Nodes become enabled when conditions stated in the qualifier function, such as having certain values for certain required attributes, are met. Until enabled, an upstream node cannot trigger the creation of downstream nodes. Once enabled, the inference engine runs the concepts "Operator" functions. The operator functions computes the values of the notes defined for the concept, such as "Account Balance" for the "Bank Account" concept 1160, shown in FIG. 12.

In the second stage of inferencing, when a node is newly enabled or updated, its downstream links and nodes are activated. FIG. 16 depicts the logical flow 50 of the algorithm to update downstream nodes. The process updates the node's attributes that depend on attributes in linked, upstream nodes. Once attributes are updated, if the node is not yet enabled, the qualifier function is run again to determine whether the node should be enabled. If enabled, the process to instance downstream nodes are initiated. And finally, the operator function is executed to complete the node update.

In the third stage of inferencing, instances of insight nodes and their associated links are created. FIG. 17 depicts the logical flow 70 of the algorithm for creating insight nodes and associated links. The process starts when a fact node includes an operator function called "Posit Handler" which essentially triggers the process of instancing downstream nodes. The first step in instancing insight nodes is to verify that the attributes in the upstream nodes have values that support the creating of a downstream insight node. This criterion is coded in a "Context-Gate" function defined for the downstream node and is dynamically invoked by the inference engine. The context-gate function returns a Boolean value. If the returned Boolean value is "true", the downstream node's resolver function is invoked. If no node satisfying the resolving criterion exists in the knowledge base, a new node is created and linked to the upstream node that triggered its creation. The new node and its links are stored in the knowledge base. The second step in the third stage of the inference process is to collect attributes for the newly instanced node. Recall that concepts can contain two types of notes: one that directly stores values, and those that link to attribute values in other nodes, as shown in FIG. 12. The "Collector" function collects attributes values from upstream nodes and associates it with own notes. These attribute values are stored in the knowledge base. The third step in the third stage of inference process is to execute the concept's qualifier function to determine whether the node is enabled. Once a node is enabled, its operator functions are executed. If the operator function includes a "Posit Handler", downstream nodes are triggered and the process in FIG. 17 is implemented again for the downstream nodes, continuing the process of cascading knowledge.

Figure 18:
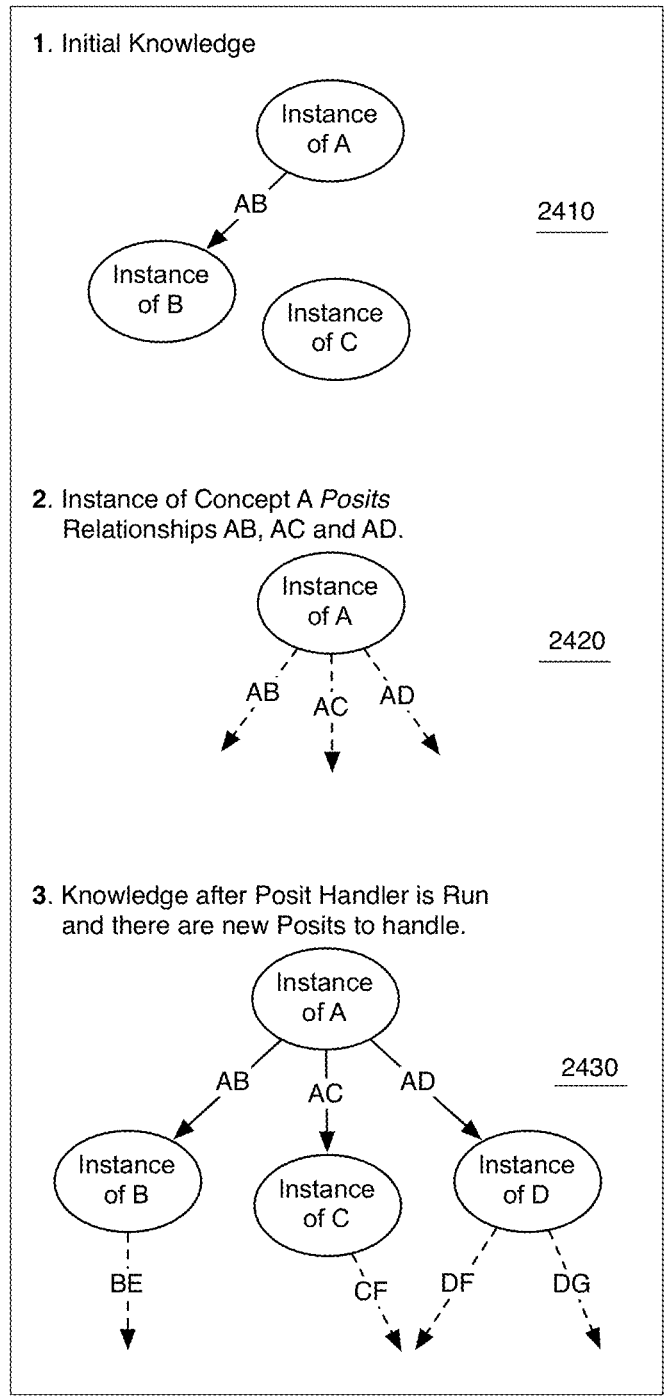
FIG. 18 illustrates an example of positing new relationships.

FIG. 18 illustrates the result of executing the Posit-Handler. Consider concept A with relationships with concepts B, C and D. Let's suppose, to begin with the instance of A had a link to an instance of B. The Posit-Handler operator in A posits that new links may be created between A and C and A and D. The inference process creates a new node D and new links AC and AD. It also activates the already existing node B. The creation/activation of nodes B, C and D triggers the Posit-Handler in Nodes B, C and D, starting the process to create the next set of nodes and links. This cascading process of creating new Insight nodes and associated links is the core of the semantic reasoning method of this invention.

Meta-Language Interface to Inference Engine

The inference engine in the present invention is designed to be applicable to a class of inference problems that can be represented by the semantic model of the present invention. The inference engine reduces the semantic model to its fundamental building blocks e.g. concepts, nodes, functions, relationships and applies its inference logic to the specifics represented by the building blocks. The building blocks of the semantic model and its corresponding semantic knowledge base are described by an extensible meta-language, including a vocabulary of "words" and "syntax" for interpreting words. The words in the vocabulary of the meta-language build upon other words. The meta-language is an extension of the programming language called FORTH. The present invention includes an interpreter for the FORTH language. The interpreter is the interface between the inference engine and both the semantic model and the semantic knowledge base. The interpreter interprets standard FORTH words. In addition, it interprets words that describe the building blocks of the semantic model concepts, notes, relationships, and functions, among others. The interpreter also interprets the semantic knowledge base nodes, attributes, and links, among others. The interpreter also interprets new words in the meta-language that are built upon the abstract words for the building blocks to describe domain specific semantic concepts.

FIG. 19 illustrates the meta-language of the present invention. In this example, "DUP", "IF", "THEN" and "DROP" are fundamental words, defined in a standard FORTH vocabulary. Words such as "SEEK" and "MATCH" are fundamental words needed to describe the building blocks of the semantic model and the semantic knowledge base. "SCAN" is an example of a domain specific word that describes a repertoire function defined for this example. The example also provides a definition of a domain specific query word "TypeNEFriendPhone" that searches the knowledge base and returns a list of friends in New England. The definition begins with the syntax ":" and ends with the syntax ";". The user interface sends a string of words to the interpreter for the inference engine, which can include the dynamic definition of a word, such as TypeNEFriendPhone, and the request to execute the word, specified in this example by the string "26^TypeFriendPhone# is FriendOf SCAN". The inference interprets the query and returns the friends of a person designated in the knowledge base by "26". Such an extensible meta-language for interfacing the inference engine to the semantic model has the benefit that the semantic model can be added/updated as needed without requiring software update to the core inference engine software. Without the ability to dynamically define words that depict concepts and relationships defined in the semantic model and queries for nodes and links stored in the semantic knowledge, the present invention will not scale to inferencing about real world problems where concepts change and evolve over time.

The contents of the semantic knowledge base, represented as nodes with attributes connected by links, can be queried through the meta-language of the present invention. The meta-language is flexible and extensible enough to be able to query for anything in the knowledge base: all or some nodes (specified by restriction on attributes) of a certain concept type, attributes of any nodes, and the links to and from any set of nodes. In addition to querying for updated nodes and links, the meta-language can be used to query for all decision support nodes, such as alerts, reminders and recommendations. These decision support nodes are a special type of insight nodes. For each decision support node, the interface does one of three things: notifies the users of new actionable items, increases the urgency for previously notified actionable items which have not been acted upon, or removes the notification if appropriate actions have been taken. This type of intelligent display is possible because the system tracks every user input and automatically adds its implications to the knowledge base.

Figure 20:
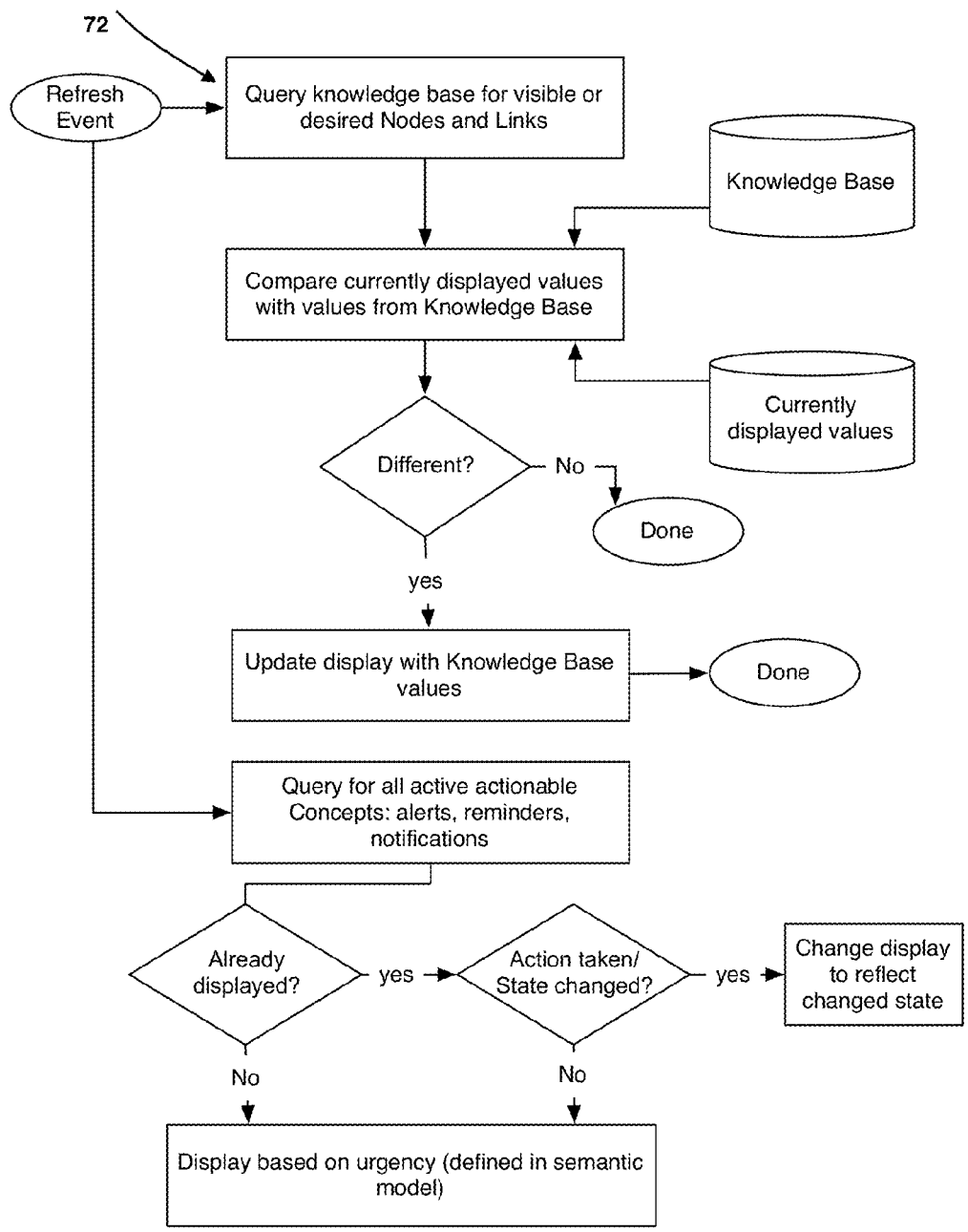
FIG. 20 is a flowchart for the knowledge query process.

An application specific user interface queries the semantic knowledge base and provides decision support to the user. FIG. 20 depicts the flowchart 72 for updating the user interface. At a refresh event, which may be periodic or driven by a user action, the user interface queries the knowledge base for the current values for all the knowledge that is currently displayed. The interface compares the query returns to currently displayed values and updates as needed.

Figure 21:
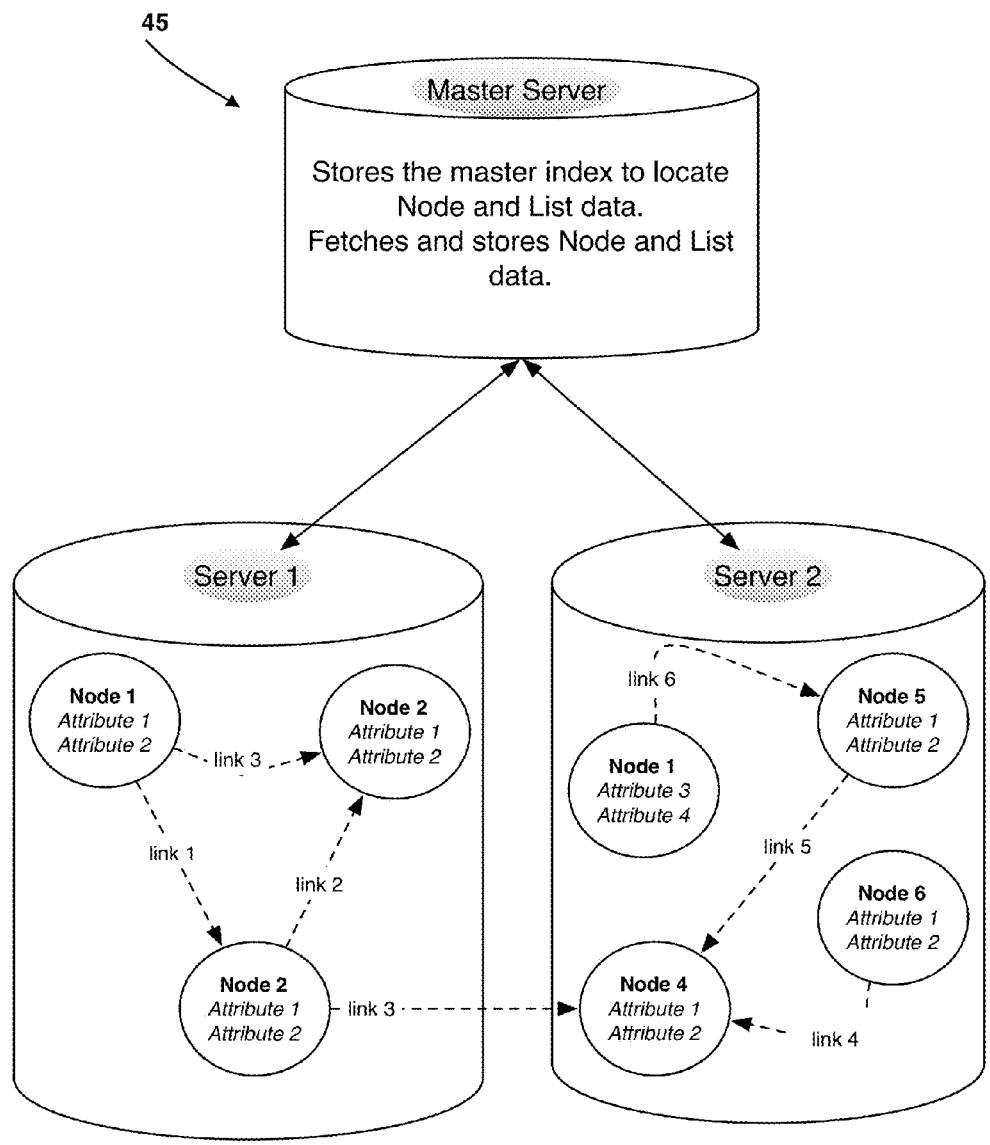
FIG. 21 is an example of a distributed knowledge base.

The knowledge contained in the knowledge base can be stored in multiple computer servers. FIG. 21 illustrates one embodiment of a distributed knowledge base. One server acts as the master containing the address where each node, attribute and link in the knowledge base is stored. When the knowledge base is queried as depicted in FIG. 20, the software service locates the queried node, its attributes and its associated links in the distributed servers, compiles then into the form that answers the query and returns it to the user interface.

Applications of Semantic Reasoning

Figure 22:
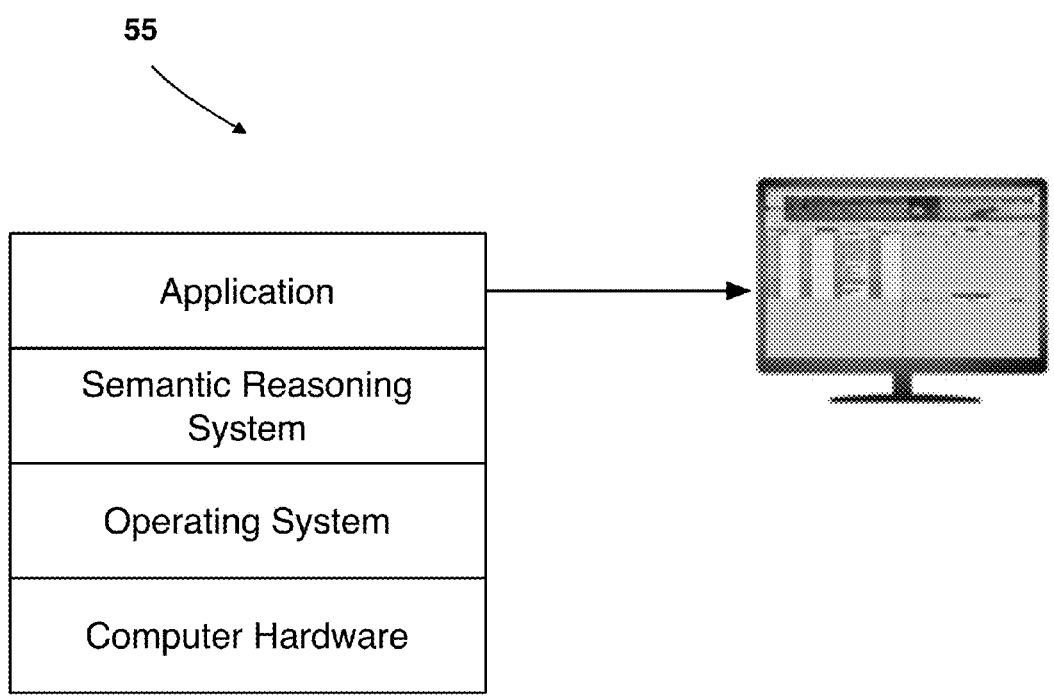
FIG. 22 illustrates a computational configuration for implementing the semantic reasoning system.

FIG. 22 depicts one embodiment of an application of the present invention. The reasoning system is implemented as a set of operating system instructions and is processed by the native hardware hosting the operating system.

Many different application areas are impacted by the ability to extend knowledge in a semantic network through inferencing. Three application areas that are particularly addressed by the present teachings are: 1) automating processes based on inferring what process steps have already been taken; 2) situational understanding derived from iterative analyses and learning of patterns from routine behavioral data; 3) activating individuals to take the right actions at the right time based on what has been done, what needs to be done and what an individual is capable of doing. These applications require inferences through application of logic as well as pattern learning, a combination that can be accomplished through the system and method disclosed in the present teachings.

In a process automation application, a semantic model defines the cause and effect relationships between the process steps. Inference decides which process steps have been undertaken, which steps can be taken next and automatically triggers the necessary next steps. Upstream concepts describe process steps that are followed by those described by downstream concepts. Data necessary to perform an upstream process are accumulated from the downstream (preceding) processes. The Resolver and Context-Gate operators defined within a concept check whether the constraints for implementing the process step have been satisfied. The Collectors and Qualifier operators collect and verify all the data necessary to implement the process step. If all constraints are satisfied and all data are available, the process is initiated. Data that result from the initiated process provide the input to the inference engine and are processed as specified in the semantic model.

In a situational understanding application, data from a range of sensors and user inputs are analyzed to detect situations of interest. The semantic model describes the input data and how they are interpreted to detect the presence or absence of situations of interest. Inference decides whether data necessary for interpretation are available, automates the process of acquiring necessary data and implements the logic for determining the presence or absence of situations of interest. Without inferences, each of these steps requires human intervention.

In a behavioral activation application, the semantic model extends process automation and situation understanding to include formulating recommendations to users. The semantic network defines responses to specific situations of interest. When situations of interest are detected, as in a situational understanding application, inferences formulate response options, based on the characteristics of the situation. Without inferencing, formulating options for response becomes a human function.

FIG. 23 presents the overarching approach for all applications of the present teachings. Data are interpreted for context. The context indicates the situation to which a response is needed, whether an automated response or human intervention. The situation dictates the response. The semantic model specifies the relationships between data, context, situation and response. Through the association of methods with concepts, the semantic model also specifies inference logic. The inference engine maps the data to concepts in the semantic model and identifies contexts, situations and responses following the logic in the semantic model. All inferences are stored in the semantic knowledge base in the form of instances of concepts and relationships between concepts specified in the semantic model.

Semantic Reasoning for Process Automation—a Financial Transaction Automation System (FTAS)

As an example of process automation, we present an application for automating certain financial transactions. The application, depicted in FIG. 9, FIG. 11 and FIG. 12, describes a system where bank transactions are analyzed to learn patterns of transactions and inferences anticipate when additional deposits will be required. FIG. 9 depicts a snippet of the semantic model. It depicts four fact concepts 1101, 1102, 1103 and 1104 and four insight concepts 1501, 1502, 1701 and 1703. The fact concepts represent people 1101, their banks 1103, bank accounts 1102 and financial transactions 1104. Based on the data represented by these concepts, the inference engine continuously analyses pairwise transactions between two account holders 1501, learns the patterns of transactions between two accounts 1702, analyses spending pattern 1502, and anticipates 1701 and notifies 1302 need for funds. The functions invoked by the inference engine to update nodes 1501 and 1502 are specified in the definition of concepts 1501 and 1502 and are part of the repertoire of functions for the application.

Instances for the facts nodes are created when data about financial transactions are normalized into the knowledge base, as illustrated in FIG. 11. These data seeds the knowledge base with instances of people e.g. Bob 3101 and Sue 3102, their bank accounts and transactions between the accounts 3107-3109. This seed knowledge starts the process of inferring the insight nodes. Each time a transaction occurs, the inference engine updates corresponding spending pattern 1502 and transaction patterns between two individuals e.g. 3501, continuing on to funds needed 3701.

FIG. 12 illustrates details of the semantic knowledge base of FIG. 11. Each instance of a concept in the semantic model includes values for its attributes, such as age and gender for a person 3050 and account balance for bank accounts 3060. The semantic knowledge base also represents links between nodes, such as Bob owning Account-1 3350. The inference engine creates links and sets attribute values based on explicitly known facts (e.g. age, gender) or through inferencing (e.g. account balance).

As is true for any application of this invention, the semantic model for FTAS (shown in FIG. 9) can be extended to include additional concepts, both facts and insights. The inference engine remains the same, regardless of the semantic model, systematically applying the functions described in the semantic model to make any inferences that are possible from available data. Examples of extension to the semantic model include spending predictions and automated fund transfers for anticipated expenses. These extensions require adding concepts to the semantic model and adding associated functions invoked by the inference engine to the applications repertoire.

FTAS illustrates one of the benefits of the present teaching: that large volumes of data can be automatically processed into higher levels of knowledge including predictions (e.g. spending patterns and need for funds). A second benefit is that certain processes, such as fund transfers in anticipation of need, can be automated, providing a valuable service to bank customers. The logic for anticipation and automation are explicitly stated in the semantic model and all outcomes of the inference process can be traced back to the semantic model.

In addition to the semantic model, inference engine, semantic knowledge base, the repertoire of functions, and the external data sources that seed the knowledge base with fact nodes, any application of this invention also includes a user interface that will query the knowledge for contents of interest to the user. For the FTAS application, the user interface will include tables and charts depicting spending patterns, as well as alerts for when funds are needed.

Semantic Reasoning for Situational Understanding: Monitoring Activities of Daily Living (MADL)

As an example of semantic reasoning for situational understanding, we describe a system that interprets movement data, along with self-reported data, to infer whether key activities of daily living (ADL), such as sleeping, bathing, eating are occurring in a normal fashion. The semantic model describes how data are interpreted into activities of daily living. The inference engine continuously applies the semantic model to incoming data to synthesize whether expected activities are occurring, whether there are departures from normal patterns and to draw attention to abnormal patterns.

Figure 24:
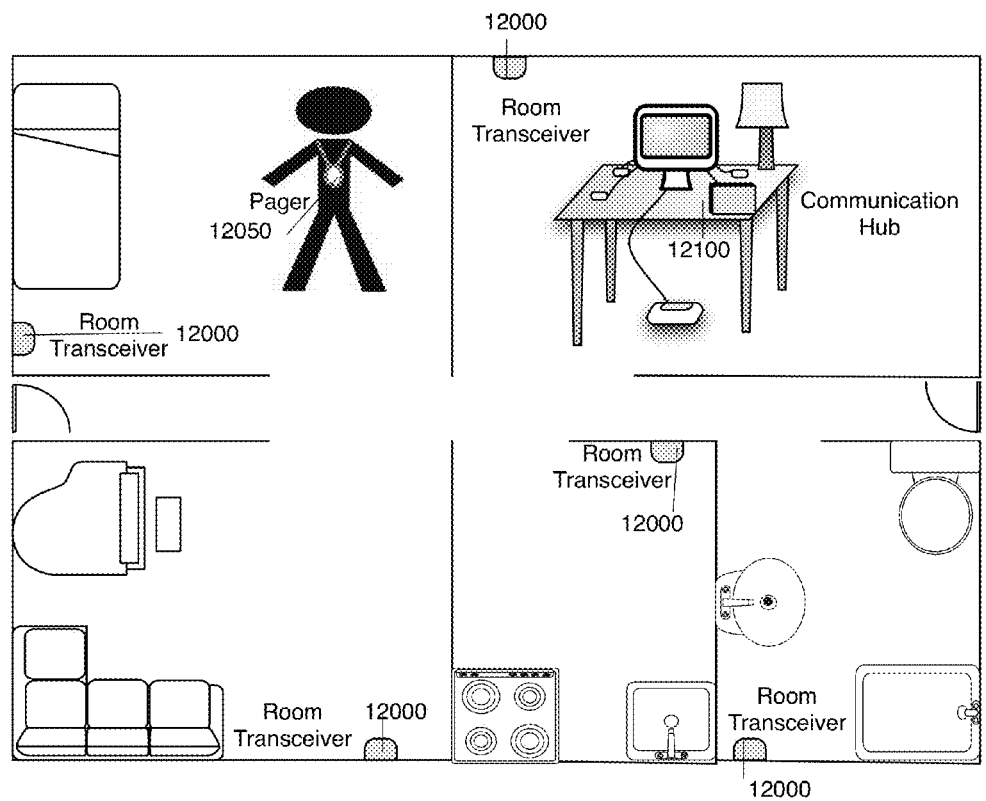
FIG. 24 illustrates one aspect of using sensors within a home to infer activities of daily living (ADL)

The system for monitoring activities of daily living MADL includes a set of sensors, depicted in FIG. 24, that provide movement data. These sensors include a wearable transmitter 12050, also referred to as the pager, which emits a pulse periodically. The pulse is detected by a set of sensors (transceivers) 12000 distributed within the living space. The signal strength of the pulse that is detected by each detector is sent to the inference engine via a communication hub 12100.

Each of the transceivers 12000 in FIG. 24 has a unique address. The data that a transceiver receives from the wearable transmitter 12050 is retransmitted to the communication hub 12100 with the address of the transceiver. The transceivers are also labeled with the room that they are to be located. Based on the location, this rebroadcasted signal from the transceiver is interpreted for activities of daily living. For example, signals from the kitchen are analyzed for patterns that involve small movements around the stove, punctuated by trips to refrigerators and cabinets. As with all applications of the present teachings, the logic for interpreting the signals from the transceivers are specified in the semantic model and applied by the inference engine to interpret the movement data.

Figure 25:
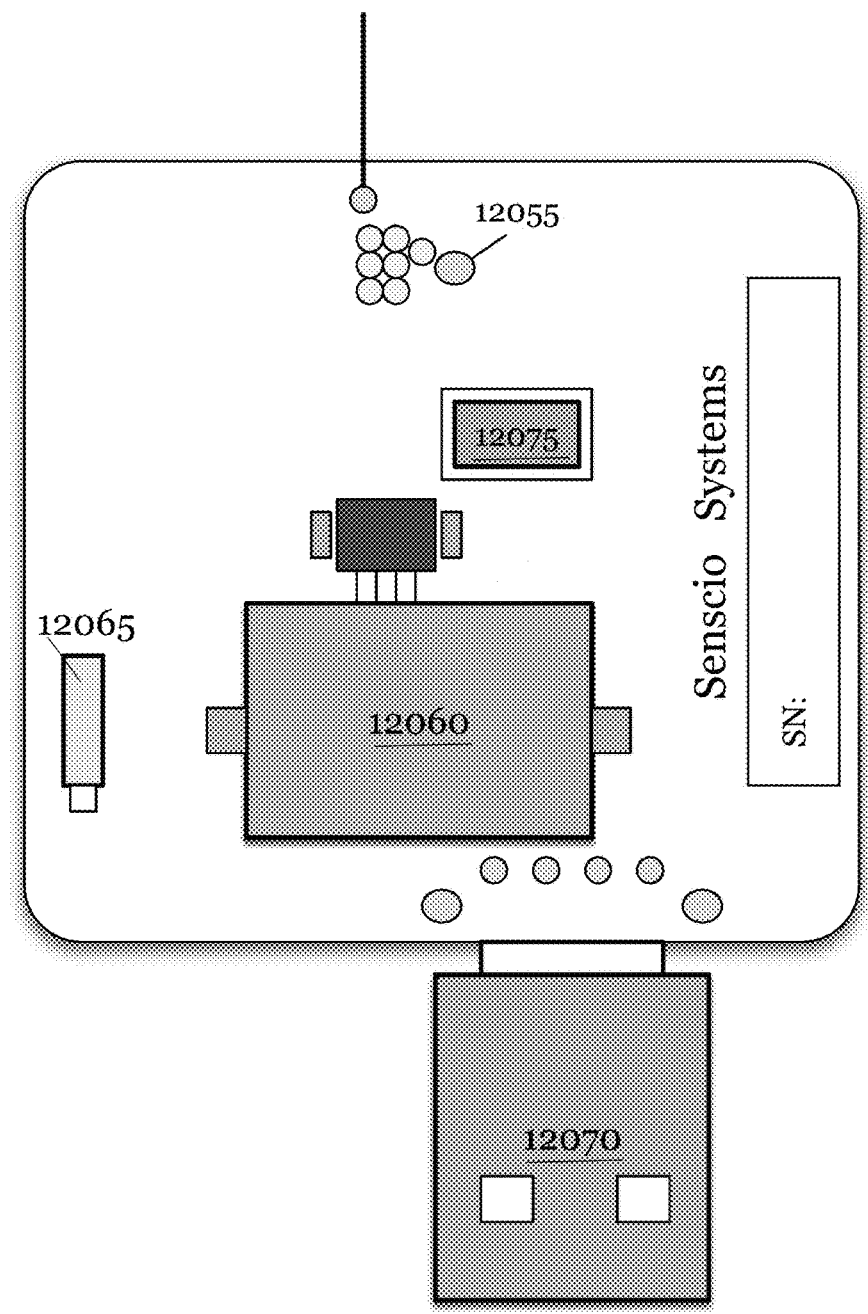
FIG. 25 illustrates a design for a transceiver system used to send and receive RF signals to be used to infer ADL.

FIG. 25 depicts the design of the wearable device 12050. The device includes a single chip transceiver, which transmits a signal periodically, an accelerometer, gyroscope and a magnetometer, a USB connector for charging and an antenna to transmit and receive signals. The transmitters operate in the 420-450 MHz band, the wavelength being long enough to bend around furniture and walls, allowing the transmitted signal to be picked up by multiple transceivers. The accelerometer data allow determination of movement, distinguishing resting from moving. The gyroscope data allows determination of vertical vs. horizontal orientation. The magnetometer allows determination of orientation relation to north. This information is used to adjust for variations in the signal measured by the transceivers that that occur from a person turning towards or away from a transceiver by rotating in place. The sum total of the data from the wearable device includes the signal strength measured by each transceiver, and the data from the accelerometer, gyroscope and magnetometer. Collectively, these data are analyzed by the inference engine to learn repeated patterns of movement in and around the house. Relative signal strengths measured by the transceivers, corrected for the rotational orientation derived from the magnetometer data, are processed to learn when the user is in various rooms in the house (i.e., kitchen, bathroom, bedroom, dining room, living room) and whether, when and for how long they are engaged in activities of rest (i.e., sitting, lying, standing) as inferred from the gyroscope data or motion as inferred from accelerometer data. The room where the activity occurs provides the context to interpret what the activity was. For example, sitting in the dining room after activities in the kitchen indicates eating whereas sitting at the table without surrounding activities in the kitchen indicates work. Such common sense logic is part of the semantic model.

Figure 26:
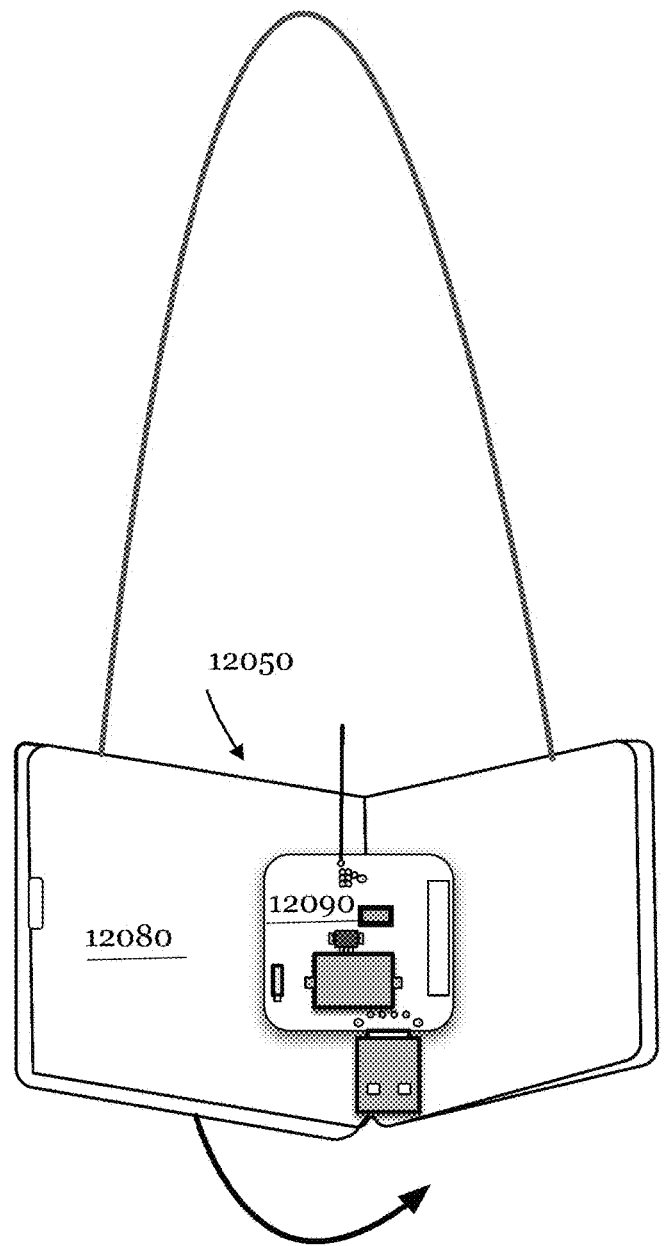
FIG. 26 illustrates an embodiment for accessorizing the wearable RF transmitter of the sensor system for inferring ADL.
Figure 29:
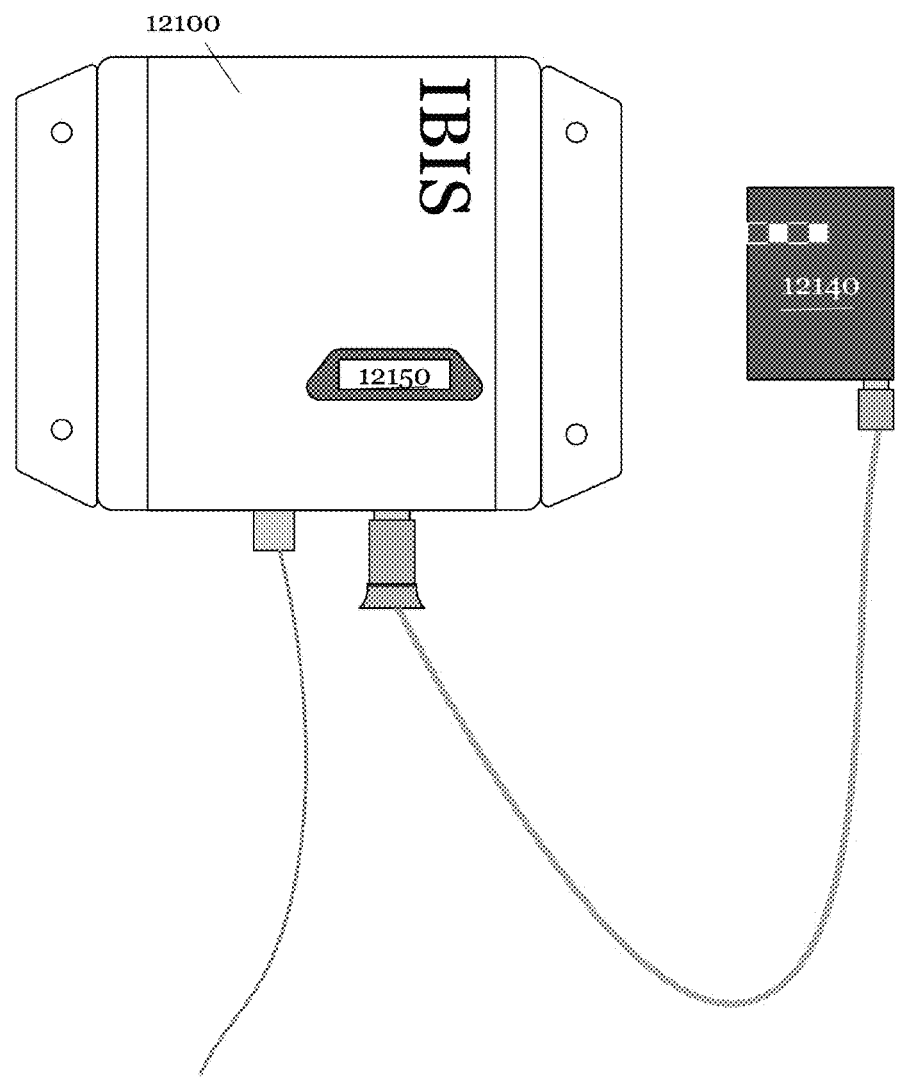
FIG. 29 illustrates that the communication hub of FIG. 28 that powers the wearable RF transmitter, is in turn powered through a USB charger and is connected to the Internet via an Ethernet connection.

FIG. 26 depicts one concept for wearing the pager 12050. The circuit is enclosed in a casing that can work as the ornament in a bolo neckwear. The about 6 inches long antenna can be woven into the bolo lace. An alternate concept is to place the pager on a fabric wristband made of elastic material. The long antenna can be woven into the wristband. FIG. 26 also depicts the battery for the wearable pager. It provides at least a day's worth of power to the pager. The pager can be charged through a USB connector, regular or mini. The communication hub 12100 hosts a dock 12140, as shown in FIG. 29 for charging the pager. The dock includes a guide for the USB connector that slides the connector into contact with the charging circuit inside the communication hub.

Figure 27:
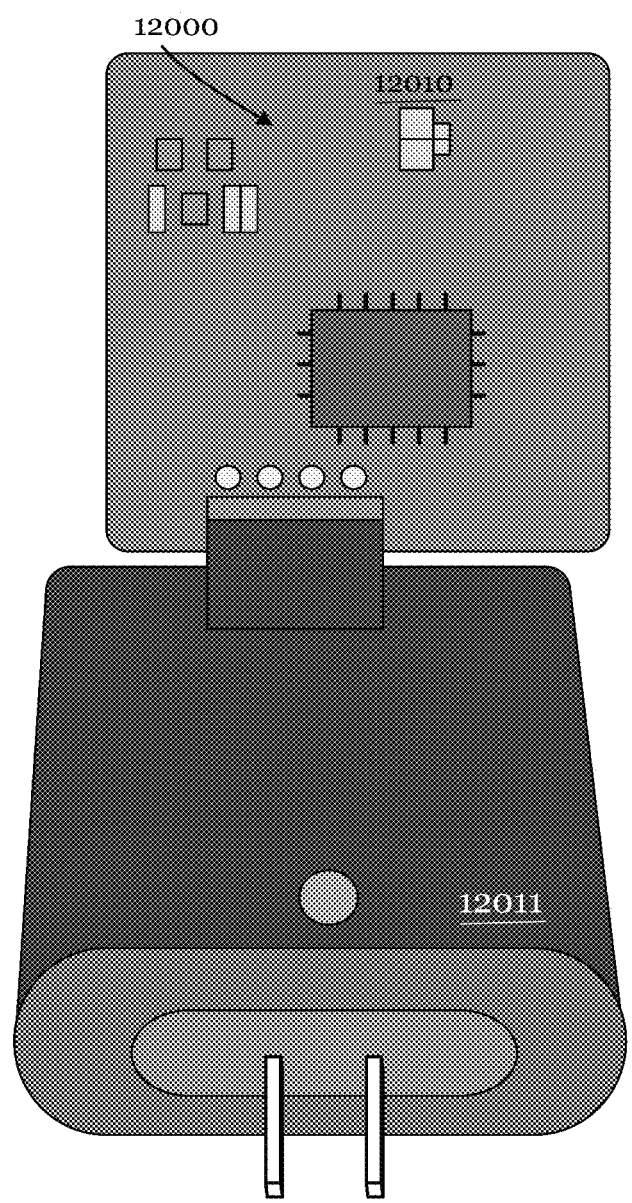
FIG. 27 illustrates that the RF transceivers are powered through a standard USB charger connected to a wall socket.

FIG. 27 illustrates the two components of the transceivers 12000: a circuit 12010 including a single chip that is both an RF receiver for receiving the signals from the wearable pager and a transmitter for rebroadcasting the signal to the communication hub 12100. The circuit 12010 docks onto a wall charger 12011 that provides power to the transceiver.

Figure 28:
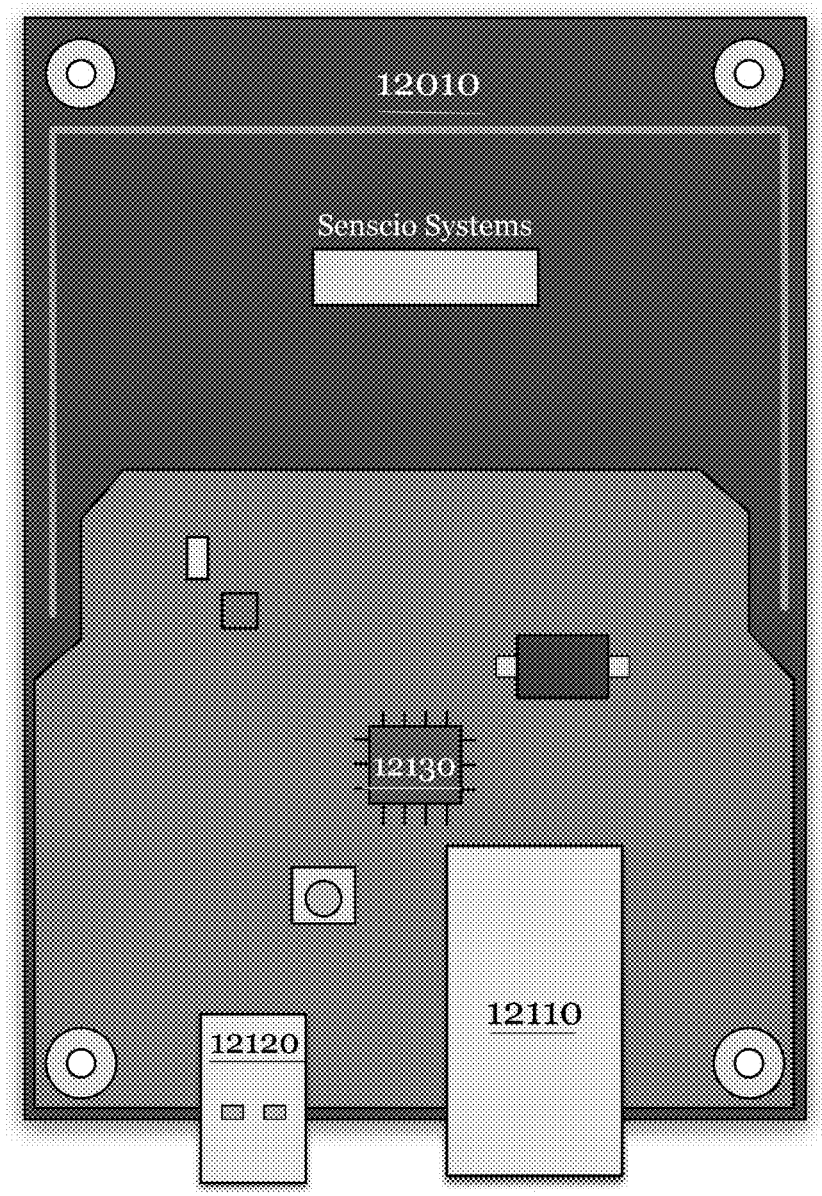
FIG. 28 illustrates a design for the communication hub for the sensor system for inferring ADL.

FIG. 28 depicts the design of the communication hub 12100. The hub includes the same RF receiver-transmitter chip 12130 as in the pager and the transceivers. The hub also includes a CPU, an Ethernet port 12110 and a USB port 12120 for charging the hub. FIG. 29 depicts the communication hub in an enclosure, showing the charging dock 12150 and the Ethernet and charging ports 12140. The Ethernet port transmits partially processed data to a remote server for further processing. The server hosts the semantic model, the inference engine and the semantic knowledge base of the present invention.

Figure 30:
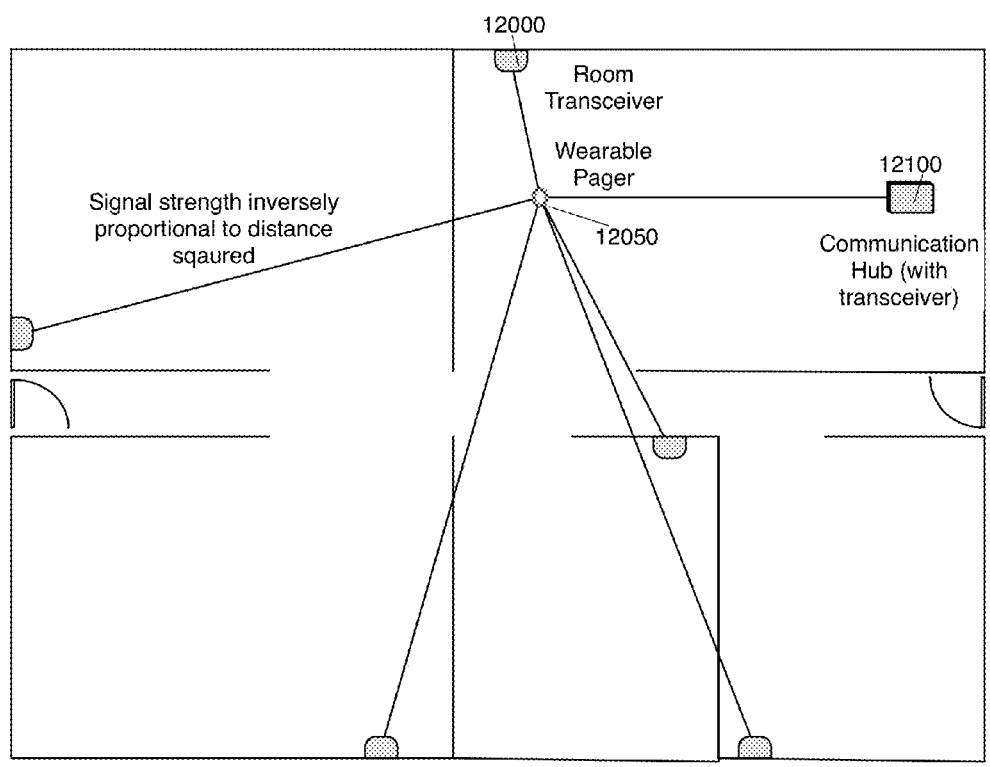
FIG. 30 illustrates one aspect of processing signal strength from a pager as received by transceivers, to locate a care recipient within a home.
Figure 31:
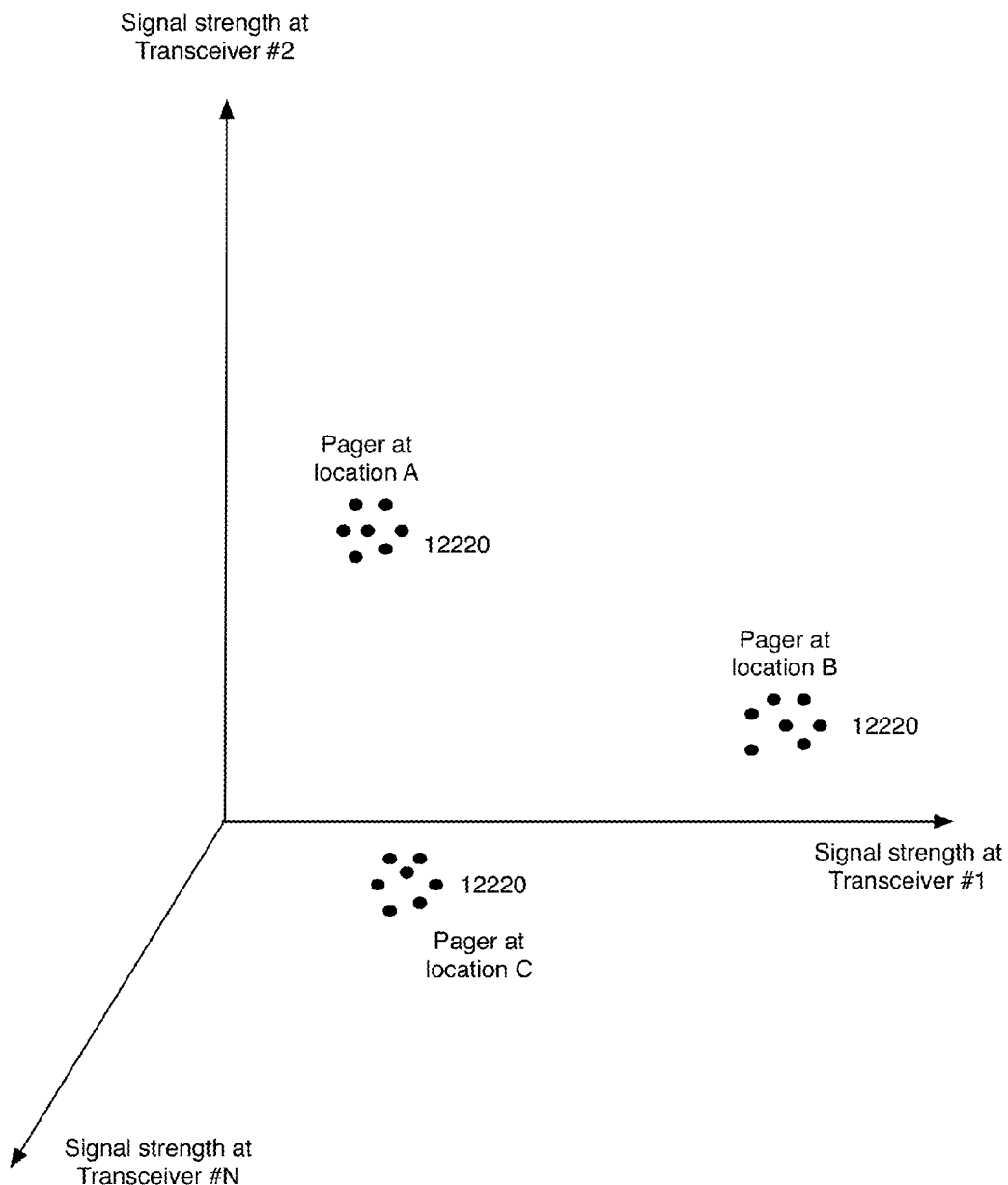
FIG. 31 illustrates using a clustering algorithm on signal strength data to locate a care recipient within a home.

The pager 12050, the transceivers 12000 and the communication hub 12100 are designed to produce, collect, process and relay movement data for interpretation. The interpretation begins with learning patterns of data that are repeated every day and multiple times within a day. These patterns correspond to common activities. FIG. 30 depicts the signals that are received by the transceivers in FIG. 24. Each transceiver receives a signal from the wearable device. The signal strength is inversely proportional to the square of the line-of-sight distance between the wearable device and the transceiver. At any given time, the collection of signals received by all the transceivers within the home form a signal-vector with as many components as there are transceivers. Within the error bounds in the signal strengths, a signal-vector is associated with the location of the wearable device. Regularly frequented locations within the home are represented by a close cluster of signal-vectors, as depicted in FIG. 31. By correlating the signal-vector clusters with self-reported data, such as a meal being taken, as well as movement data recorded by the wearable device, such as no movement, the inference engine is able to associate the clusters of signal vectors with key activities of daily living.

Figure 32:
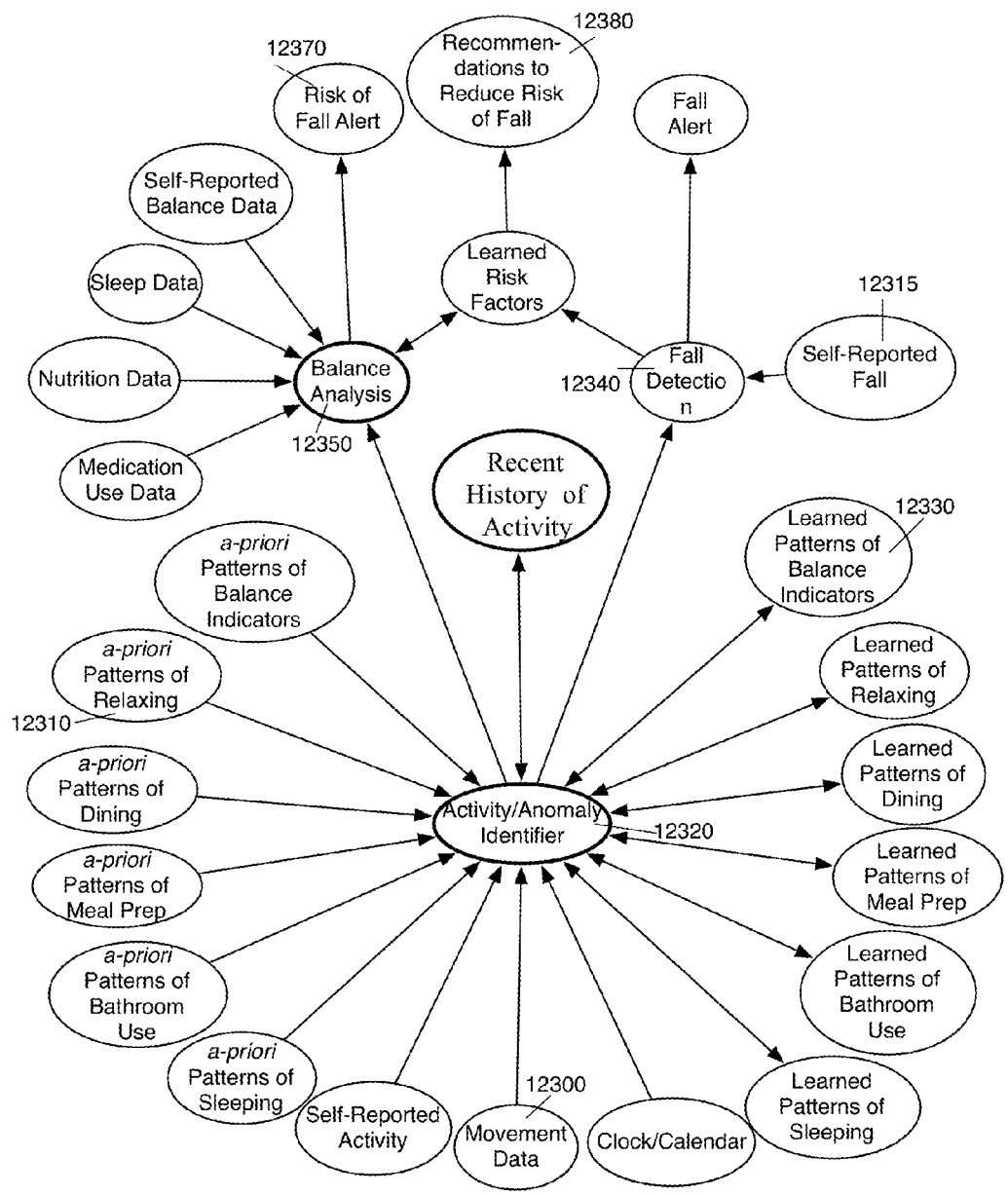
FIG. 32 illustrates inferring activities of daily living from a sensor set in FIG. 24.

Partially processed movement data, i.e. clustered signal vectors are transferred to a server for further processing. FIG. 32 depicts a portion of the semantic model that processes the sensor data into deep insights. In FIG. 32, 12300 depicts the clustered signal vectors transmitted by the communication hub. These data are combined with other data, such as self-reported data about activities of daily living, such as waking up, eating, going to bed, among others. The data are entered as an input to an "Activity/Anomaly Identifier" semantic concept 12320 that identifies and associates repeated patterns with common activities of daily living. A-priori, common sense patterns about common activities are also input to the Activity/Anomaly Identifier concept 12320. Patterns of relaxing, meal preparation, dining, bathroom use, sleeping and balancing 12310 are examples of a-priori knowledge data that are used by the Activity/Anomaly Identifier. Examples of a-priori knowledge data about resting and relaxing include no translational motion, lower than usual center of gravity, and activities occurring for short duration during the daytime following periods of activity. Knowledge about balance specifies patterns such as the presence of a stabilizing period between rising up from a sitting position and starting to walk. Every time data are available from the movement sensors 12300, the inference engine applies all a-priori knowledge that is input to concept 12320 to the movement data to learn the users individual patterns of balance 12330, relaxing, dining, meal preparation and sleeping. Examples of learned pattern includes normal sleep times, normal wake-up times, and normal variations in sleeping routines.

In addition to learning normal patterns of activity, the operator functions for the semantic concept 12320 also identify deviations from normal pattern. For example, the user lying down in an unusual place immediately after walking is identified as a fall 12340. Taking longer to stabilize after sitting triggers a balance analysis 12350, which could result in a high risk of fall alert 12360. Repeated detection of balance issues can trigger the recommendations to reduce risk of fall 12380 such as to rise slowly or to use a cane when rising. All such inferences are automatically generated by the inference engine of the present teaching through the process described earlier in FIG. 15-FIG. 17.

Figure 33:
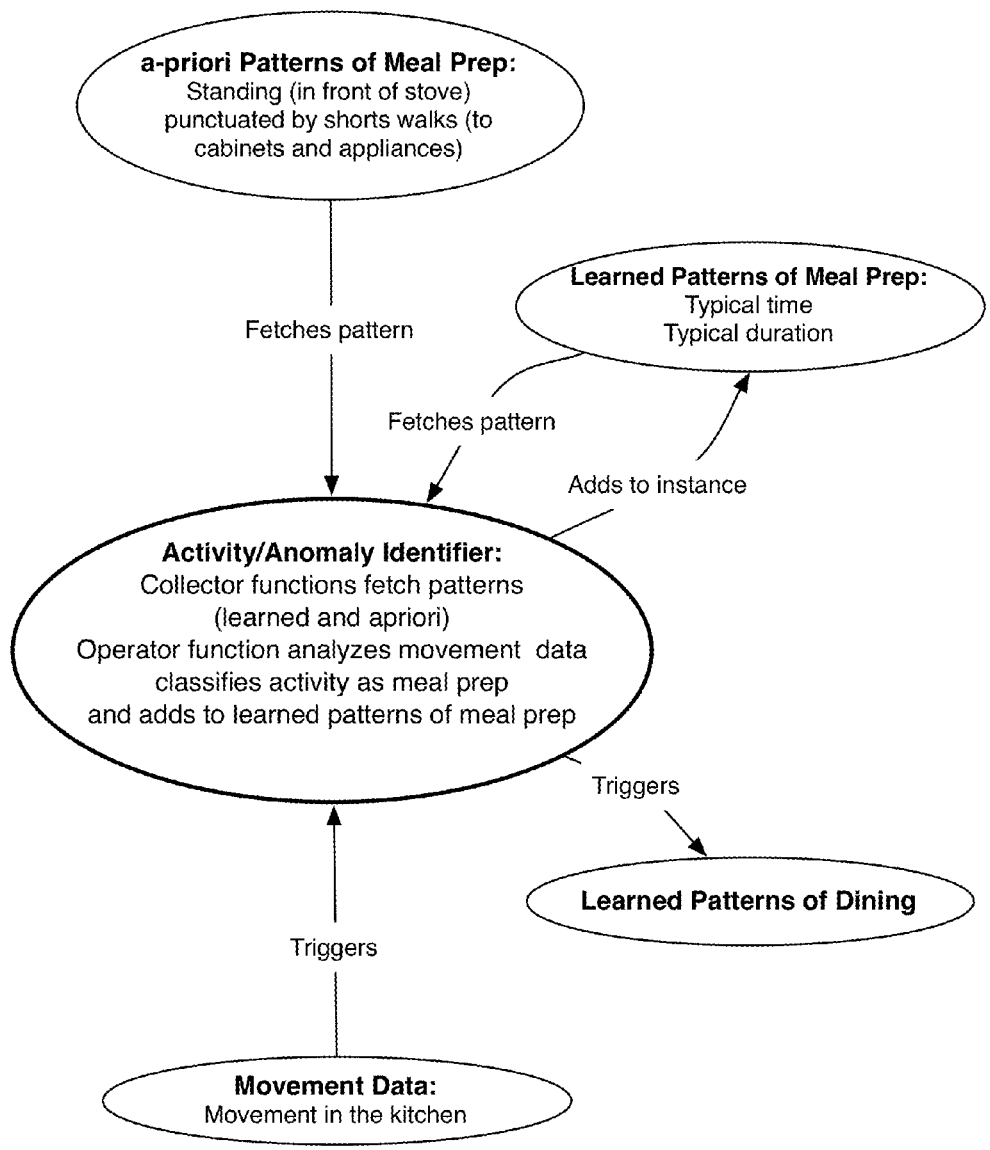
FIG. 33 illustrates the semantic model for inferring activities of daily living.

FIG. 33 illustrates a particular sequence in the inference process. When movement data become available, the Activity/Anomaly Identifier concept is triggered. In this example, the data are about movement in the kitchen. Through the Context-gate and Qualifier functions associated with the Activity/Anomaly Identifier concept, the inference engine determines that it needs to fetch a-priori and learned patterns about meal preparations. Once those patterns are fetched, an Operator function associated with the Activity/Anomaly Identifier concept continues to process movement data until it fits the a-priori and learned patterns. At that point, the movement data are classified to represent meal preparation and are added to the learned patterns of meal preparation. The Operator function then triggers the Learned Patterns of Dining concept to prepare for the processing of an instance of dining.

The processing of movement data as described above converts large volumes of data from multiple sensors (transmitter, accelerometer, gyroscope and magnetometer) assertions about normal and abnormal activities of daily living. The assertions are automatically derived through a process of inference that is explicitly specified through the semantic and hence is explicable. The situational understanding gained through the inferencing process illustrates a key area of application for the present teachings.

Semantic Reasoning for Behavioral Activation: Personal Chronic Illness Management System (PCIMS)

As an example of semantic reasoning for behavioral activation, we describe a personal chronic illness management system (PCIMS). The PCIMS is designed to activate a patient and their caregivers to better manage the patient's chronic illnesses. PCIMS schedules care activities, monitors the scheduled activities, accesses the quality of health and the quality of the adherence to the prescribed care plan, identifies issues and prompts for corrective actions.

Figure 34:
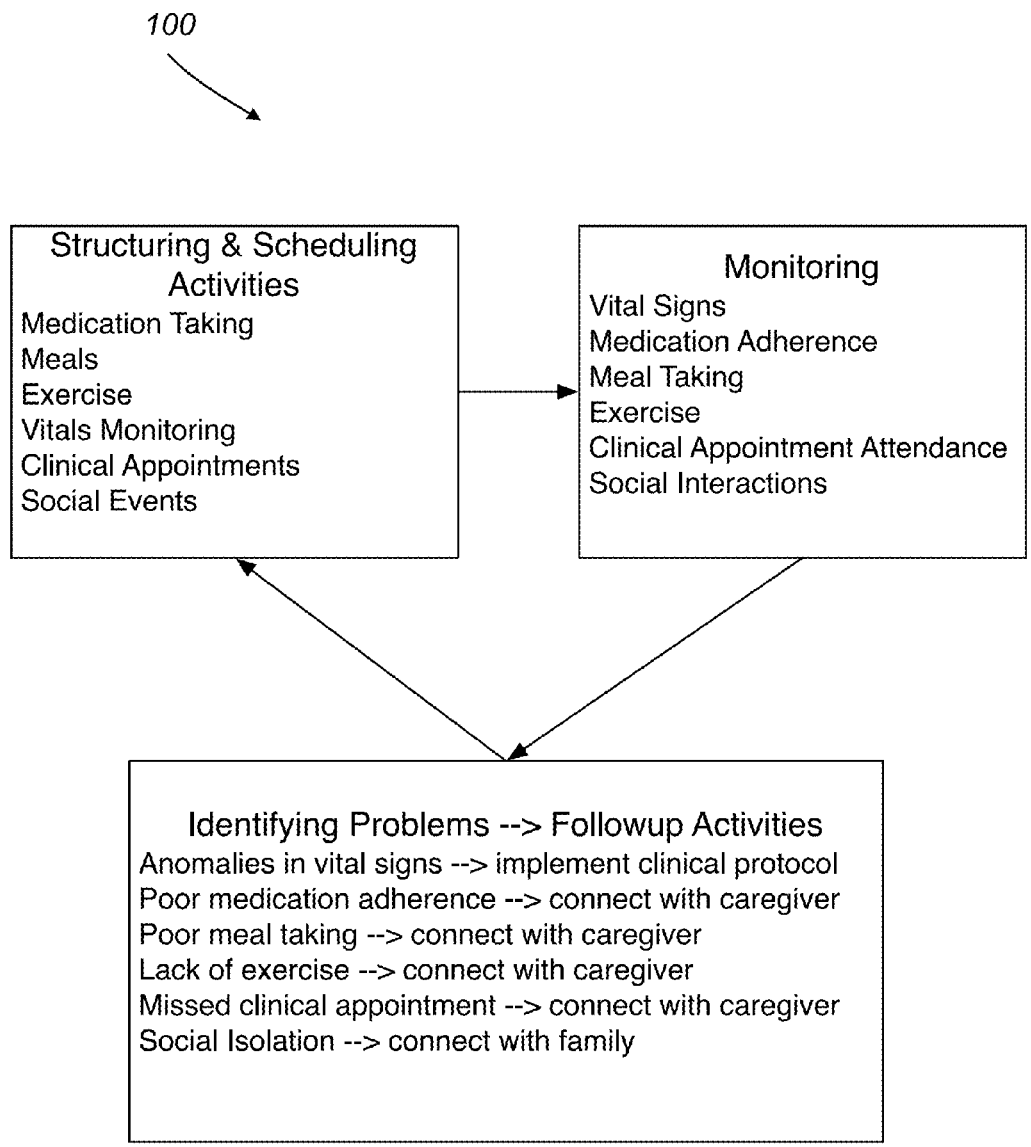
FIG. 34 illustrates three aspects of behavioral activation, which is an application of the present teachings.

FIG. 34 depicts the overarching process of behavioral activation. It includes three phases: 1) activities dictated by the situations are structured and scheduled; 2) activities are monitored and data from the activities are analyzed; 3) issues are identified and remedial actions are activated. The three phases repeat continuously. Examples of steps within the three phases of behavioral activation for chronic illness management are shown in FIG. 34. The three phases include many steps than can be consistently performed by people and automation through inferencing is necessary.

In the PCIMS application, behavioral activation is automated through the semantic reasoning approach of the present teachings. Behavioral activation begins with structuring and scheduling activities. PCIMS structures the following types of activities: medication taking, meal taking, exercising, vitals monitoring, following up with physicians and interacting with family. PCIMS processes data such as the patient's physiology, medication adherence, diet, exercise and clinical follow-up to monitor the response to the structured activities. Included in the monitoring is making inferences about the quality of adherence to the prescribed care-plan, physiologic response, recognition of where help with care is needed and seeking of help from those that can provide it. Through inferencing, issues with self-care are identified and intervention strategies are devised. The intervention strategies are scheduled as structured activities and the process of behavioral activation continues in a loop.

Figure 35:
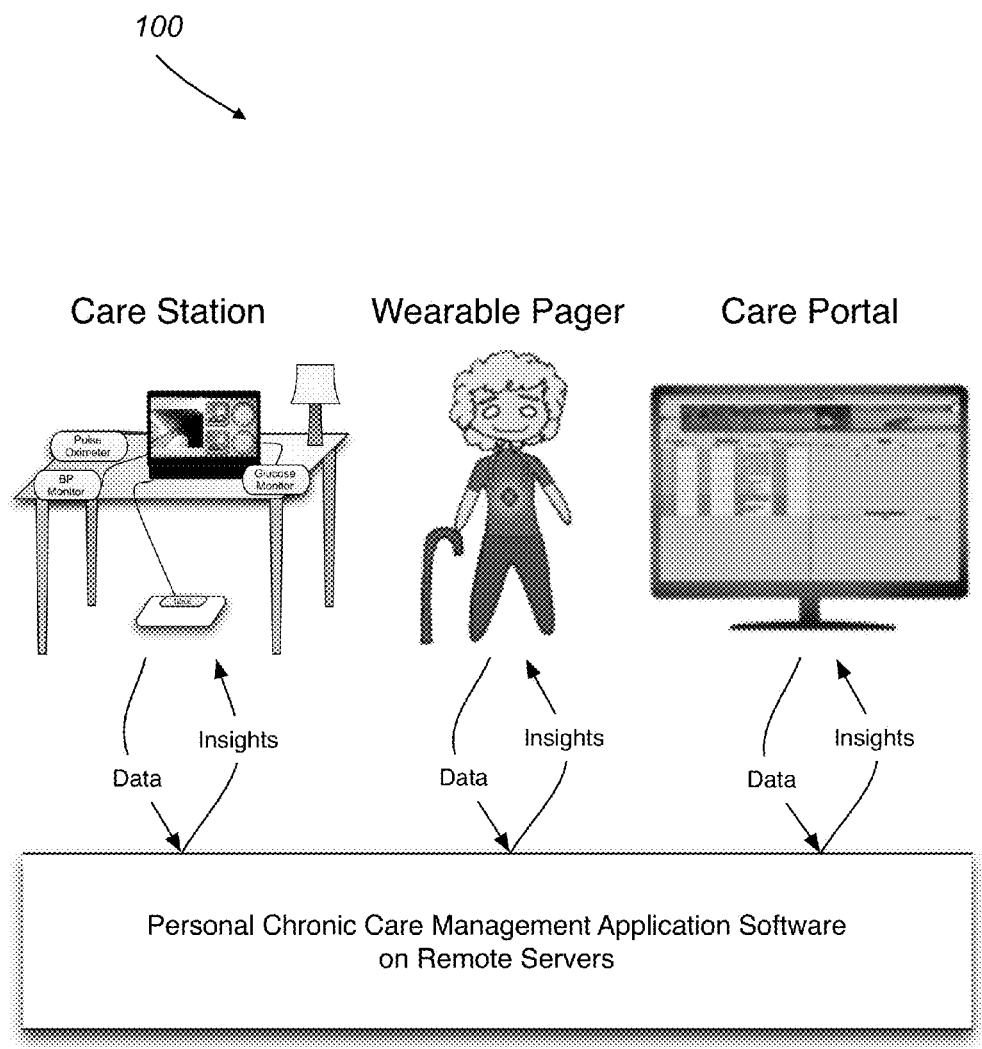
FIG. 35 illustrates one example of a personal chronic illness management system (PCIMS)

In one embodiment of the PCIMS, the system includes the components depicted in FIG. 35. The Care-Station, the Pager and the Care-Portal are all interactive devices through which a patient and caregivers sends data to the inference engine and receives query results from the semantic knowledge base. The Care-Station interface takes inputs from and provides decision support to the patient. The Pager is a wearable device that transmits movement data to the inference engine and pages the patient when she needs to be reminded or alerted. The Care-Portal takes inputs from and provides decision support to the patient's caregivers. All three system components send data to the same inference engine and interfaces with the semantic knowledge base, but with different purpose.

Figure 36:
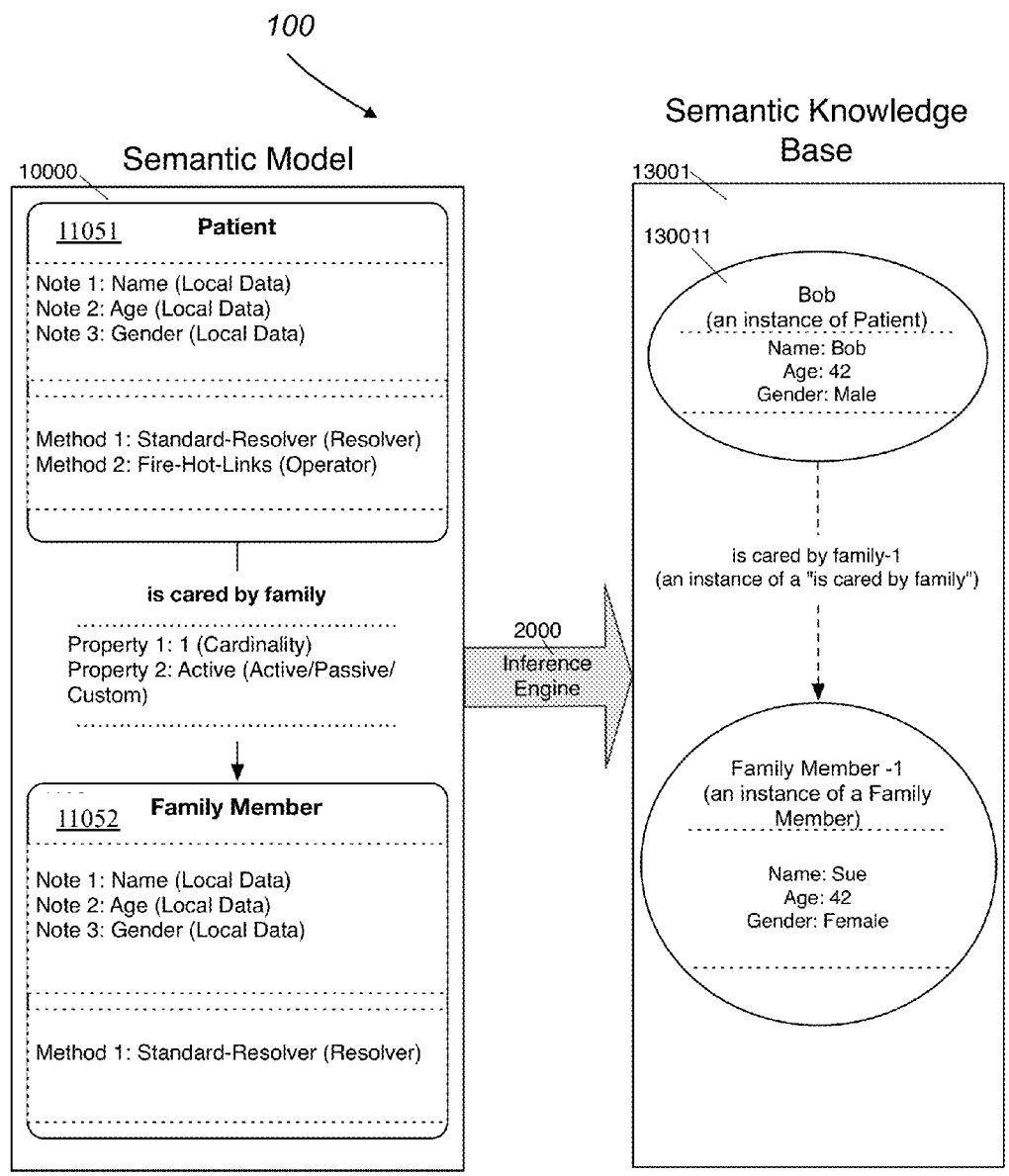
FIG. 36 illustrates an example of creating knowledge in a personal chronic illness management system.

In the PCIMS application, the semantic reasoning framework described in the present invention converts low level data, such as blood pressure measurement and medication adherence data to recommend follow-up actions to better manage chronic illnesses. FIG. 36 depicts that the PCIMS system has a semantic model which defines concepts related to chronic illness, the domain independent inference engine of the present invention, and a personal chronic illness management knowledge base that is created through the application of inference.

Figure 37:
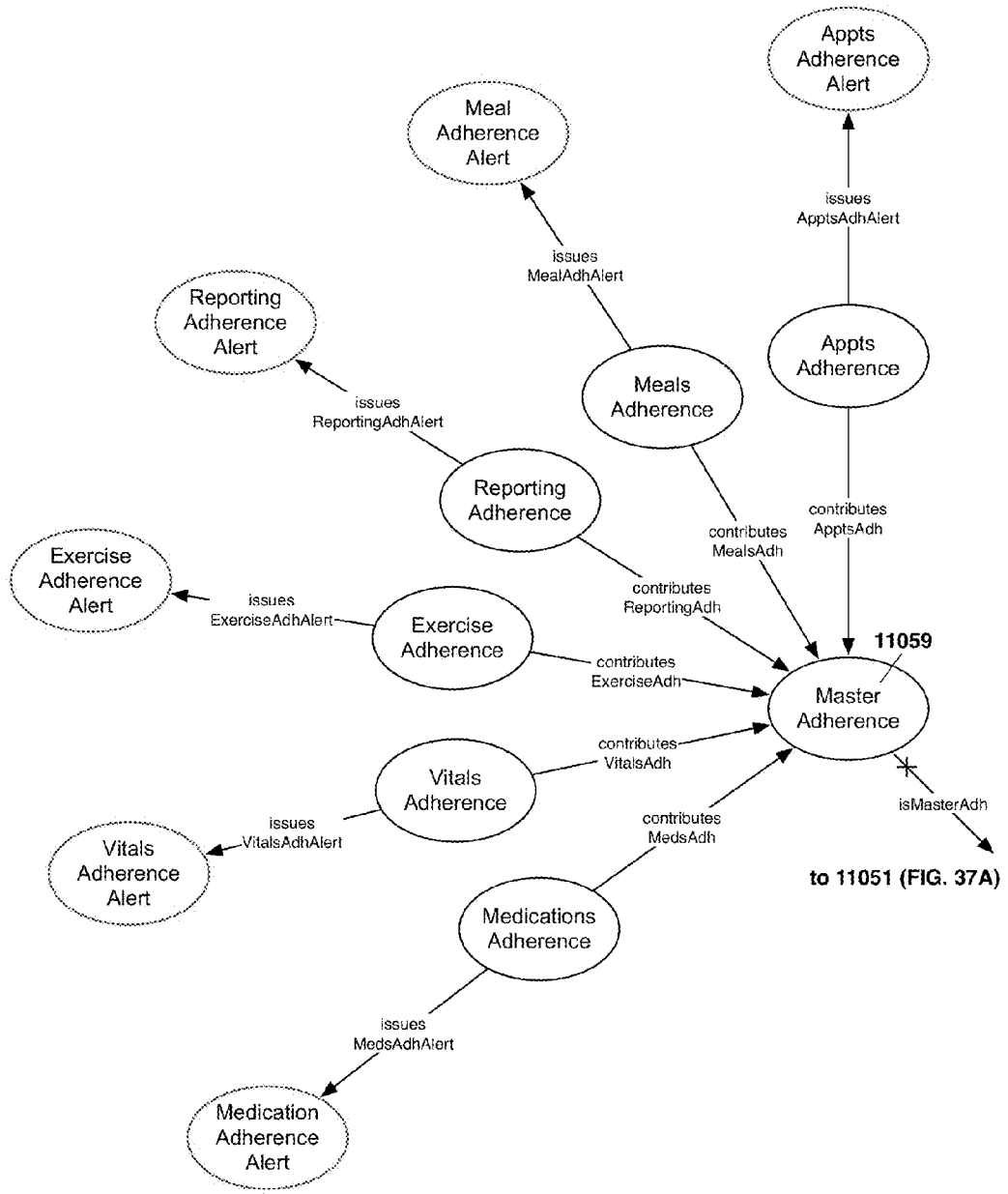
FIG. 37-FIG. 37C illustrate a semantic model for a personal chronic illness management system.
Figure 37A:
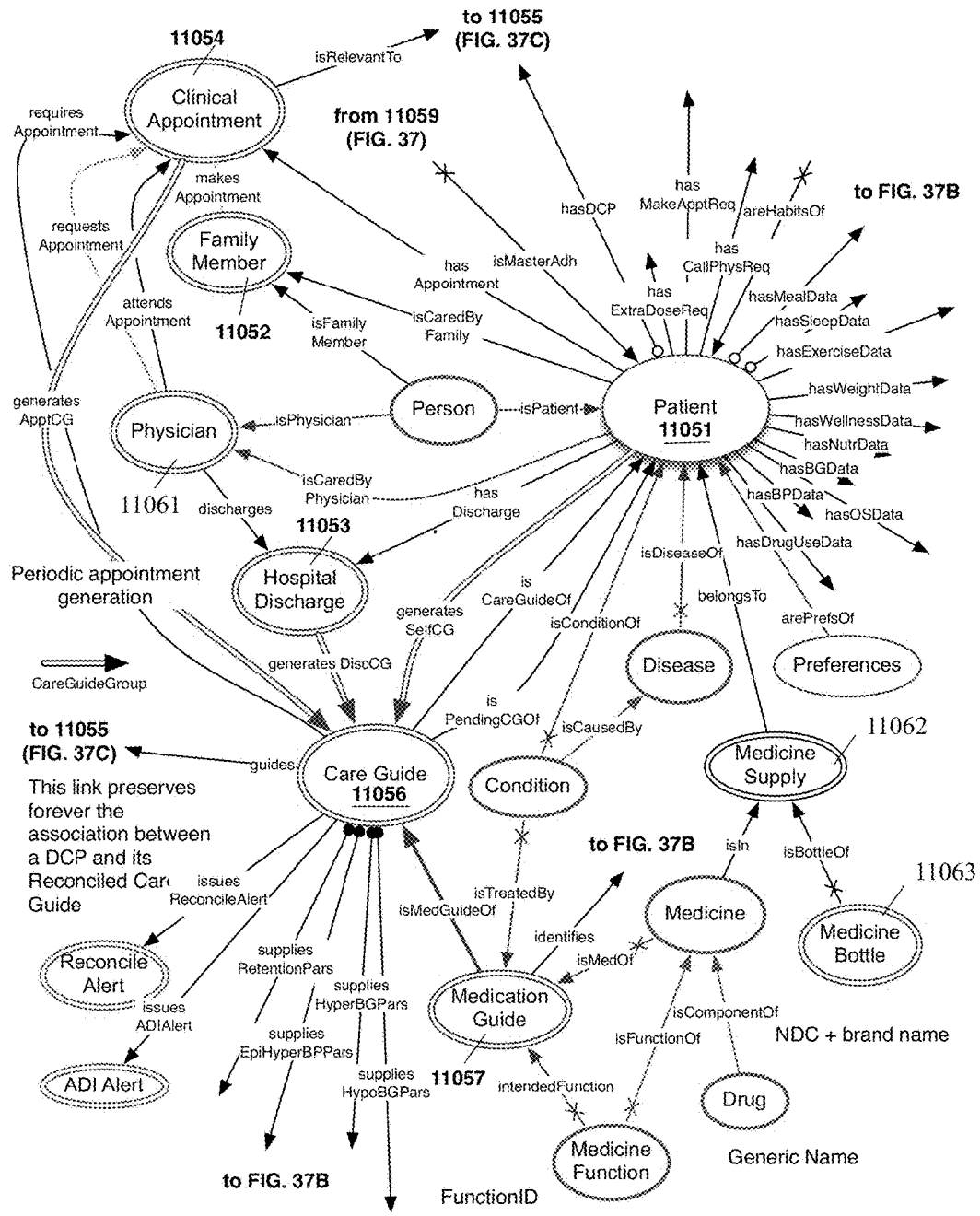
Figure 37B:
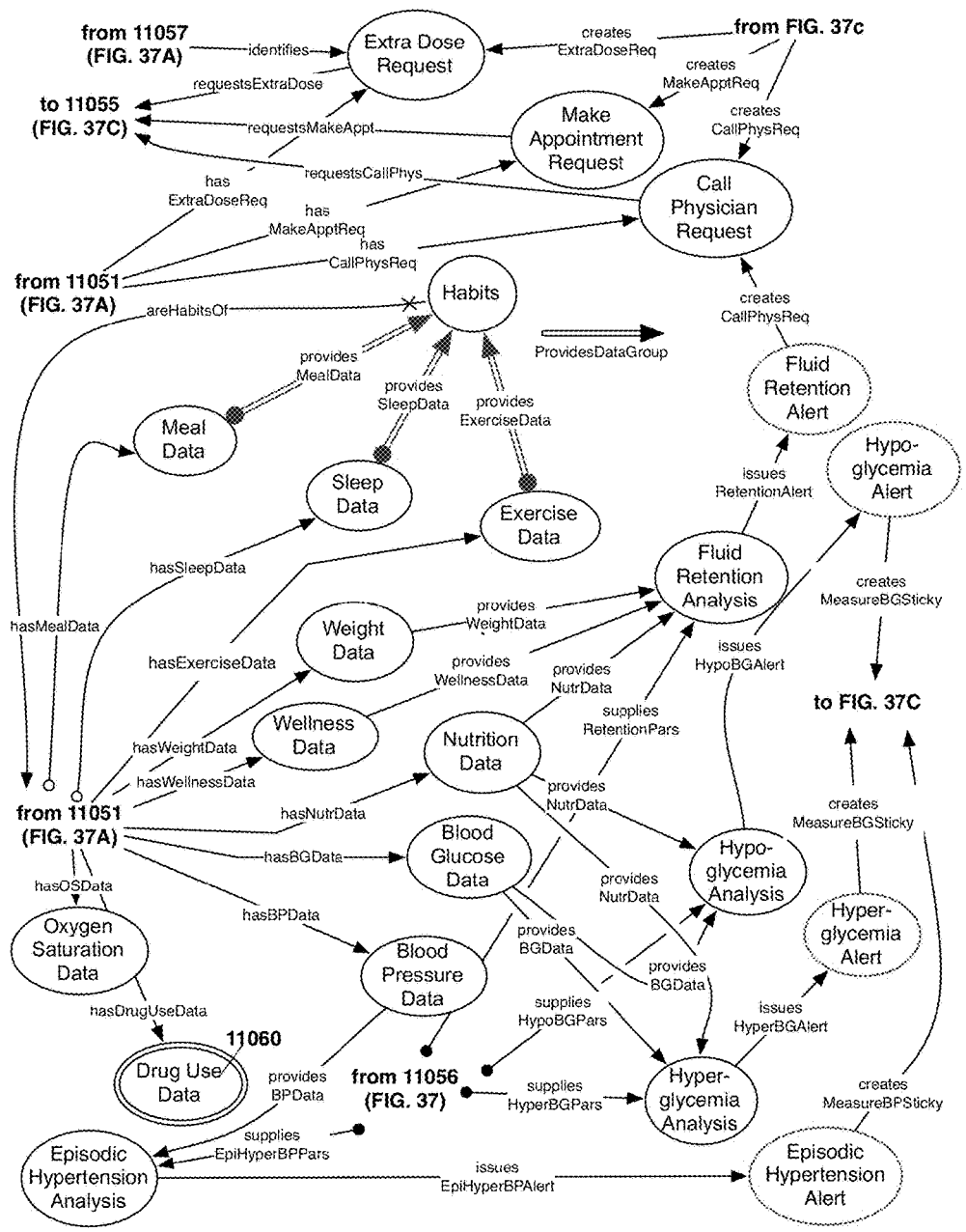
Figure 37C:
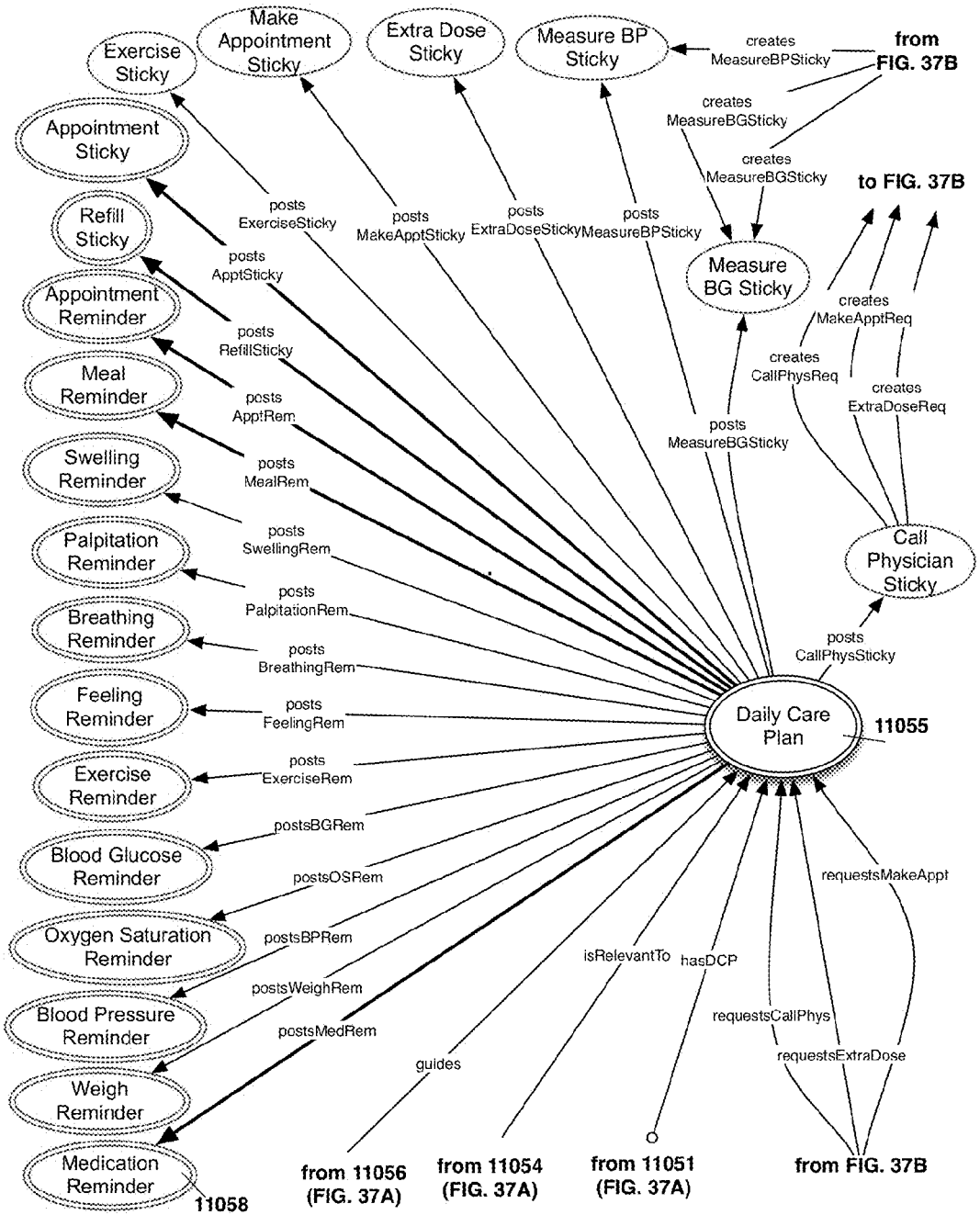

The PCIMS application employs cascading inferencing, where one inference leads to another until a resolution is reached or the process halts as it awaits additional data. As with all applications of the present teaching, the process of inference is described in the semantic model through the definition of insight concepts, relationships among concepts and associated operators. FIG. 37-FIG. 37C depict fragments of the PCIMS semantic model. Items including a clinical appointment 11054, family member 11052, patient 11051, physician 11061, hospital discharge 11053, care guide 11056, medication guide 11057, medicine supply 11062, medicine bottle 11063, drug use data 11060 depict fact concepts. Items including master adherence 11059 and its components, daily care plan 11055 and its components, depict different kinds of insights, representing knowledge about various patterns of patient behavior: medication adherence, meal taking, exercise, vitals signs and more. From the patterns, other insights are derived such as how regular is the patient with taking medication and finally recommendation on what to do when adherence and health are poor.

The PCIMS semantic model in FIG. 37-FIG. 37C include concepts such as "Patient" 11051 and "Family Member" 11052, connected by a relationship that describes which family member is a caregiver for the patient. Each concept is defined with notes such as name, age, and gender for "Patient" and "Family Member" concepts. Beyond the concepts for people involved in chronic care, the semantic model defines a range of concepts such as "Clinical Appointment" 11054 and "Hospital Discharge" 11055 which result in the specification of a "Care Guide" 11056 which, in turn, identifies the associated medications ("Medication Guide") 11057.

As the knowledge base gets seeded with knowledge about events such as clinical appointments and hospital discharges, the inference engine starts to implement the process of creating a "Daily Care Plan" 11055 which, in turn, prompts reminders for daily care tasks such as to take medications ("Medication Reminder"). When the care tasks are done, the patient reports the action through the Care-Station interface. Responses to reminders are tracked when the corresponding adherence nodes e.g. ("Medication Adherence" 11059) are periodically processed and adherence patterns are learned. Adherence alerts are issued if the operator function for the adherence node determines so.

Figure 38:
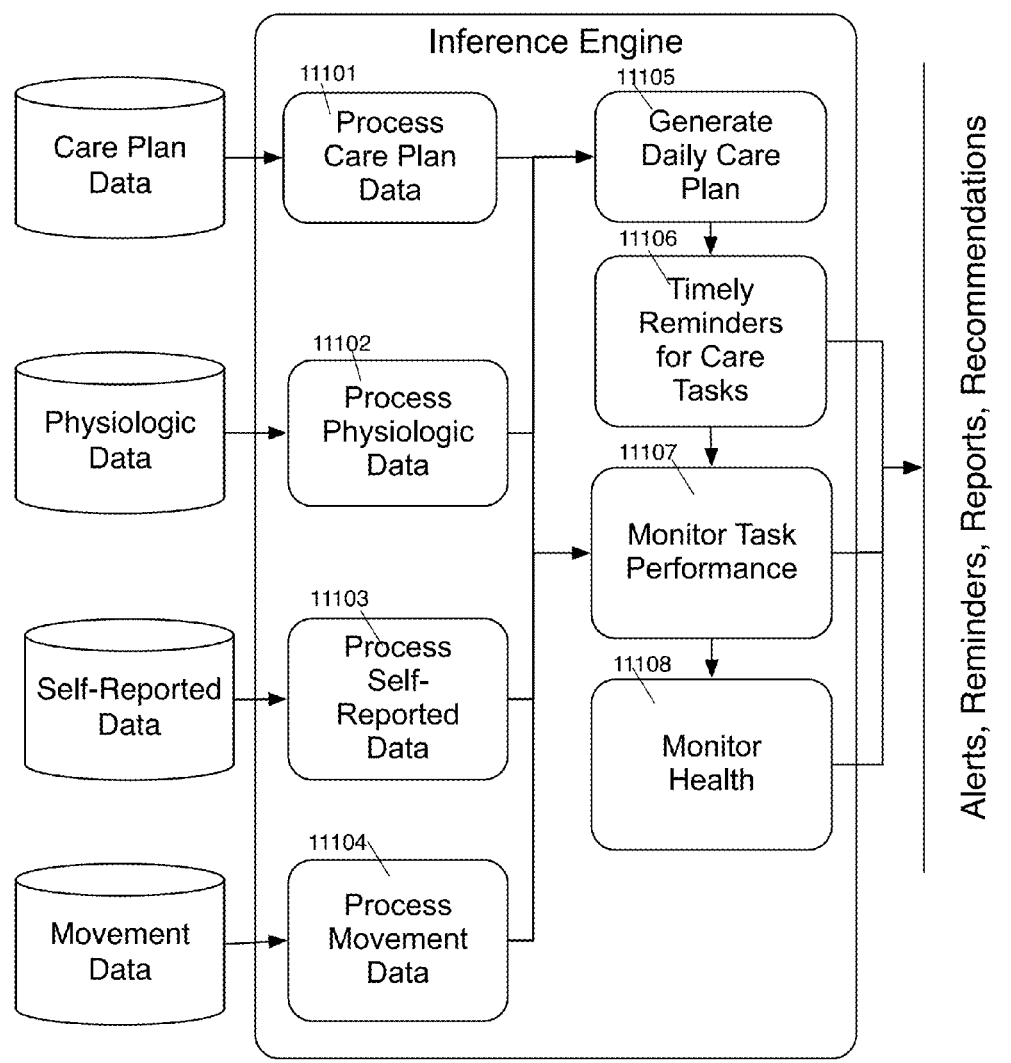
FIG. 38 illustrates examples of inferencing in a personal chronic illness management system.

Facts, such as a "Care Guide" 11056 created at a "Hospital Discharge" 11053, trigger downstream insight concepts, such as a "Daily Care Plan" 11055. Insight concepts identify functions that are used to process the notes within the fact nodes to generate insight nodes and its notes. For example, "Process Care Plan Data" 11101, shown in FIG. 38, depicts a specific function "Generate Daily care Plan" 11105 that is part of the "Daily Care Plan" concept 11055, shown in FIG. 37C. The trigger for the function represented by 11105 is a certain clock time, which is also specified in the semantic model as an argument to the function. The inference engine runs the trigger function at the specified clock time to create instances of 11055, which in turn triggers its downstream nodes. The same process applies to the functions 11102-11108, all of which are associated with insights concepts in the PCIMS semantic model in FIG. 37-FIG. 37C.

FIG. 38 depicts four types of data in PCIMS that are presented as facts to the inference engine. The four types of data are: data that describe the patient's care plan; physiologic data about the patient's vital signs; self-reported data capturing the patient's care plan adherence behaviors; and movement data captured by the wearable pager. These data result from the client acting on the reminders that are automatically generated. The data are processed by the inference engine to automatically create insights. Example of insights include generating a daily care plan for the patient, creating timely reminders for tasks that need to be done, such as taking medications and measuring vital signs, tracking performance of care tasks, and generating further reminders, alerts and recommendation when inferencing determines that there are issues with health or adherence. What needs to be inferred and the repertoire functions that are systematically invoked during the inference process are specified as insight concepts in the semantic model (shown in FIG. 37-FIG. 37C) and implemented by the inference engine of the present invention.

The four types of data in PCIMS that are presented as facts to the inference engine come from two types of sources: sensors and user inputs. FIG. 39-42 describe the inference flow for processing the fours types of data in PCIMS.

Figure 39:
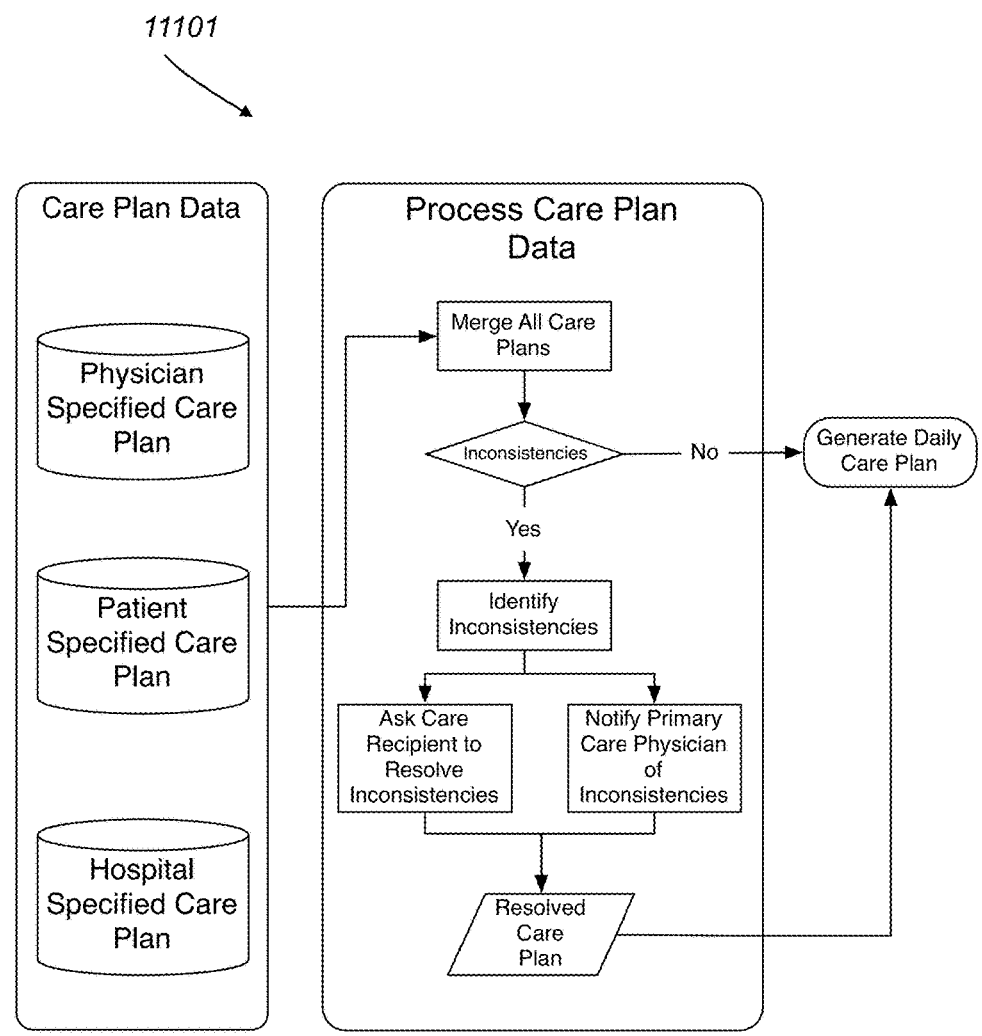
FIG. 39 illustrates care plan processing in a personal chronic illness management system.

FIG. 39 describes the logic for function 11101 in FIG. 38. The logic is embodied in one or more repertoire functions that process multiple inputs to a patient's care plan into a single daily care plan. The single daily plan includes a schedule of all the tasks that the patient needs to do on any given day. Multiple, intermediate semantic concepts may be instanced during the process of creating the daily care plan. The intermediate concepts may represent intermediate knowledge such about inconsistencies in the care plans, and requests to patients, caregivers and physicians to resolve inconsistencies. Whether intermediate concepts are defined in the semantic model or not depends on what knowledge needs to be tracked, in order to provide the desired decision support to the application's users.

Figure 40:
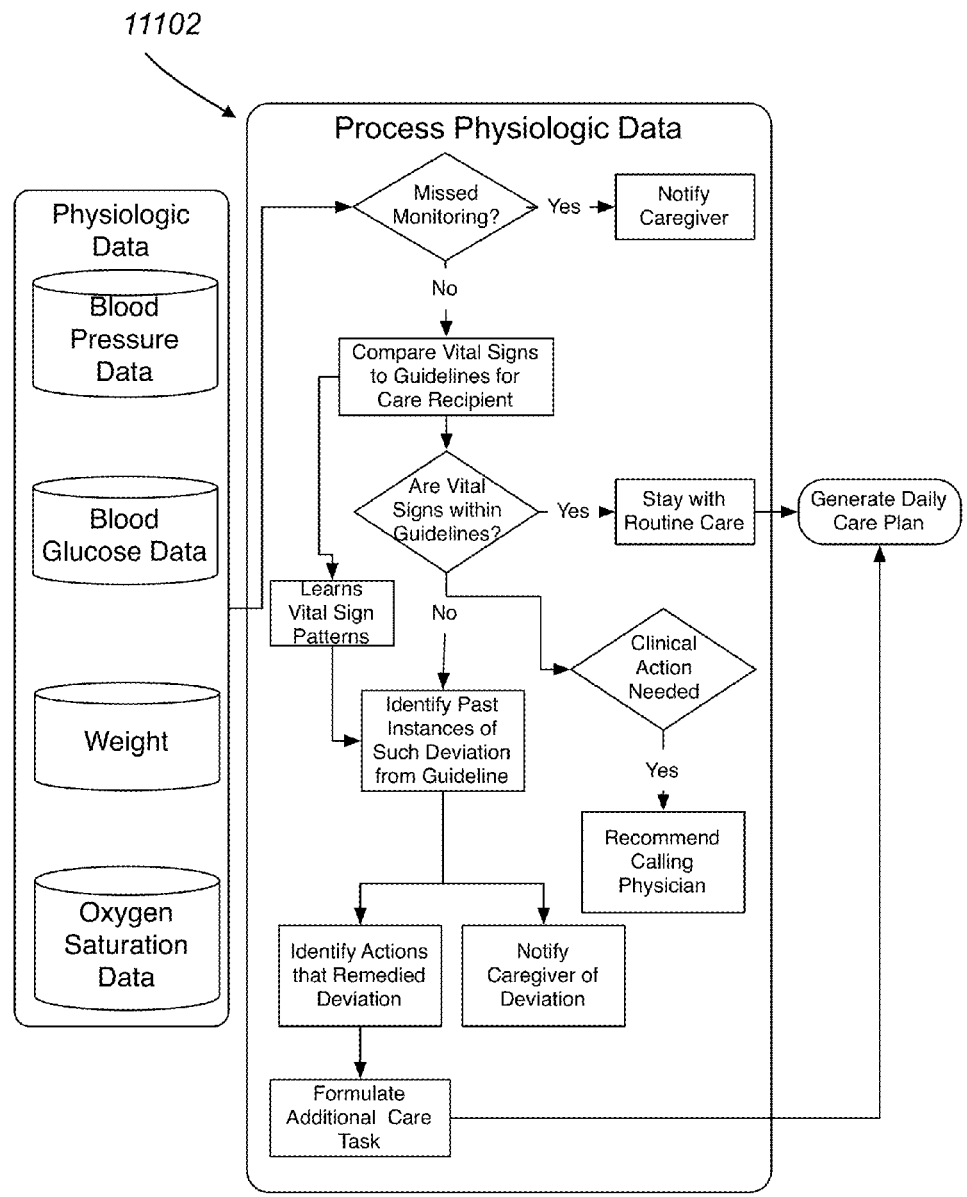
FIG. 40 illustrates the processing of physiologic data in a personal chronic illness management system.

FIG. 40 describes the logic for function 11102 in FIG. 38. The logic may be embodied in one or more repertoire functions, associated with one or more concepts, and are dynamically invoked by the inference engine in the course of creating new insight nodes and links as they are triggered by the creation and updates of fact nodes. Typically, each data type in FIG. 40 is represented as a unique concept, with its own notes and repertoire functions customized to process the notes in the concept. Notifications to caregivers and recommendations, such as to call physicians, are also distinct decision support concepts in the semantic model. Instances of the decision support concepts are created in the semantic knowledge base when the logic depicted in FIG. 40 is satisfied.

Figure 41:
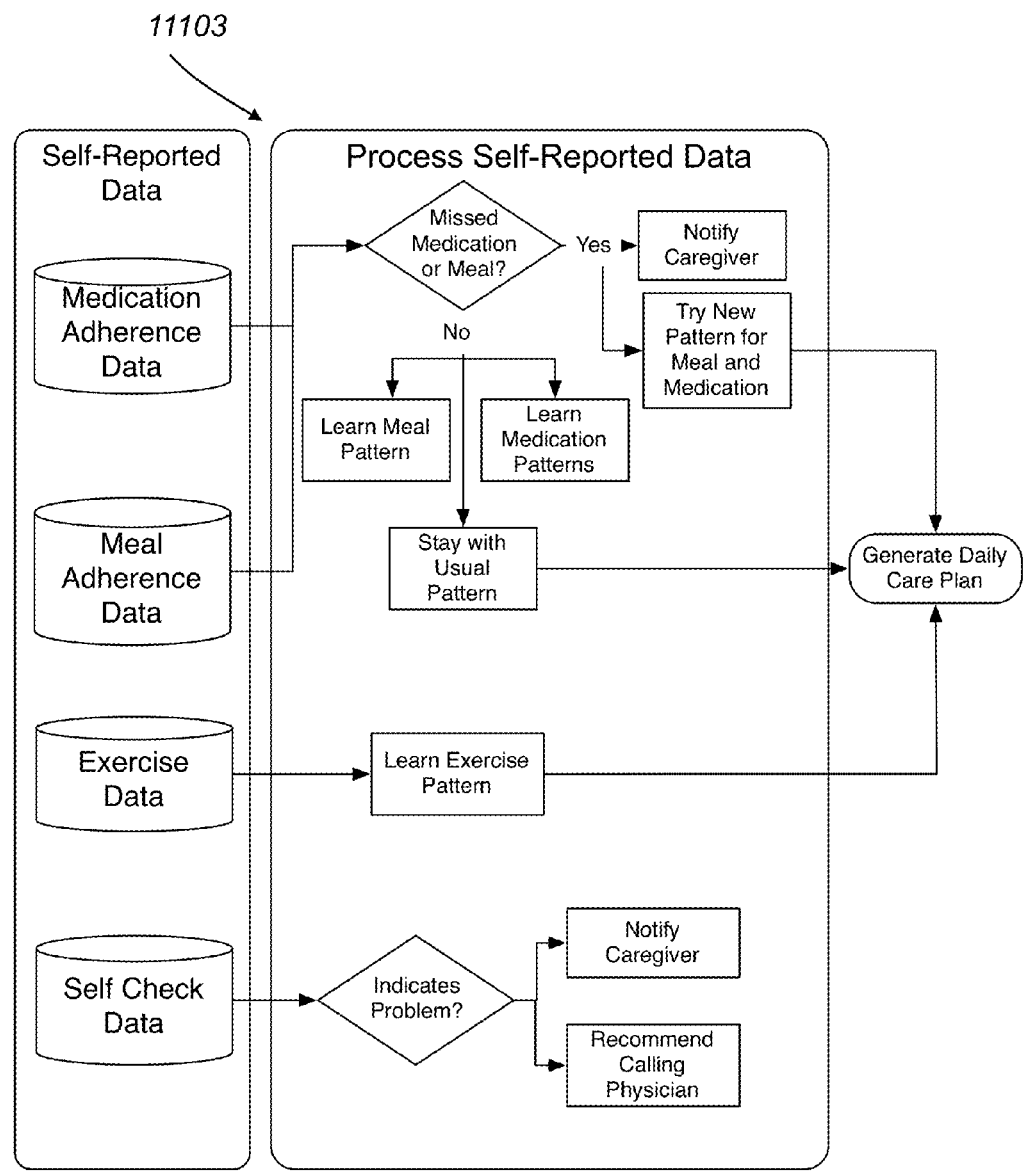
FIG. 41 illustrates the processing of self reported data in a personal chronic illness management system.

FIG. 41 describes the logic for function 11103 in FIG. 38. The logic may be embodied in one or more repertoire functions, associated with one or more concepts, and are dynamically invoked by the inference engine in the course of creating new insight nodes and links as they are triggered by the creation and updates of fact nodes.

Figure 42:
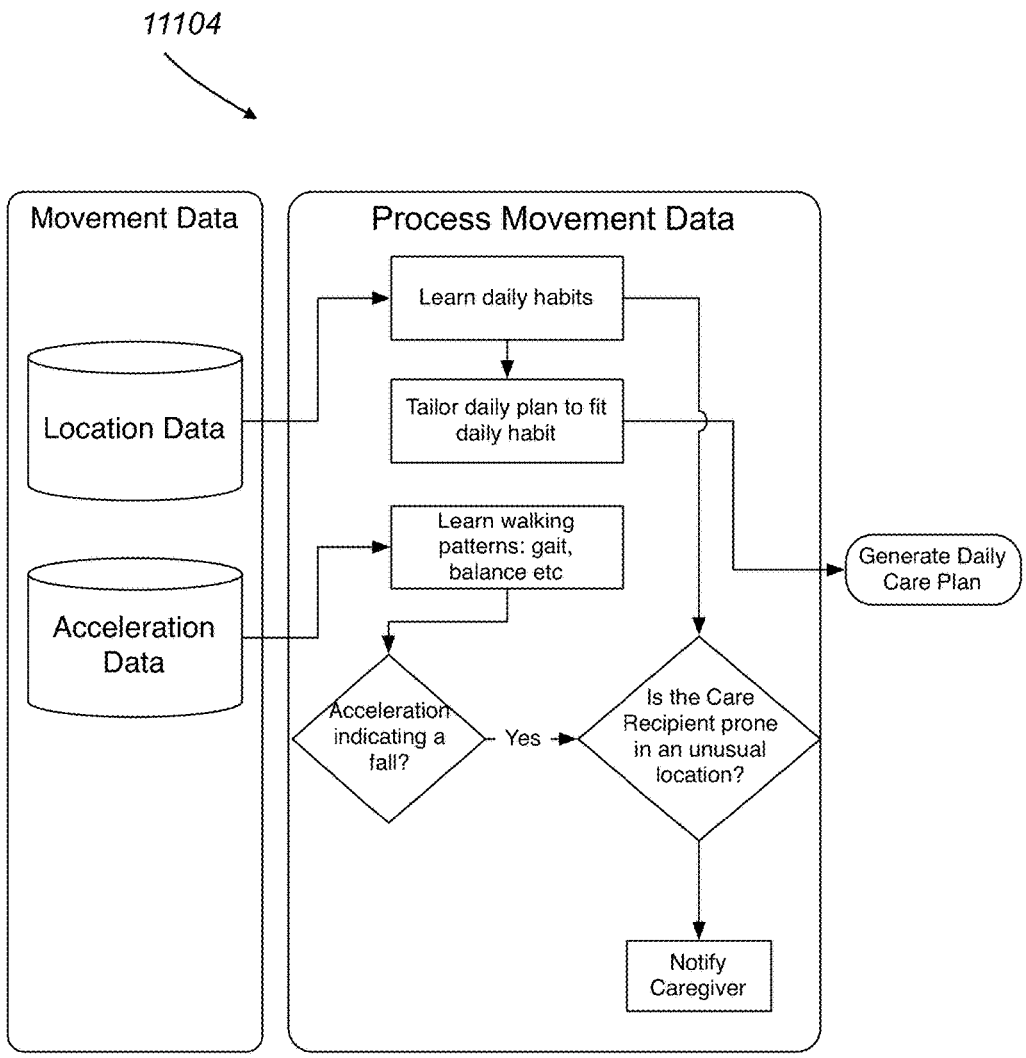
FIG. 42 illustrates reasoning based on location of a care recipient within a home.

FIG. 42 describes the logic for functions 11104, shown in FIG. 38. The logic describes the processing of the movement data to infer activities of daily living and learn daily habits. The logic may further process the movement data to learn patterns of walking from which the inferences about falls can be made. The logic for movement analysis may be embodied in one or more repertoire functions, associated with one or more concepts, and are dynamically invoked by the inference engine in the course of creating new insight nodes and links as they are triggered by the creation and updates of fact nodes.

The logic described in FIG. 39-FIG. 42 is implemented by functions associated with multiple concepts in the semantic model. For example, the logic "Clinical Action Needed" is implemented by multiple concepts in the PCIMS semantic model: Fluid Retention Analysis, Hypoglycemia Analysis, Hyperglycemia Analysis, and Episodic Hypertension Analysis. A single instance for these concepts is created by the inference engine when a patient is diagnosed with a corresponding disease. Each of these nodes is triggered when its input link, connecting it to its corresponding data, is fired upon the arrival of new data. Specific repertoire functions carry on the analysis of the situation represented by the concept: fluid retention, hypoglycemia, hyperglycemia and hypertension. The result of the analysis can be alerts about needing clinical action.

Figure 43:
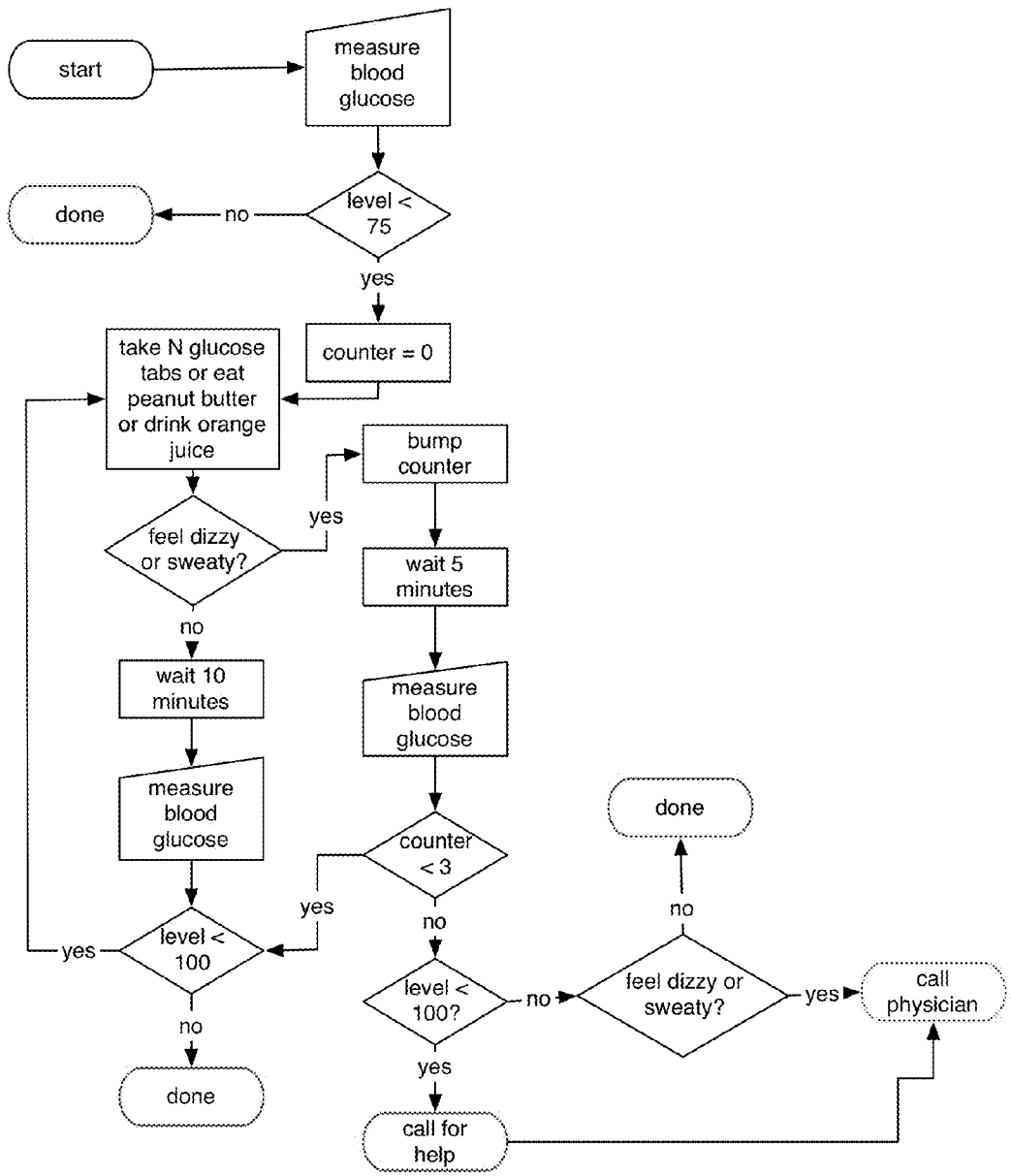
FIG. 43 illustrates an alert protocol used within a personal chronic illness management system.
Figure 44:
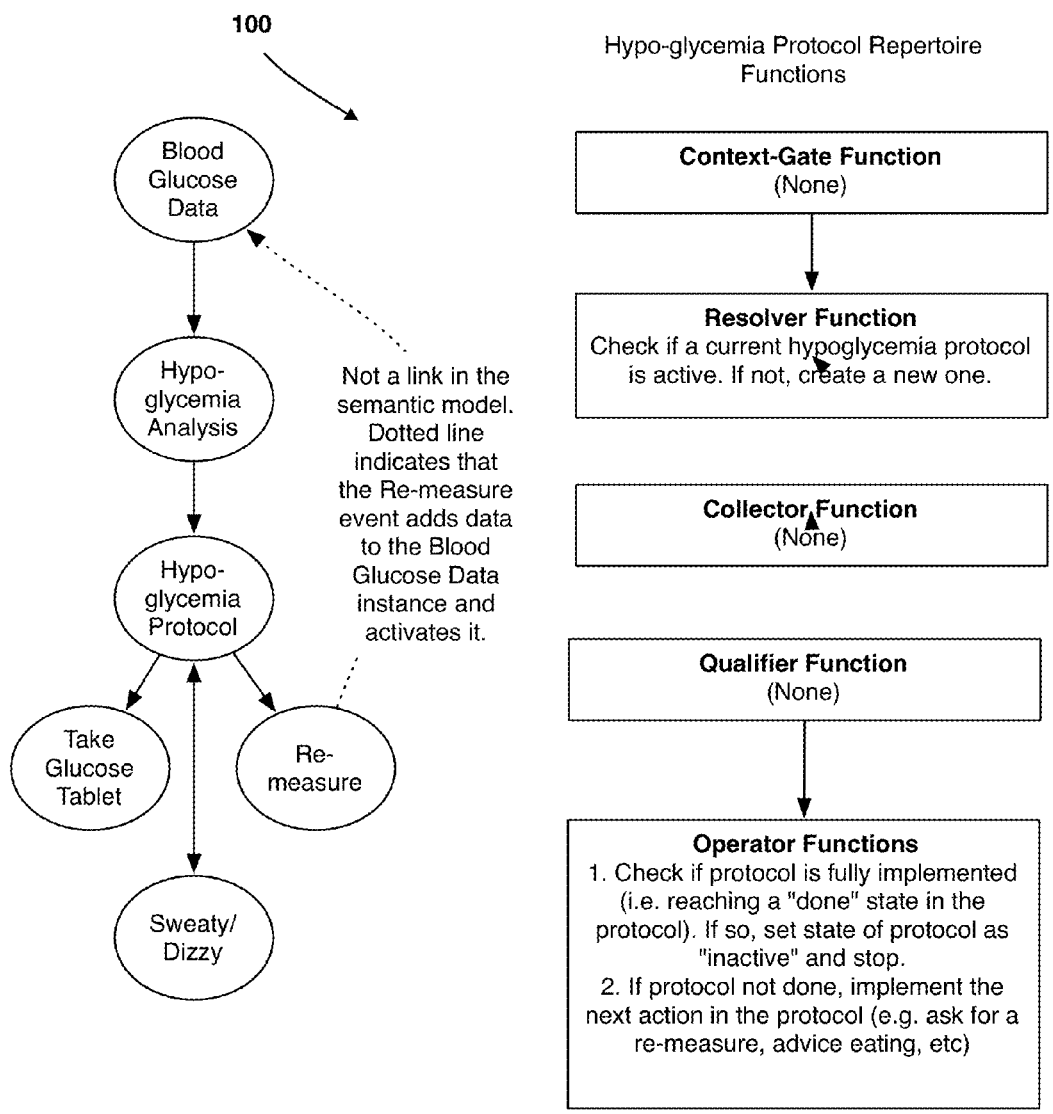
FIG. 44 illustrates one implementation of operators for the hyperglycemia alert concept in a personal chronic illness management system.

FIG. 43 depicts the logic of the analysis that is associated with Hypoglycemia Analysis. FIG. 44 depicts its implementation through the inference mechanism of the present teachings. New Blood Glucose Data activates the Hypoglycemia Analysis node. An operator function associated with the node tests whether glucose level is below 75. If so, a Hypoglycemia Protocol node is instanced. This node implements the clinical protocol in FIG. 43 involving multiple, sequenced measurements of glucose level, recommendation to take glucose tablet, and checking whether the patient feels sweaty or dizzy. Each of these actions is represented by its own concept in the semantic model. An operator within the protocol node keeps track of how much of the protocol has been followed. If a "Call Physician" or "Call for Help" state is reached, a Hypoglycemia Alert node is created to indicate whether a physician or a friend should be called for help.

The nodes and links created by the inference engine are stored in the semantic knowledge base and are available for query by the three interfaces for the PCIMS: the Care-Station, the Pager and the Care-Portal, shown in FIG. 35. Each of the three interfaces queries the PCIMS semantic knowledge base using the query meta-language illustrated in FIG. 19. The replies to the queries are displayed to the user using various forms of user interface objects, illustrated in FIG. 45-FIG. 63.

Figure 45:
FIG. 45 illustrates a touch screen interface for a client whose behavior is activated by a personal chronic illness management system.

FIG. 45 depicts the main interface for the Care-Station. The entire interface is controlled by touch. At the center is a window that displays photos selected by the user. The left panel provides a clock and the current date. The rest of the interface includes buttons that activate the user to take specific actions. The left panel provides a button to access various options for communicating with family and caregivers. It also provides a button that communicates rewards earned by the user for successfully completing tasks.

The bottom panel in FIG. 45 sequentially displays a series of buttons corresponding to the tasks for the day. Icons are used to represent the tasks: medicine bottle for taking medications, plates of food for taking meals, and devices for monitoring vital signs. The time to do the task is indicated below the task icon in an oval whose colors can be green for done, red when overdue and black when upcoming. The daily tasks are dynamically computed by the inference engine and stored in the semantic knowledge base as reminder concepts. The care-station interface periodically queries the semantic knowledge base for the status of upcoming tasks and updates the care-station interface accordingly. Tasks that are completed are indicated as "Done". The right panel illustrates unscheduled tasks that need attention. Each scheduled or unscheduled task depicted in the interface is an instance of a reminder in the PCIMS semantic model shown in FIG. 37-FIG. 37C.

Figure 46:
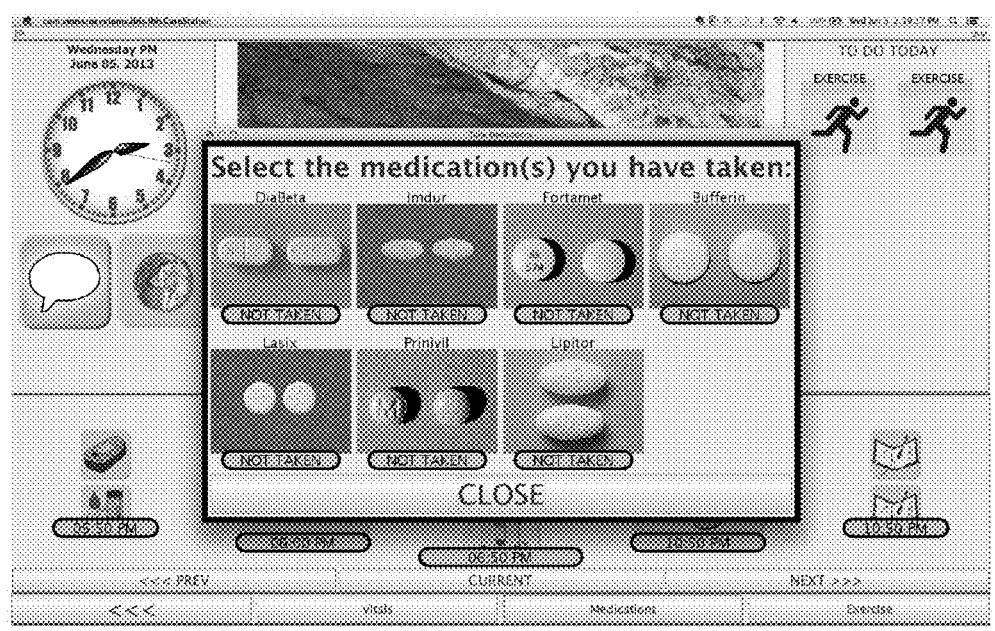
FIG. 46 illustrates an additional layer of interactions with a user that is docked to the application dashboard.

FIG. 46 illustrates what happens when a medication icon is touched: a panel depicting all the medications to be taken as part of that task is shown. Touching the image of a medication brings up a panel that informs the user of the quantity of medication to be taken and allows the user to specify whether the medication was taken or skipped. Every user input is sent to the inference engine and processed by the inference engine following the logic specified in the semantic model.

Figure 47:
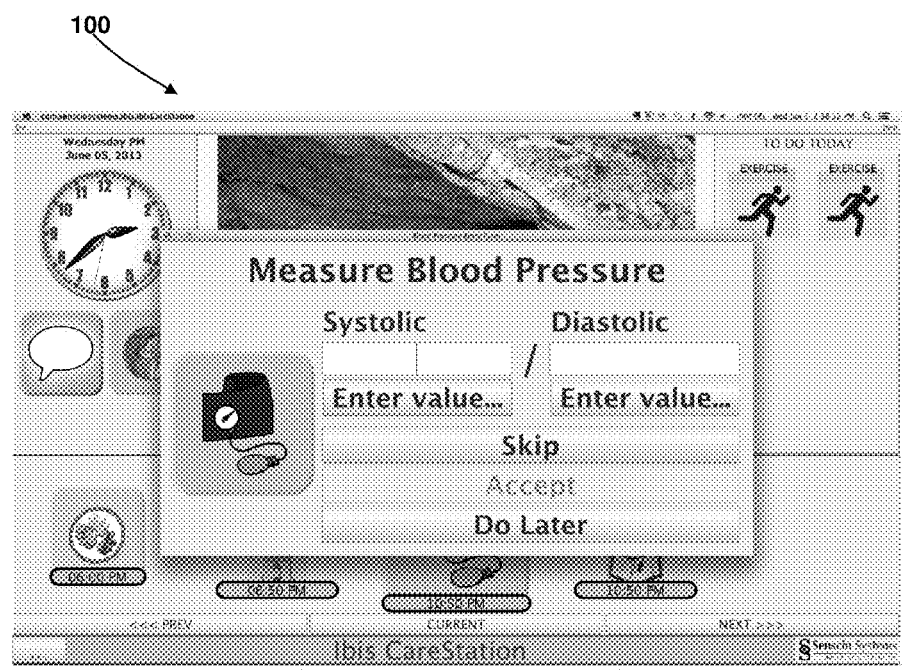
FIG. 47 illustrates interaction with the user, docked to the application dashboard, reminding the user to take their vitals before going to bed.

FIG. 47 illustrates the panel that appears when the user touches a blood pressure device icon. The panel allows the user to enter blood pressure readings. If a device is directly connected to the PCIMS application, the blood pressure reading may be automatically captured. Blood pressure readings are sent to the inference engine where they are analyzed. If further actions are needed, the actions appear as new tasks on the right panel of the main interface, shown in FIG. 45.

Figure 48:
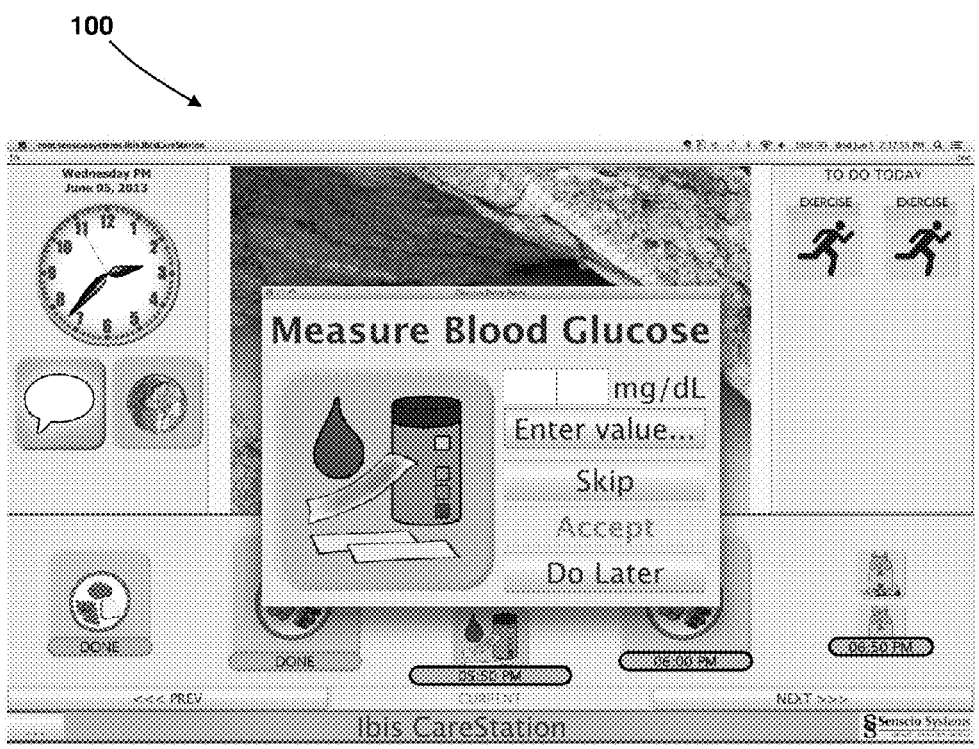
FIG. 48 illustrates multiple layers of interactions, each building upon the other, docked to the application dashboard.

FIG. 48 shows the panel that appears when a blood glucose device icon is touched. The manually or automatically entered data are sent to the inference engine, where they trigger a hypoglycemia and hyperglycemia analysis and ensuing protocol as described in FIG. 43 and FIG. 44.

Figure 49:
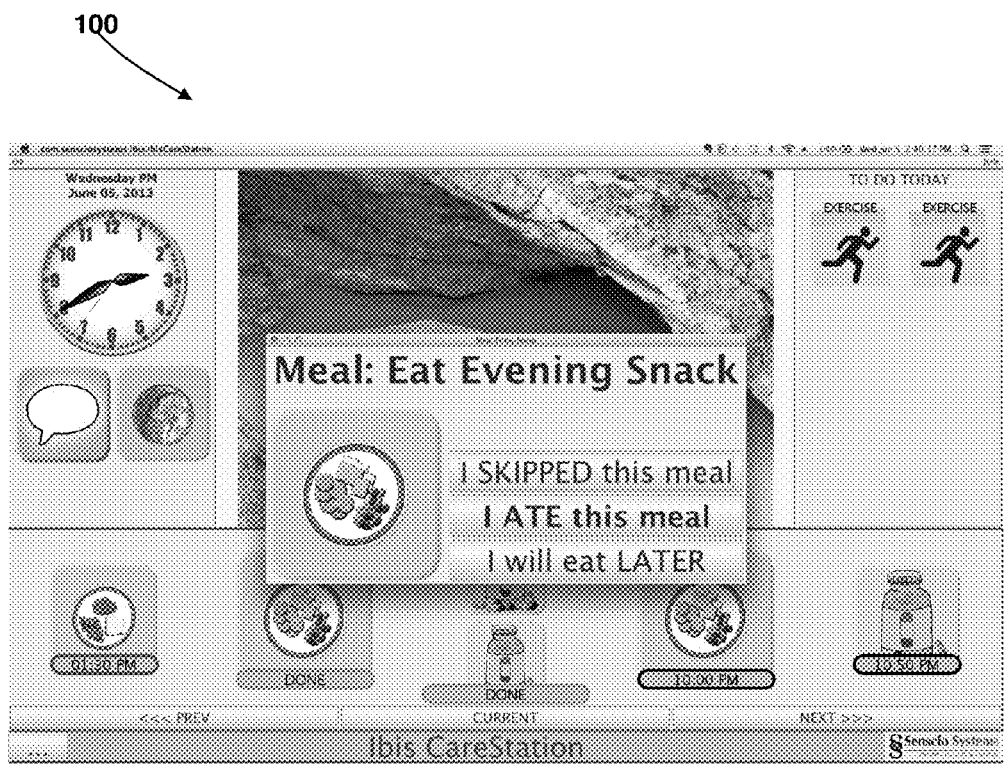
FIG. 49 illustrates another type of interaction with a user, docked to the application dashboard, reminding the user to pay attention to their appropriate eating schedule.

FIG. 49 shows the panel that appears when a meal icon is touched. The panel allows the user to indicate whether the meal was taken skipped or yet to be done. The user input becomes a fact that the inference engine processes to learn eating habits. Extensions to the semantic model track what was eaten and correlate food intake with drug metabolism, weight gain, or sleep patterns. As the semantic model is extended, the panel shown in FIG. 40 is extended to accept user input of the contents of the meal.

Figure 50:
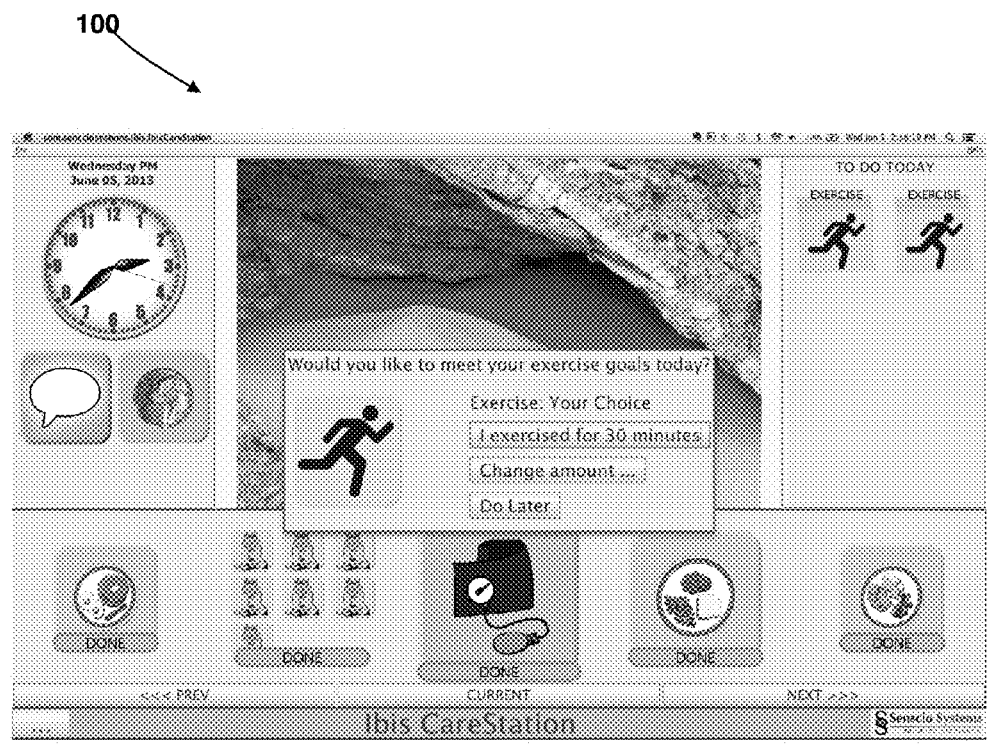
FIG. 50 illustrates multiple types of interactions with a user, docked to the application dashboard.

FIG. 50 depicts the panel that appears when an exercise icon is touched. It captures user input on the nature and extent of the exercise. The input is sent to the inference engine in real time where it triggers the learning of exercise habits and its immediate and longitudinal effect on vital signs such as pulse, blood pressure, and weight, among others. The instantaneous and asynchronous analysis of the many dimensions of a user's input is one of the many benefits of the semantic reasoning approach of the present invention.

Figure 51:
FIG. 51 illustrates another type of interaction with a user, docked to the application dashboard, asking the user to check for swelling in their legs.

FIG. 51 accepts user input on self-checks that the user is tasked to do. The self-check inputs are instantaneously correlated with vital signs to detect the onset of health issues such as fluid retention.

Figure 52:
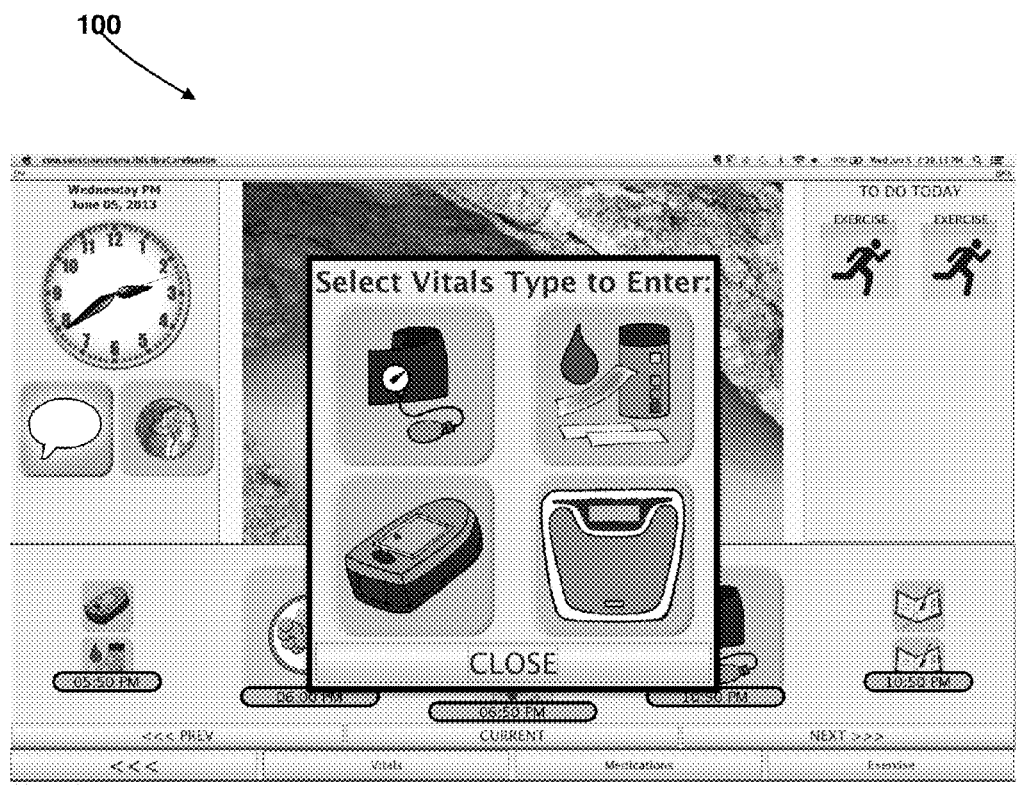
FIG. 52 illustrates the application dashboard for a personal chronic illness management system with the ability to hide or reveal additional options for interactions.

FIG. 52 depicts the prompt to the user when multiple, related tasks are to be done at the same time. Until each task is complete, the main task icon will continue to indicate that the task needs to be done. When all tasks in a group are done, the task icon in the main task panel at the bottom of FIG. 45 will indicate that the task is done.

Figure 53:
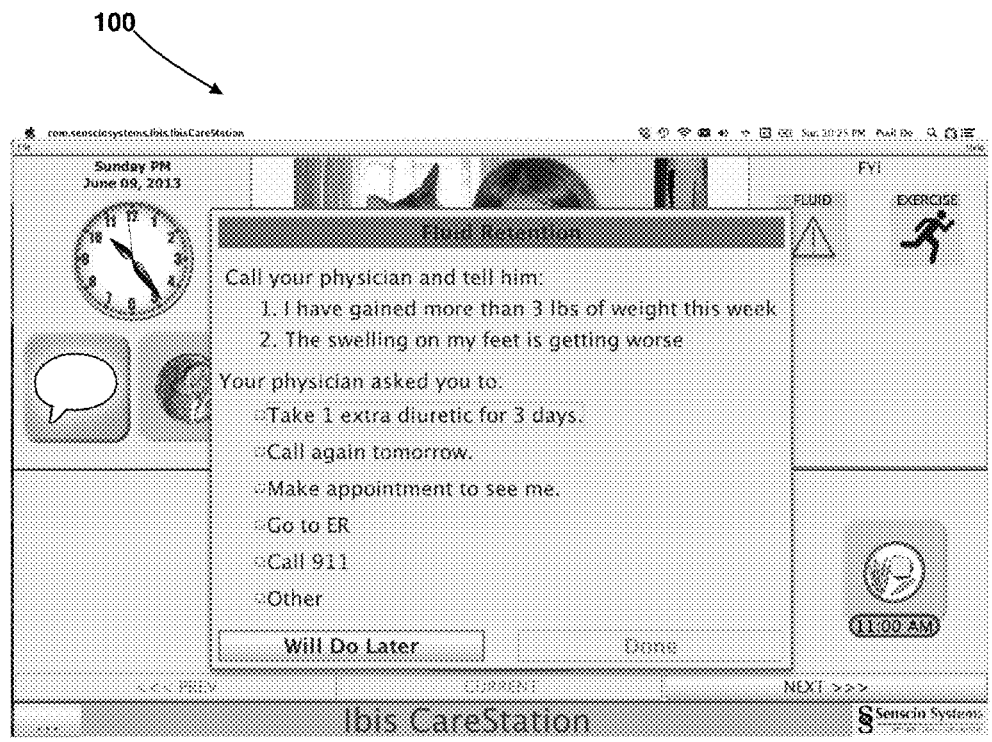
FIG. 53 illustrates an application of a clinical protocol to respond to fluid buildup as inferred by the personal chronic illness management system.
Figure 54:
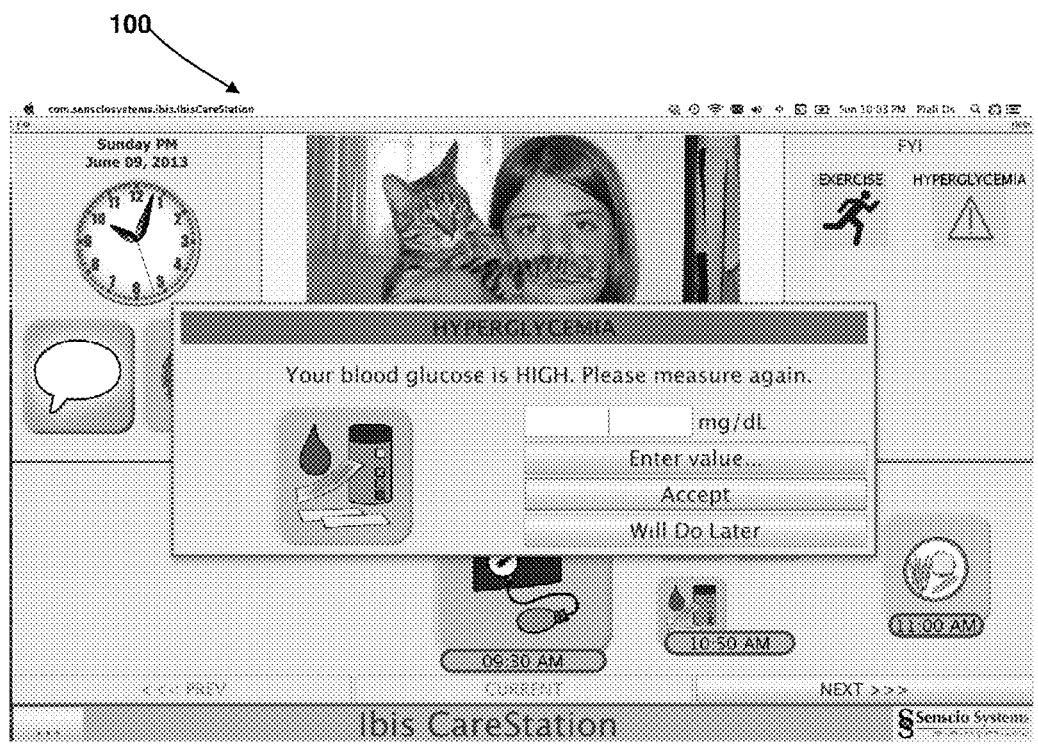
FIG. 54 illustrates an application of a clinical protocol to respond to hyperglycemia as inferred by the personal chronic illness management system.

FIG. 53 is an example of behavioral activation due to conclusions drawn by the inference engine in real time from processing various user inputs. In this example, the inference engine concludes that there is a likely situation of fluid retention. This conclusion is drawn from patterns of weight gain, swelling of the feet and breathing difficulties. Once the conclusion is drawn, an icon on the right panel on the main interface indicated a fluid retention alert. The panel in FIG. 53 is shown when the alert icon is touched. The panel in FIG. 53 explicitly instructs what the user should do; call physician in this instance. The panel also accepts user's input from the activity; in this example it accepts input on the physician's instructions. The inference engine processes the user input and continues to activate the user for the next necessary action. For example, if the instruction was to take extra diuretics, the right hand panel will post a new icon indicating that medication needs to be taken. The activation will continue until the protocol is complete. As explained in FIG. 44, a semantic concept for implementing fluid retention protocol continuously draws the inferences necessary to fully implement the protocol until a done state is reached.

The inference engine operates asynchronously and is able to conduct multiple threads of reasoning in parallel. Multiple alert protocols can be implemented at the same time. FIG. 53 shows one step in implementing a hypoglycemia protocol (shown in FIG. 43) requiring additional, periodic measurements of blood glucose. The data for the glucose level, when entered manually or automatically, are instantaneously processed by the inference to arrive at the next action in the hypoglycemia protocol.

Figure 55:
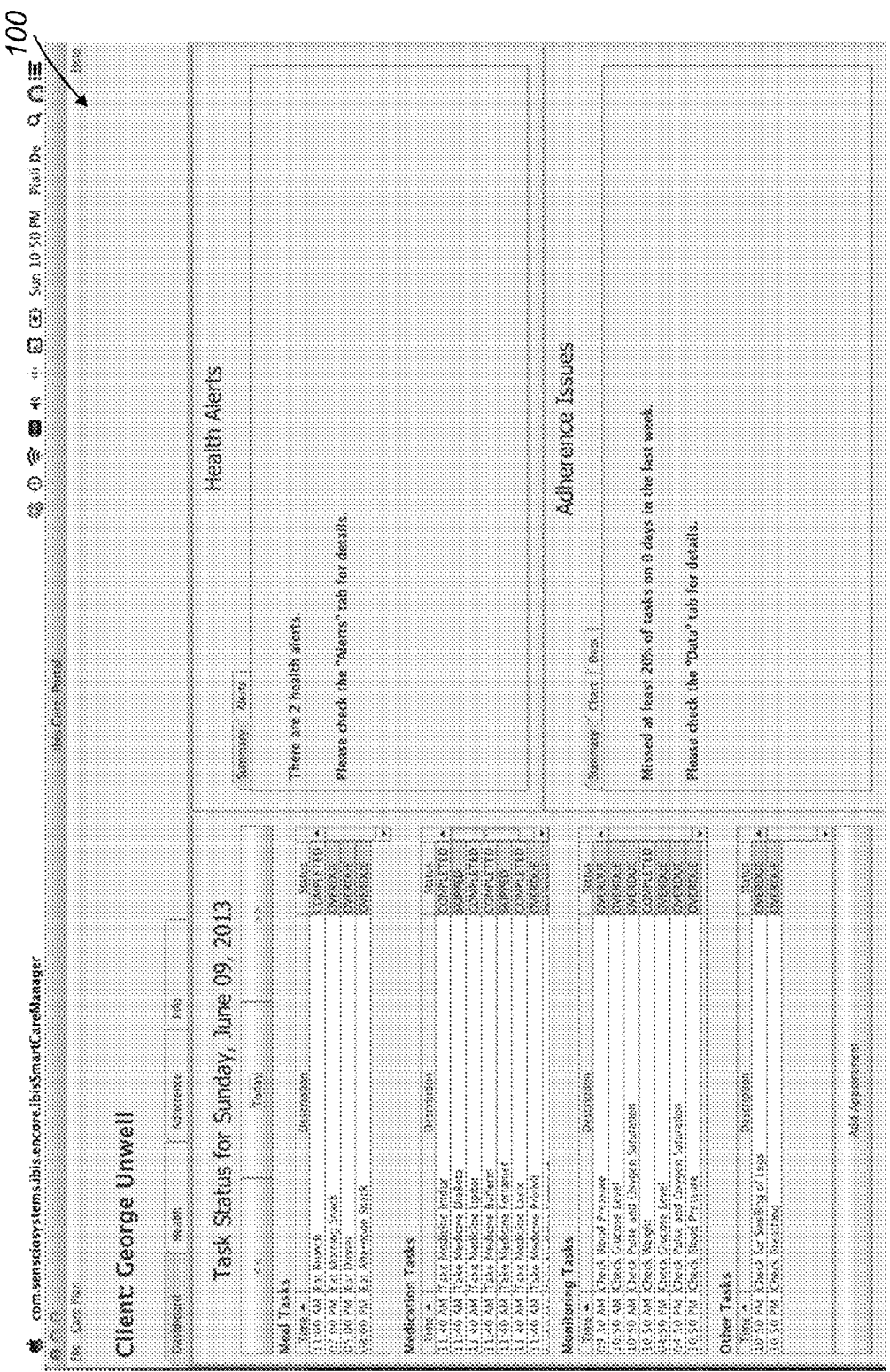
FIG. 55 illustrates the primary interface care-portal used by the caregiver users of the personal chronic illness management system.
Figure 56:
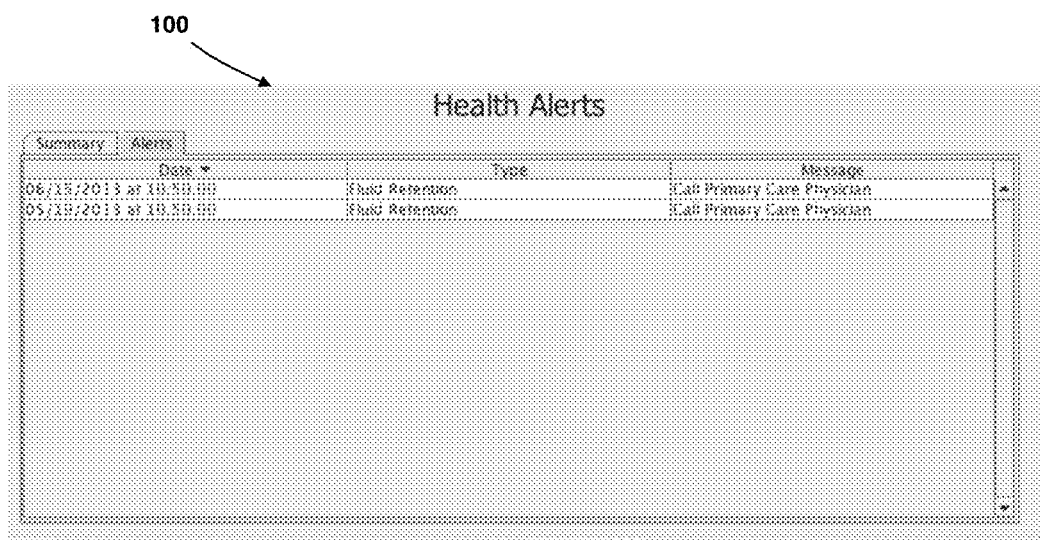
FIG. 56 illustrates that the care-portal summarizes health and care-plan adherence alerts.
Figure 60:
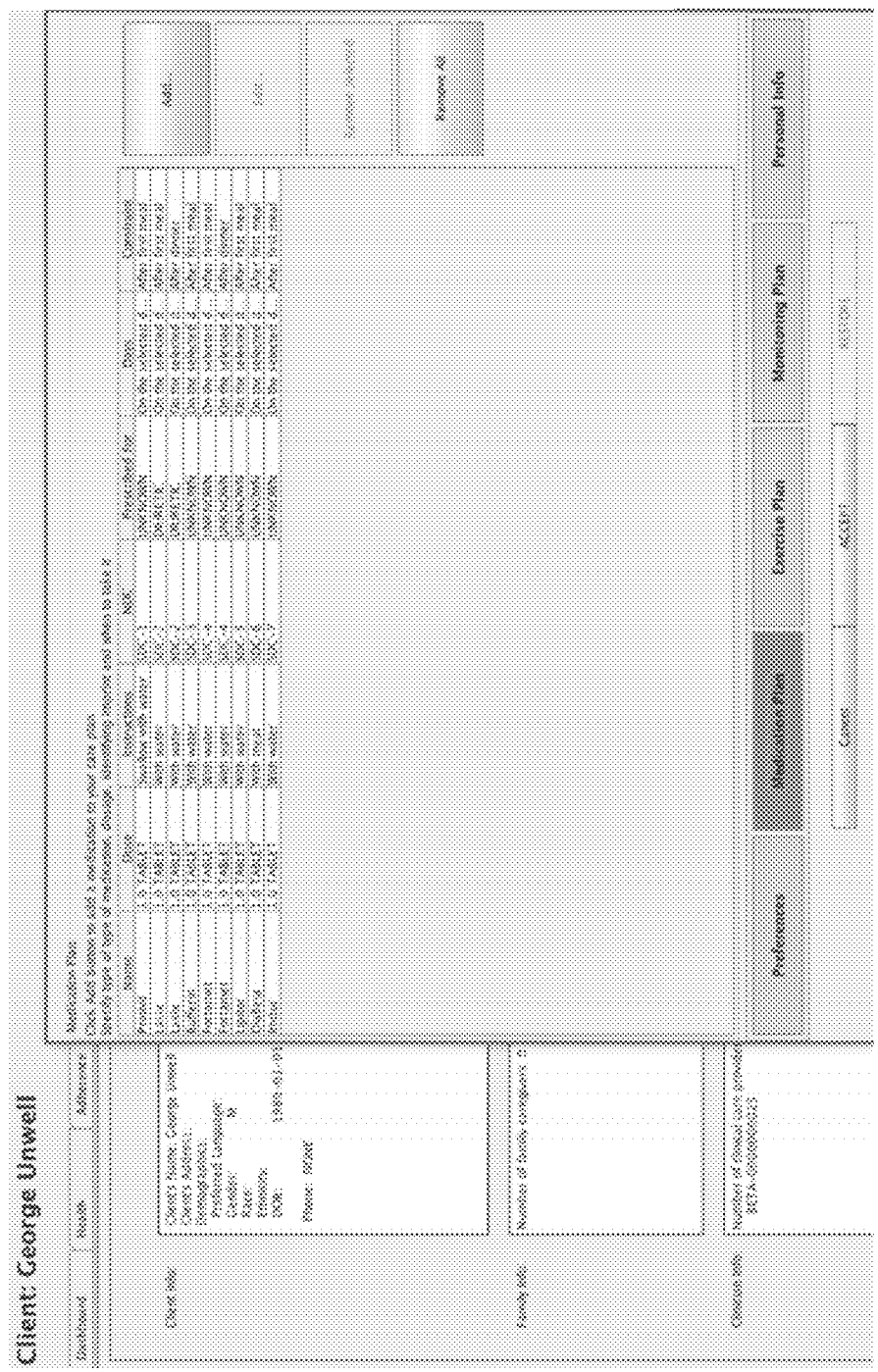
FIG. 60 illustrates the care-portal's provision to add, edit, and remove medications to be taken by the user on a scheduled basis.
Figure 61:
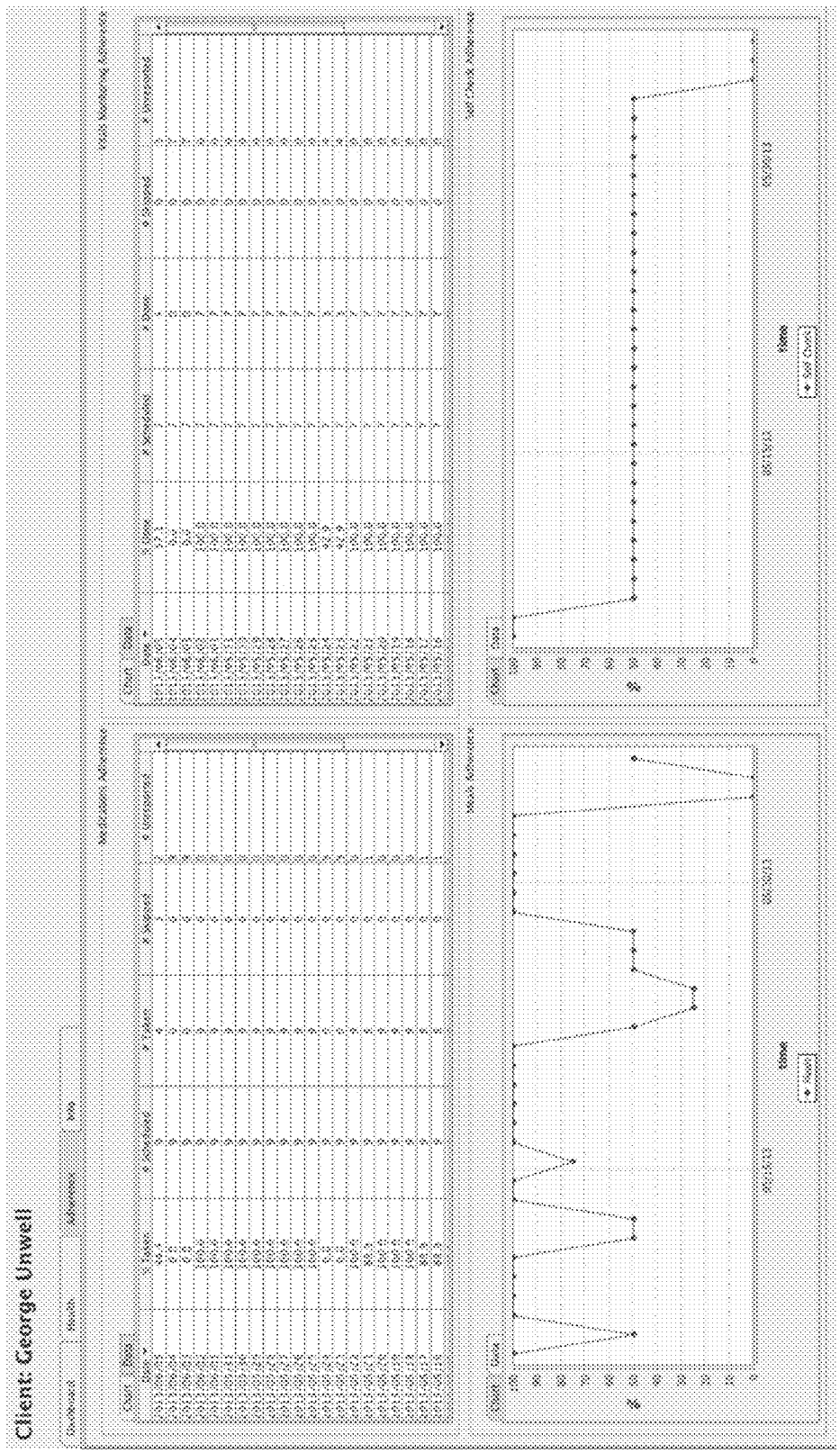
FIG. 61 illustrates the different viewing options, both graphic and statistic, of the user's adherence to their care plan.
Figure 62:
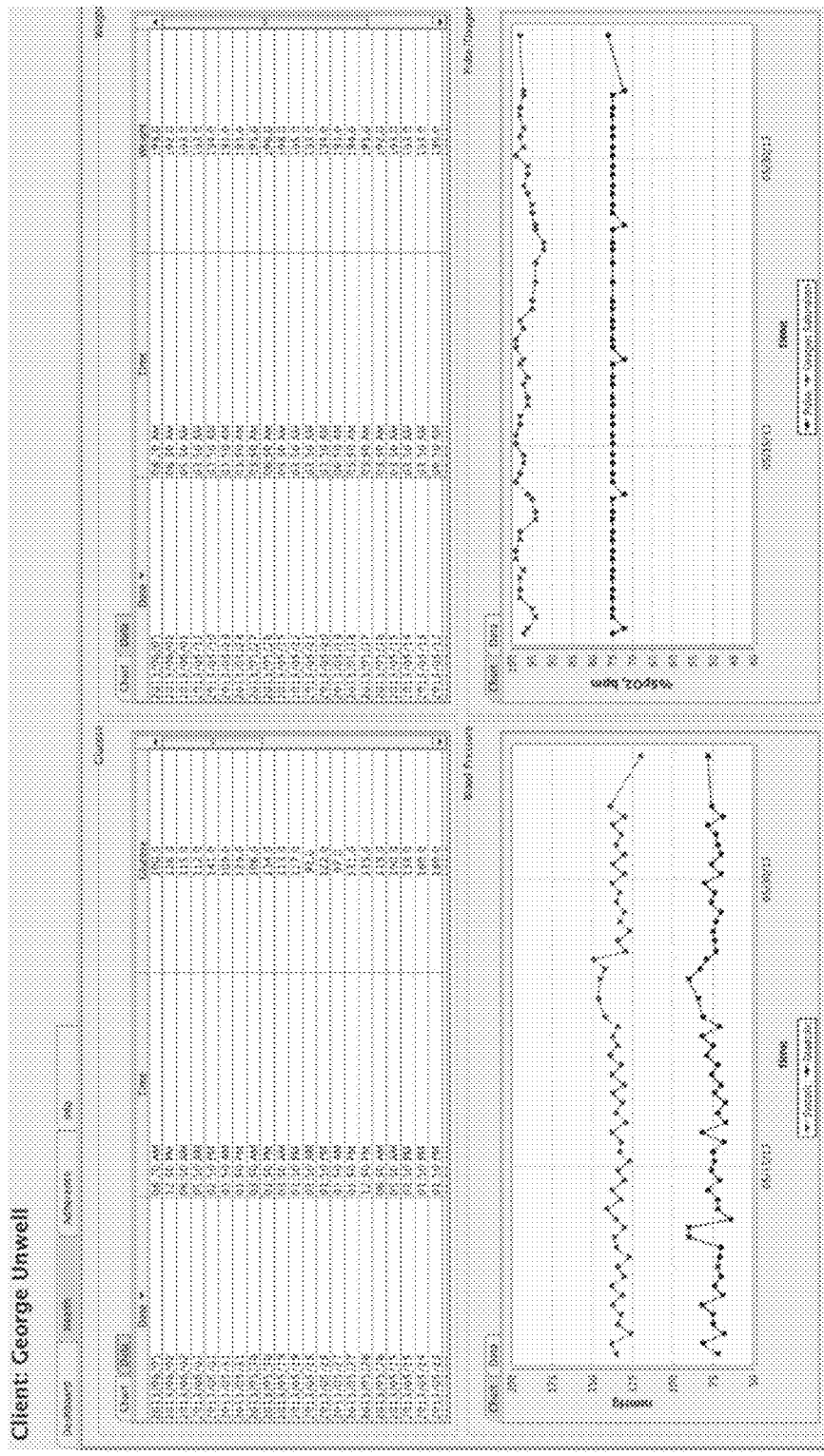
FIG. 62 illustrates the different viewing options, both graphic and statistic, of the user's health based on their recording of their vitals.
Figure 63:
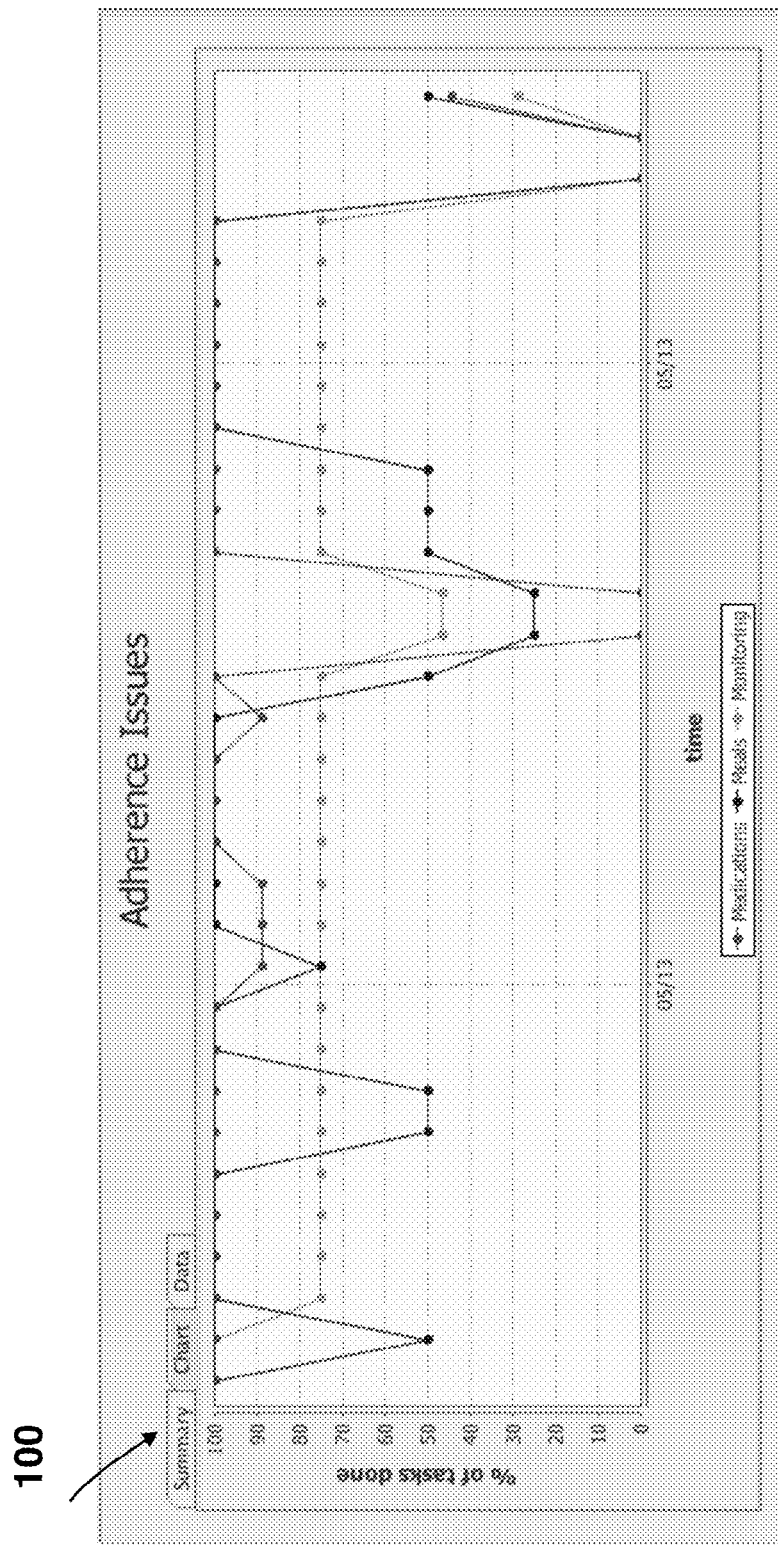
FIG. 63 illustrates the user's overall adherence of meals, medication, and monitoring all on the same graph.

FIG. 55-63 show various user interfaces in the care-portal of the PCIMS application. FIG. 55 depicts the main interface that provides an overview on whether tasks have been completed or not. It also summarizes health alerts and alerts concerning adherence to the care plan. FIG. 56 depicts the details of a health alert. FIG. 62 depicts the details of overall adherence to the care-plan.

Figure 57:
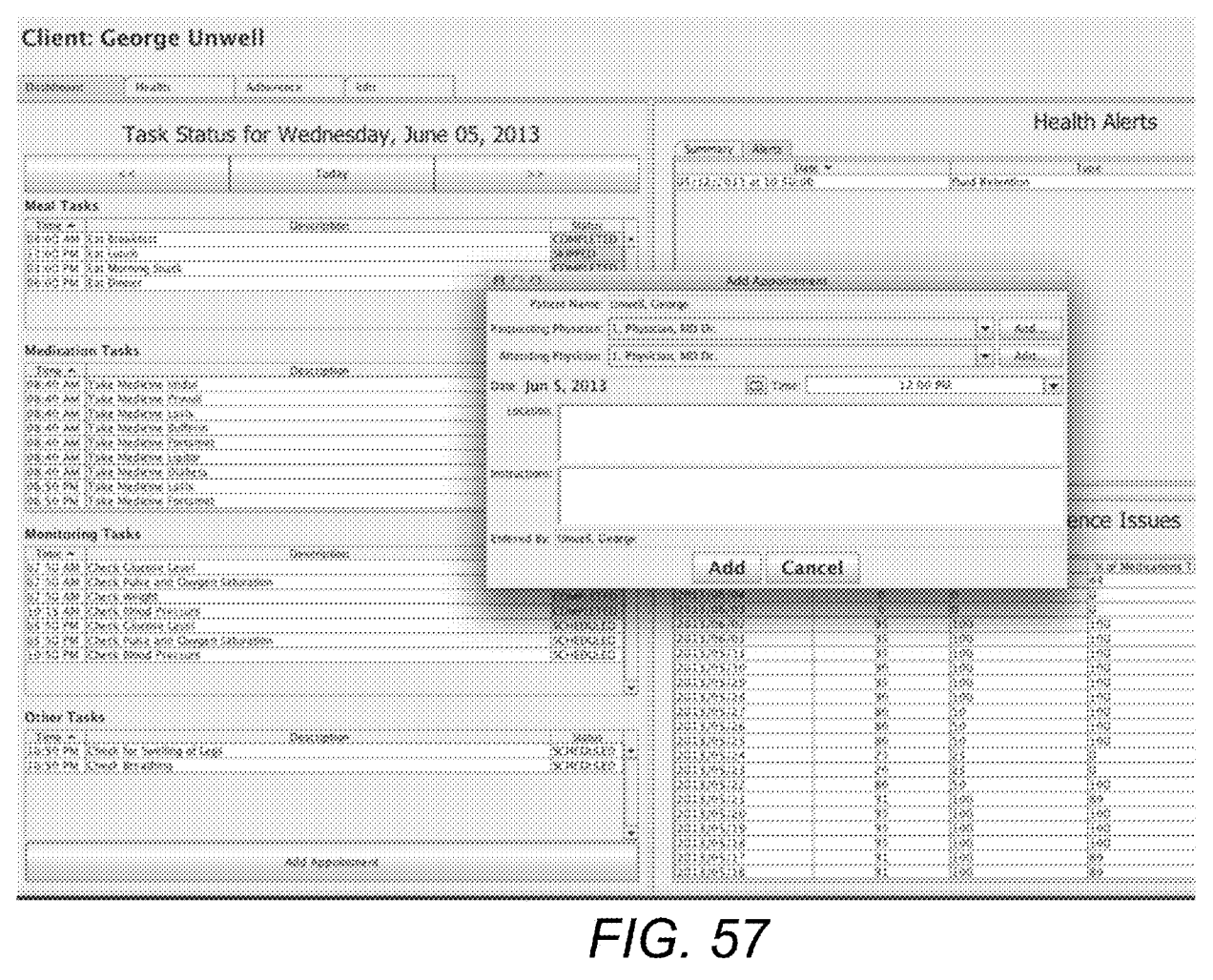

The care-portal is the interface to the semantic knowledge base that a caregiver uses to assist the client whose behavior is activated through care-station interface. FIG. 57 depicts an interface for managing clinical appointments.

Figure 58:
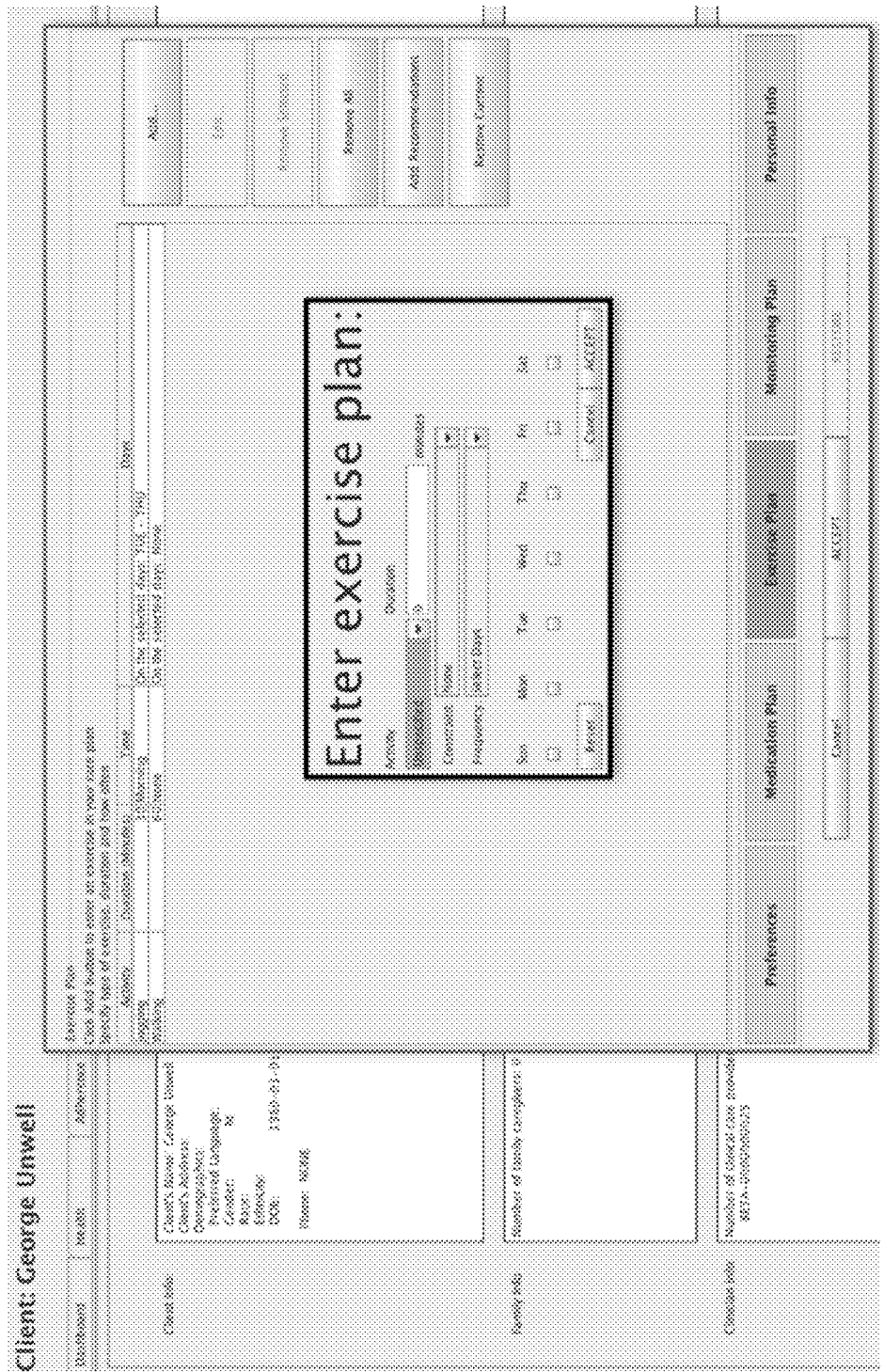
FIG. 58 illustrates the care-portal's provision to update the user's care plan, such as an exercise plan.
Figure 59:
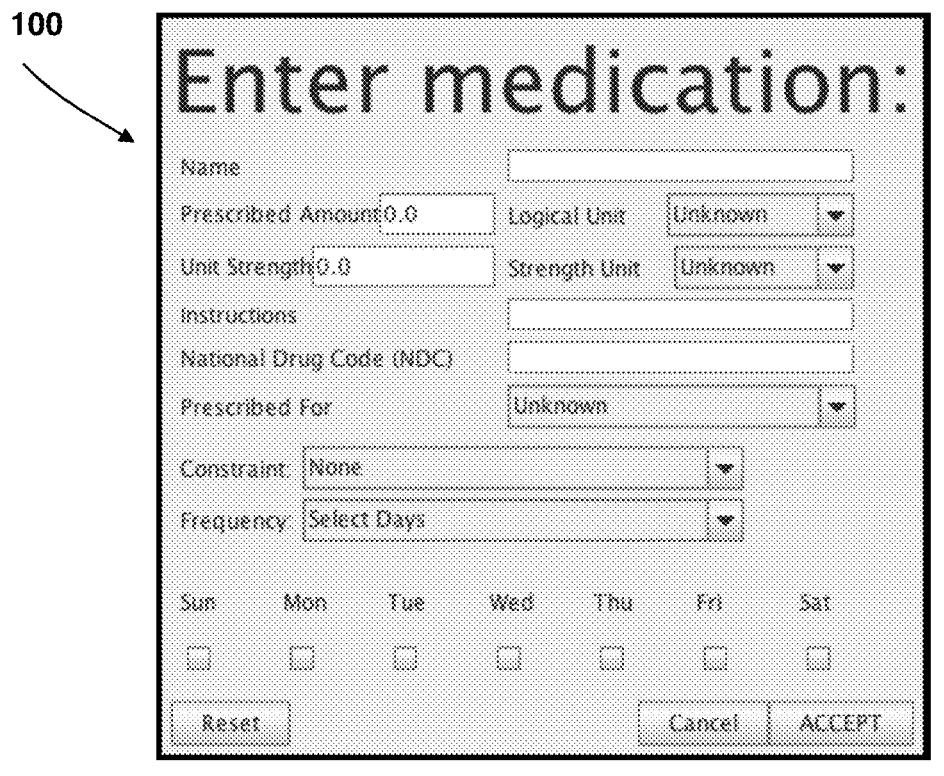

FIG. 58 and FIG. 59 depict a couple of different forms that the user uses to create the care plan. These inputs dictate what tasks are scheduled everyday and when. As shown in FIG. 58, the care plan specifies an exercise plan to include what exercises are to be done and how often. The frequency specification can be in terms of specific days of the week or a high level constraint such as two times a week. The inference processes the care plan input to schedule daily activities, which are depicted as tasks in the care-station.

FIG. 59 depicts the specification of a medication to be taken. Dosage, frequency and constraints on when to take the medication, such as before breakfast are part of the specification. the inference engine processes the specification daily and activates the user to take the medication accordingly. FIG. 60 summarizes all the medications that are part of the user's care plan.

FIG. 61 and FIG. 62 depict interfaces to look at the history of health and adherence data. The history is analyzed by the inference engine to characterize trends in health and behavior. Health trends are based on vital signs. Behavioral trends are based on whether tasks are completed in a timely fashion or not. The inference engine uses the trends to tailor the manner is which the user is activated. As in the example depicted in FIG. 23, if the trend shows gradual decline in medication adherence until user is reminded of its importance, PCIMS will provide timely education to prevent the anticipated decline in adherence.

The PCIMS application illustrates the vast and diverse range of data that can be processed by the semantic reasoning framework of the present invention. All data and the associated processing are defined in the semantic model in terms of concepts, notes, relationships and repertoire functions. The semantic model can be extended as needed when more data needs to be factored into the inferencing process or when other types of decision support are needed. An extensible inference process through which data is automatically processed into insights is essence of the present invention.

Figure 64:
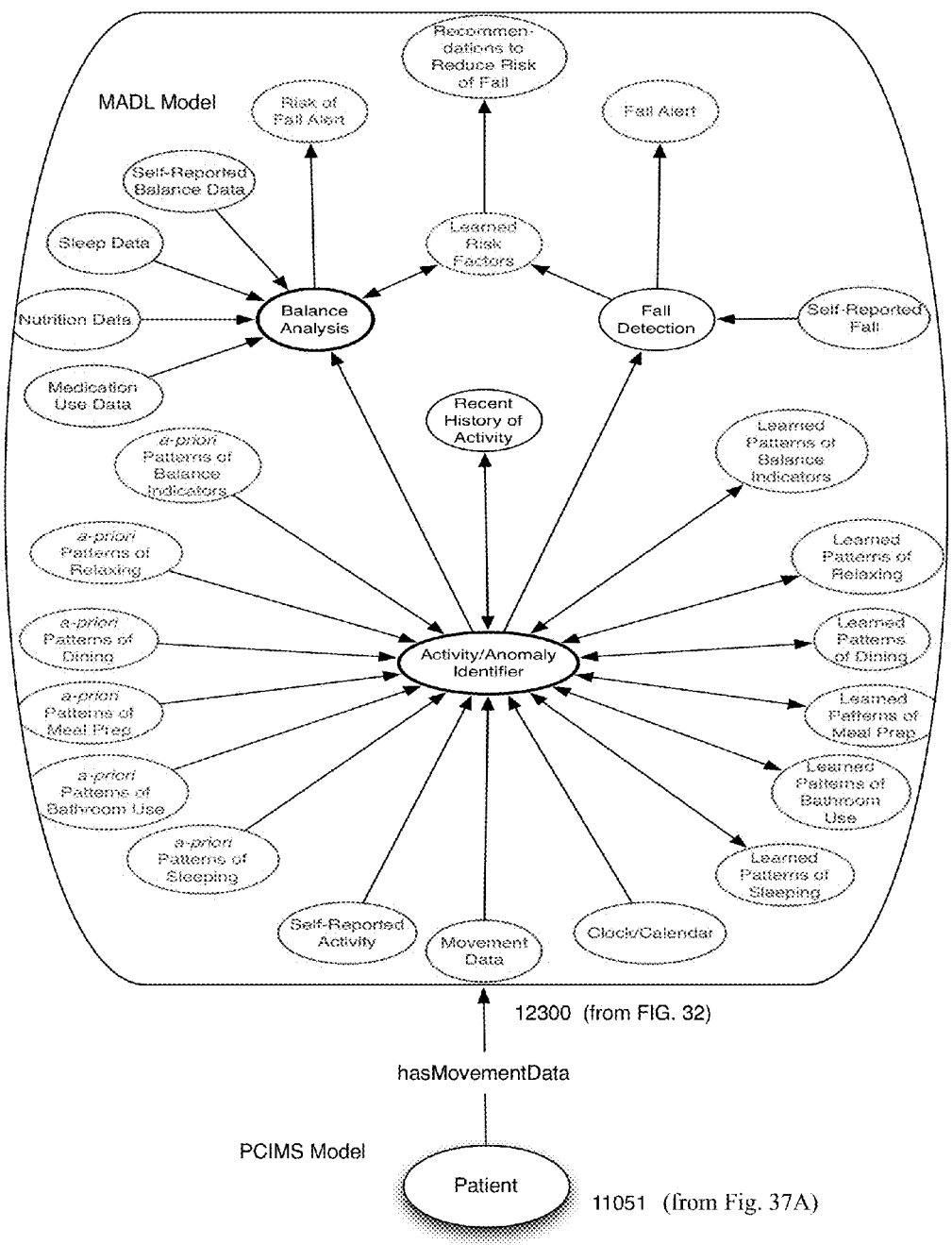
FIG. 64 illustrates one example of extending the semantic model by joining multiple semantic models.
Figure 65:
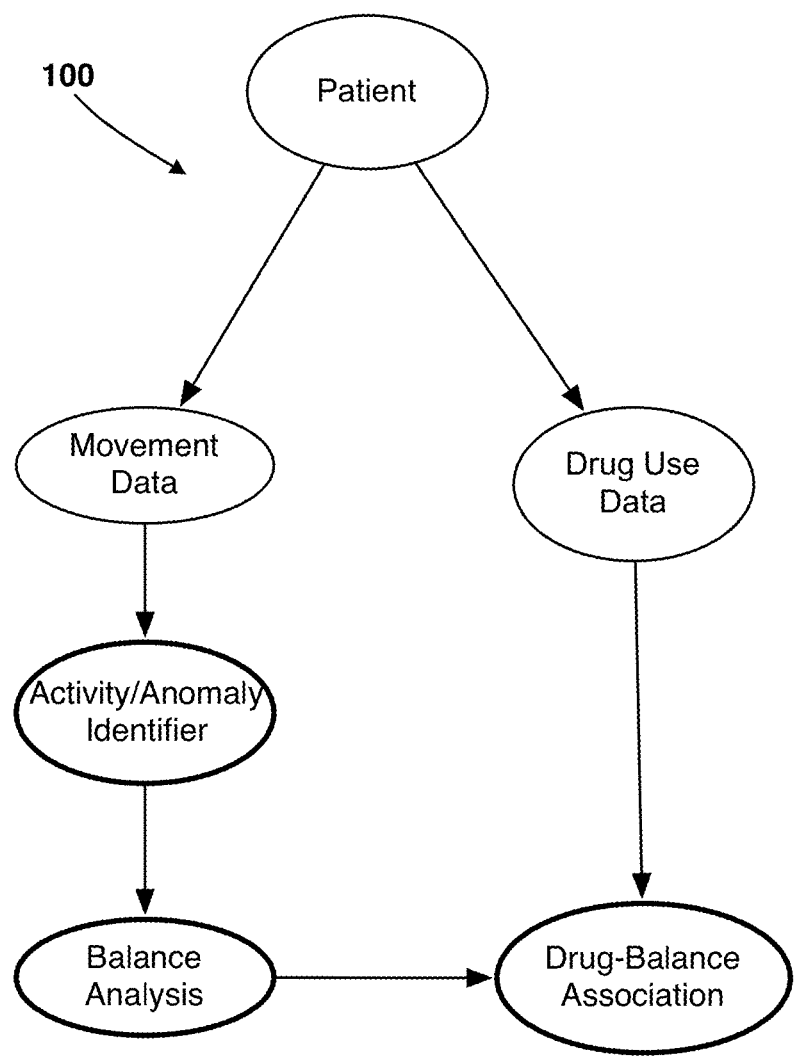
FIG. 65 illustrates another example of extending the semantic model by adding new insight concepts.

The PCIMS application is extended simply by adding to the semantic model. New fact concepts can be added when new sources of data become available. New insight concepts can be added to extend the process of inferences. FIG. 64 provides one example of extending an application by adding to the semantic model. In this example, two different applications, PCIMS and MADL, are joined through one or more shared concept. One shared concept is movement data. Through inferences about movement data, the MADL application creates knowledge activities of daily living: how much time is spent doing key daily activities. The MADL application also continuously assesses balance to detect high likelihood of falls. When the semantic model of MADL is integrated with the semantic model of PCIMS, new opportunities of inferences are created. FIG. 65 presents an example where patterns of movement, learned in the MADL application, are correlated with use of medications, which is discerned in the PCIMS application. The additional concept, correlating movement to drug use, detects if an individual's balance if affected by her medications. The examples of FIG. 64 and FIG. 65 illustrates one of the principle strengths of the present teachings that inferences are incrementally added, building upon previous inferences, simply by extending the semantic model. In many instances, no additional coding is required when the semantic model is extended. The inference engine simply applies the extended semantic to data to create the additional knowledge that is represented by the added concepts and relationships. In some instance, extending the semantic model may require definition of some repertoire functions through the meta-language described in the present teaching. New repertoire functions themselves may extend existing repertoire functions, adding to the extensibility of the inference process of the present teachings.

The PCIMS application reasons over many different data sources and draws complex conclusions that are built upon other conclusions. Such applications require an extensible inference process. The method and system described in the present teaching, presents an applicable, extensible inference process. Through its extensible semantic model, its application independent inference engine, and the extensible meta-language to extract knowledge from the knowledge base populated by the inference engine, the present teachings extend the prior art of semantic representation of knowledge to include systematic reasoning for creating new knowledge.

Several embodiments of the present invention have been described. Nevertheless, it will be understood that various modifications may be made without departing from the spirit and scope of the invention. Accordingly, other embodiments are within the scope of the following claims.

What is claimed is:

1. A system for providing semantic reasoning comprising:
   an extended semantic model of a specific knowledge domain comprising existing concepts, existing relationships among the existing concepts, and inference logic embedded within each existing concept, wherein each existing concept comprises associated properties and wherein the embedded inference logic is used for inferring values of said associated properties and comprises conditions and processes for drawings inferences about an existing downstream concept that is connected to an existing concept via an existing relationship;
   a semantic knowledge database being distinct from the extended semantic model and comprising existing nodes and existing links and wherein the existing nodes represent instances of the existing concepts, and the existing links represent instances of the existing relationships among the existing concepts;
   an inference engine configured to populate the semantic knowledge database with said instances of the existing concepts and said instances of the existing relationships by following the inference logic embedded within each existing concept, and wherein the inference engine adds new nodes and new links to the semantic knowledge database by first receiving external data, next generating instances of fact nodes and associated links representing said external data, and then recursively adding and updating downstream insight nodes and associated links;
   a computing system comprising at least a processor configured to execute the inference engine operating on the inference logic of the extended semantic model and to host the semantic knowledge database;
   wherein each existing node comprises existing notes representing instances of the associated properties of each existing concept;
   wherein the existing links that connect the existing nodes comprise directionality originating from an upstream node and terminating at a downstream node; and
   wherein the system further comprises a user interface configured to query the semantic knowledge database and to provide decision support to a user.

2. The system of claim 1, further comprising a data normalizer configured to receive said external data and normalize them to the existing concepts and existing relationships of the extended semantic model.

3. The system of claim 1, further comprising a repertoire library and wherein the repertoire library comprises a set of repertoire functions, wherein each repertoire function is assigned an unique identifier number that associates the repertoire function with the inference logic embedded in each concept in the extended semantic model and wherein the repertoire functions are automatically invoked by the inference engine in the process of adding and updating insight nodes.

4. The system of claim 3, wherein the set of repertoire functions comprise one of resolver, context-gate, collector, qualifier or operators, and wherein each type of repertoire function fulfills a specific role in the inference process.

5. The system of claim 4, wherein a resolver function defined within a concept specifies the set of conditions and processes to decide whether a new instance of the concept is to be created.

6. The system of claim 4, wherein a qualifier function defined within a concept specifies the conditions that are required to be met in order for a node to be able to populate its own properties or is able to initiate the creation of downstream nodes and wherein the qualifier function is invoked when a node is created or updated.

7. The system of claim 4, wherein an operator function defined within a concept specifies the conditions and processes through which values are assigned to the properties defined within the concept and wherein the operator is invoked when the conditions set within the qualifier functions has been met.

8. The system of claim 4, wherein the collector function within a concept specifies the processes through which the nodes that are links to attributes in upstream nodes are populated and wherein the collector functions are involved after the operator functions of the concept have been invoked.

9. The system of claim 4, wherein the context-gate function defined within a concept decides whether notes within all the upstream nodes required to create a downstream node have met the conditions needed to create new downstream nodes and wherein the context-gate function is invoked after the operator functions of the concept have been invoked.

10. The system of claim 1, wherein the extended semantic model further comprises upstream concepts and downstream concepts and wherein the upstream concepts are connected to the downstream concepts via relationships, and wherein the inference logic of each upstream concept further comprises conditions and processes for creating and updating instances of corresponding downstream concepts and wherein each of the downstream concepts is automatically inferred by the inference engine using the inference logic embedded in a corresponding upstream concept whenever the corresponding upstream concept is instanced as a node or when the node is modified and the conditions for creating or updating the downstream concept are met.

11. The system of claim 1, wherein each of said properties comprises values associated with an existing concept or a chain of links connecting data within an upstream concept with a downstream concept and wherein said properties are used by the inference engine for implementing the logic for instancing an associated link to a downstream concept or for instancing properties of said downstream concept.

12. The system of claim 1, further comprising an extensible meta-language for querying the semantic knowledge base and wherein the extensible meta-language comprises a vocabulary of fundamental words that are common to all extended semantic models and independent of any specific domain knowledge contained in any specific semantic model and wherein the inference engine has a built-in interpreter that can perform the actions specified in the fundamental words, and wherein the inference engine can interpret a collection of words built from fundamental words and wherein new domain specific query words are built upon the fundamental words such that they can be interpreted and implemented by the inference engine without the inference engine being coded with domain specific query logic.

13. The system of claim 12, wherein the extensible meta-language comprises an extension of a FORTH language and wherein the interpreter comprises a FORTH language interpreter.

14. The system of claim 1, wherein the computing system comprises a mechanism for storing and retrieving knowledge to and from the semantic knowledge base that is distributed over multiple computing systems.

15. The system of claim 1, wherein the extended semantic model is extended by adding new fact concepts, new insight concepts, or another extended semantic model and wherein the addition of each new insight concept includes specifying within its upstream concepts the logic to adding or updating the new insight concept.

16. The system of claim 1, used for automating financial transactions, wherein the existing concepts comprise customers, banks, bank accounts and financial transactions.

17. The system of claim 1, used for monitoring activities of daily living, wherein the existing concepts comprise users, sensor devices, data transmitters and activity data.

18. The system of claim 1, used for personal chronic illness management, wherein the existing concepts comprise users, sensor devices, data transmitters and care activities and protocols.

19. The system of claim 1, wherein adding or updating of a fact node in the semantic knowledge database automatically triggers the inference logic to add or update all downstream insight nodes that can be linked to the fact node and wherein addition or update of downstream insight nodes are inferred from an upstream fact node using the inference logic embedded in the upstream concept whose instance is the fact node.

20. The system of claim 1, wherein adding or updating of an insight node in the semantic knowledge database automatically triggers the inference logic to add or update all downstream insight nodes that can be linked to the insight node and wherein addition or update of downstream insight nodes are inferred from an upstream insight node using the inference logic embedded in an upstream concept whose instance is the triggering insight node.

21. The system of claim 1, wherein the inference engine does not comprise any specific knowledge domain inference logic on how to populate the semantic knowledge database.

22. A method for providing semantic reasoning comprising:
providing an extended semantic model of a specific knowledge domain comprising existing concepts, existing relationships among the existing concepts, and inference logic embedded within each existing concept, wherein each existing concept comprises associated properties and wherein the embedded inference logic is used for inferring values of said associated properties and comprises conditions and processes for drawings inferences about an existing downstream concept that is connected to an existing concept via an existing relationship;
providing a semantic knowledge database being distinct from the extended semantic model and comprising existing nodes, and existing links and wherein the existing nodes represent instances of the existing concepts, and the existing links represent instances of the existing relationships;
providing an inference engine configured to populate the semantic knowledge database with said instances of the existing concepts and said instances of the existing relationships by following the inference logic embedded within each concept, and to add new concepts and relationships to the semantic knowledge database by first receiving external data, next generating instances of fact nodes and associated links representing said external data, and then recursively adding and updating downstream insight nodes and associated links; and
providing a computing system comprising at least a processor configured to execute the inference engine operating on the inference logic of the extended semantic model and to host the semantic knowledge database;
providing a user interface configured to query the semantic knowledge database and to provide decision support to a user;
wherein each existing node comprises existing notes representing instances of the associated properties of each existing concept; and
wherein the existing links that connect the existing nodes comprise directionality originating from an upstream node and terminating at a downstream node.

* * * * *